US005952306A

United States Patent [19]

Hartman et al.

[11] Patent Number: 5,952,306

[45] **Date of Patent: *Sep. 14, 1999**

[54] INTEGRIN RECEPTOR ANTAGONISTS

[75] Inventors: George D. Hartman, Lansdale; Mark E. Duggan, Schwenksville; James J. Perkins, Churchville; Cecilia A. Hunt, Plymouth Meeting; Amy E. Krause, Blue Bell; John H. Hutchinson, Philadelphia; Benny C. Askew, Lansdale; Karen M. Brashear, Perkasie, all of Pa.; Nathan C. Ihle, Mercer Island, Wash.

[73] Assignee: Merck & Co., Inc., Rahway, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/783,635

[22] Filed: Jan. 14, 1997

Related U.S. Application Data XX .

[60] Provisional application No. 60/009,965, Jan. 16, 1996.

[51] Int. Cl.$^6$ .......................... C07K 5/023; A61K 38/05; A61K 38/06

[52] U.S. Cl. .............................. 514/18; 514/19; 544/360; 544/393; 546/122; 546/194; 546/273.4; 546/277.4; 546/300; 546/309; 546/331

[58] Field of Search ........................ 514/18, 19; 546/309, 546/277.4, 300, 122, 273.4, 194, 331; 544/393, 360

[56] References Cited

U.S. PATENT DOCUMENTS

| | | | |
|---|---|---|---|
| 3,553,227 | 1/1971 | Westland . | |
| 4,122,255 | 10/1978 | Krapcho et al. . | |
| 4,250,183 | 2/1981 | Krastinat | 560/20 |
| 4,684,722 | 8/1987 | Sundeen . | |
| 5,227,490 | 7/1993 | Hartman et al. . | |
| 5,264,420 | 11/1993 | Duggan et al. . | |
| 5,281,585 | 1/1994 | Duggan et al. . | |
| 5,292,756 | 3/1994 | Duggan et al. . | |
| 5,294,616 | 3/1994 | Duggan et al. . | |
| 5,321,034 | 6/1994 | Duggan et al. . | |
| 5,358,956 | 10/1994 | Hartman et al. . | |

FOREIGN PATENT DOCUMENTS

| | | |
|---|---|---|
| 0 372 486 | 6/1990 | European Pat. Off. . |
| 0 381 033 | 8/1990 | European Pat. Off. . |
| 0 384 362 | 8/1990 | European Pat. Off. . |
| 9509634 | 4/1995 | WIPO . |
| 9708145 | 3/1997 | WIPO . |

*Primary Examiner*—Robert Gerstl
*Attorney, Agent, or Firm*—Richard S. Parr; Melvin Winokur

[57] ABSTRACT

Fibrinogen receptor antagonists having the formula

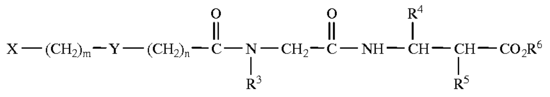

for example

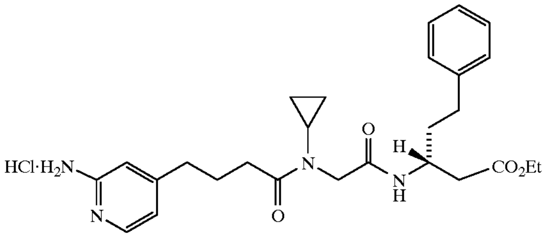

which are useful for inhibiting the binding of fibrinogen to blood platelets and for inhibiting the aggregation of blood platelets.

8 Claims, No Drawings

INTEGRIN RECEPTOR ANTAGONISTS

This application is a Provisional of Application No. 60/009,965, filed Jan. 16, 1996.

BACKGROUND OF THE INVENTION

The invention relates generally to modulating cell adhesion and to inhibiting the binding of fibrinogen and other proteins to blood platelets, and inhibiting the aggregation of blood platelets specifically to the gp IIb/IIIa fibrinogen receptor site. Fibrinogen is a glycoprotein present in blood plasma that participates in platelet aggregation and in fibrin formation. Platelets are cell-like anucleated fragments, found in the blood of all mammals, that also participate in blood coagulation. Interaction of fibrinogen with the IIb/IIIa receptor site is known to be essential for normal platelet function.

When a blood vessel is damaged by an injury or other causative factor, platelets adhere to the disrupted subendothethial surface. The adherent platelets subsequently release biologically active constituents and aggregate. Aggregation is initiated by the binding of agonists, such as thrombin, epinephrine, or ADP to specific platelet membrane receptors. Stimulation by agonists results in exposure of latent fibrinogen receptors on the platelet surface, and binding of fibrinogen to the glycoprotein IIb/IIIa receptor complex.

Attempts have been made to use natural products and synthetic peptides to determine the mechanism of adhesion and platelet aggregation. For example, Rouslahti and Pierschbacher in *Science,* 238, 491–497 (1987), describe adhesive proteins such as fibronectin, vitronectin, osteopontin, collagens, thrombospondin, fibrinogen, and von Willebrand factor that are present in extracellular matrices and in blood. The proteins contain the tripeptide arginine-glycine-aspartic acid (RGD) as their glycoprotein IIb/IIIa recognition site. These arginine-glycine-aspartic acid containing tripeptides are recognized by at least one member of a family of structurally related receptors, integrins, which are heterodimeric proteins with two membrane-spanning subunits. The authors state that the conformation of the tripeptide sequence in the individual proteins may be critical to recognition specificity.

Cheresh in *Proc. Nat'l Acad. Sci. U.S.A.,* 84, 6471–6475, (1987), describes an Arg-Gly-Asp directed adhesion receptor expressed by human endothethial cells that is structurally similar to the IIb/IIIa complex on platelets but is antigenically and functionally distinct. This receptor is directly involved in endothelial cell attachment to fibrinogen, von Willebrand factor, and vitronectin.

Pierschbacher and Rouslahti, in *J. of Biol. Chem.,* 262, (36), 17294–17298 (1987) hypothesized that the Arg-Gly-Asp sequence alone would be a sufficient signal for receptor recognition and binding and that, therefore, the conformation of the tri-peptide sequence would be determinative. Various synthetic peptides were produced and the authors concluded that the sterochemical conformation of Arg-Gly-Asp as influenced by enantiomeric substitutions or additions to this sequence significantly influenced receptor-ligand interaction. The authors further showed that cyclization of a decapeptide by forming a disulfide bridge between non-terminal residues Pen and Cys, rendered the peptide much less effective at inhibiting attachment to fibronectin.

In *Proc. Nat'l Acad. Sci. U.S.A.,* 81, 5985–5988 (1984), the same authors describe tetrapeptide variants of the cell recognition site of fibronectin that retain attachment-promoting activity. Peptides having a tetrapeptide recognition site are described in U.S. Pat. Nos. 4,589,881 and 4,614,517. A number of large polypeptide fragments in the cell-binding domain of fibronectin have cell-attachment activity. For example, see U.S. Pat. Nos. 4,517,686, 4,661,111 and U.S. Pat. No. 4,578,079.

Ruggeri et al., *Proc. Nat'l Acad. Sci. U.S.A.,* 83, 5708–5712 (1986) explore a series of synthetic peptides designed in lengths to 16 residues, that contain RGD and a valine attached to the aspartic acid residue of RGD that inhibit fibrinogen binding to platelets. See also Koczewiak et al., *Biochem.,* 23, 1767–1774 (1984); Ginsberg et al., *J. Biol. Chem.,* 260(7), 3931–3936 (1985); and Haverstick et al., *Blood,* 66(4), 946–952 (1985). Other inhibitors are disclosed in Eur. Pat. App. Nos. 275,748 and 298,820.

A number of low molecular weight polypeptide factors have been isolated from snake venom. These factors apparently have high affinity for the gp IIb/IIIa complex. For example, Huang et al., *J. Biol Chem.,* 262, 16157–16163 (1987); Huang et al., *Biochemistry,* 28, 661–666 (1989) describe the primary structure of the venom trigramin which is a 72 amino acid polypeptide that contains the RGD subunit. Echistatin is another compound which has high affinity for the gp IIb/IIIa complex. This polypeptide contains 49 amino acids and has the RGD subunit and various disulfide bridges. Gan et al., *J. Biol. Chem.,* 263, 19827–19832 (1988). See also, Dennis et al., *Proc. Nat'l Acad. Sci. USA,* 87, 2471–2475 (1989). However, these snake venom factors also have high affinity for other members of the adhesive protein receptor family including the vitronectin and fibronectin receptors so are not selective for the gp IIb/IIIa complex.

While it is known that the tripeptide sequence Arg-Gly-Asp is present in certain polypeptides that can duplicate or inhibit the cell attachment-promoting effects of fibronectin and vitronectin, the tripeptide Arg-Gly-Asp has low activity. At present, there is little understanding of how other amino acids coupled to this sequence influence binding specificity. U.S. Pat. No 5,023,233, assigned to Merck & Co., Inc., discloses small cyclic hexapeptides which contain the sequence Arg-Gly-Asp and are useful platelet aggregation inhibitors. U.S. Pat. No. 5,037,808 discloses the use of indolyl platelet-aggregation inhibitors which are believed to act by antagonizing interactions between fibrinogen and/or extracellular matrix proteins and the platelet gp IIb/IIIa receptor. U.S. Pat. No. 5,037,808 discloses guanidino peptide mimetic compounds that retain an Asp residue which inhibit platelet aggregation. The application PCT/US90/02746 describes the use of antibody-poly-peptide conjugates wherein said polypeptides contain the Arg-Gly-Asp (RGD) sequence.

The application PCT/US91/00564 discloses the use of large cyclic peptides containing RGD flanked by proline residues which are platelet aggregation inhibitors. The application PCT/US90/03788 discloses small cyclic platelet aggregation inhibitors which are synthetic cyclic pentapeptides containing the tripeptide sequence Arg-Gly-Asp and a thioether linkage in the cycle. The application PCT/US90/05367 published May 2, 1991 also discloses the use of peptides and pseudopeptides such as N-amidino-piperidine-3-carboxylglycyl-L-aspartyl-L-valine that inhibit platelet aggregation and thrombus formation in mammalian blood. The application Eur. Pat. App. No. 91103462.7 discloses linear compounds which can include internal piperazinyl or piperidinyl derivatives. Eur. Pat. App. No. 91300179.8, assigned to Merck & Co., Inc., and published on Jul. 17, 1991 discloses linear polypeptide fibrinogen receptor antagonists. Eur. Pat. App. No. 90101404.3 discloses compounds of the $R^1$-A-$(W)_a$-X-$(CH_2)_b$-$(Y)_c$-B-Z-COOR wherein R 1 is a guandidino or amidino moiety and A and B are chosen from specific monosubstituted aryl or heterocyclic moieties.

While a multitude of compounds or peptide analogs believed to inhibit platelet aggregation by inhibiting binding to a blood platelet by fibrinogen are known, the present invention provides novel fibrinogen receptor antagonists that have significant binding activity and are, therefore, useful for the reasons stated herein. A number of very serious diseases and disorders involve hyperthrombotic complications which lead to intravascular thrombi and emboli. Myocardial infarction, stroke, phlebitis and a number of other serious conditions create the need for novel and effective fibrinogen receptor antagonists.

SUMMARY OF THE INVENTION

The invention is a compound of the formula:

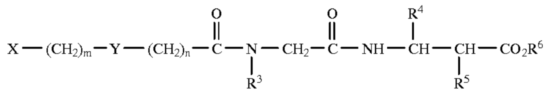

and pharmaceutically acceptable salts thereof, wherein X is

- a 5- or 6-membered monocyclic aromatic ring system containing 0, 1, 2, 3 or 4 heteroatoms selected from N, O and S and either unsubstituted or substituted with $R^1$ or $R^2$, or
- a 9- to 10-membered polycyclic ring system, wherein one or more of the rings is aromatic, containing 0, 1, 2, 3 or 4 heteroatoms selected from N, O and S and either unsubstituted or substituted with $R^1$ or $R^2$, wherein $R^1$ and $R^2$ are independently selected from the group consisting of hydrogen, F, Cl, Br, I,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino,
$C_{1-6}$ alkylamino $C_{1-8}$ alkyl,
$C_{1-6}$ dialkylamino,
$C_{1-6}$ dialkylamino $C_{1-8}$ alkyl,
$C_{1-4}$ alkoxy,
$C_{1-4}$ alkoxy $C_{1-6}$ alkyl,
carboxy,
carboxy $C_{1-6}$ alkyl,
$C_{1-3}$ alkoxycarbonyl,
$C_{1-3}$ alkoxycarbonyl $C_{1-6}$ alkyl,
carboxy $C_{1-6}$ alkyloxy and
hydroxy,
hydroxy $C_{1-6}$ alkyl;

Y is

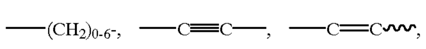

-continued

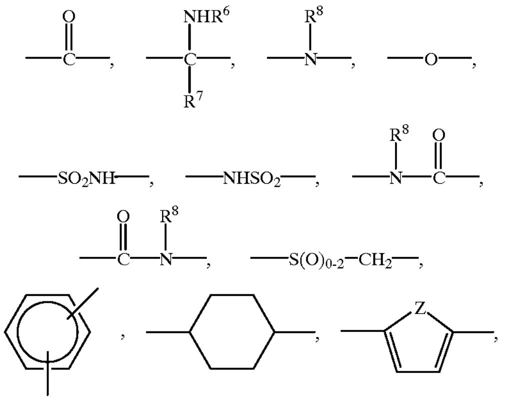

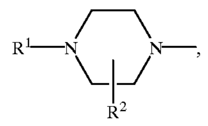

or

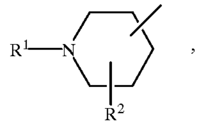

where Z is O, $NR^8$, or S; and $R^8$ is defined as $R^1$ above; $R^3$ and $R^4$ are independently hydrogen,
a five or six membered mono or polycyclic aromatic ring system containing 0, 1, 2, 3, or 4 heteroatoms selected from nitrogen, oxygen and sulfur, either unsubstituted or substituted, with one or more groups selected from hydroxyl, halogen, cyano, trifluoromethyl, $C_{1-3}$ alkoxy, $C_{1-5}$ alkylcarbonyloxy, $C_{1-5}$ alkoxycarbonyl, $C_{1-5}$ alkyl, amino$C_{1-5}$ alkyl, hydroxycarbonyl, hydroxycarbonyl$C_{1-5}$ alkyl, or hydroxycarbonyl$C_{1-5}$ alkoxy,
—$(CH_2)_n$-aryl, wherein n=1–4 and aryl is defined as a five or six membered mono or polycyclic aromatic ring system containing 0, 1, 2, 3, or 4 heteroatoms selected from nitrogen, oxygen and sulfur, either unsubstituted or substituted, with one or more groups selected from hydroxyl, halogen, cyano, trifluoromethyl, $C_{1-3}$ alkoxy, $C_{1-5}$ alkylcarbonyloxy, $C_{1-5}$ alkoxycarbonyl, $C_{1-5}$ alkyl, amino$C_{1-5}$ alkyl, hydroxycarbonyl, hydroxycarbonyl$C_{1-5}$ alkyl, or hydroxycarbonyl$C_{1-5}$ alkoxy,
halogen,
hydroxyl,
$C_{1-5}$alkylcarbonylamino,
aryl$C_{1-5}$ alkoxy,
$C_{1-5}$ alkoxycarbonyl,
aminocarbonyl,
$C_{1-5}$ alkylaminocarbonyl,
$C_{1-5}$ alkylcarbonyloxy,
$C_{3-8}$ cycloalkyl,
oxo,
amino,
$C_{1-3}$ alkylamino,
amino$C_{1-3}$ alkyl,
arylaminocarbonyl,
aryl$C_{1-5}$ alkylaminocarbonyl,
aminocarbonyl,
aminocarbonyl-$C_{1-4}$ alkyl,
hydroxycarbonyl, hydroxycarbonyl $C_{1-5}$ alkyl, $C_{1-6}$alkyl, either unsubstituted or substituted, with one or more groups selected from halogen, hydroxyl, $C_{1-5}$ alkylcarbonylamino, aryl$C_{1-5}$ alkoxy, $C_{1-5}$ alkoxycarbonyl, aminocarbonyl, $C_{1-5}$ alkylaminocarbonyl, $C_{1-5}$ alkylcarbonyloxy, $C_{3-8}$ cycloalkyl, oxo, amino, $C_{1-3}$ alkylamino, amino$C_{1-3}$ alkyl, arylaminocarbonyl, aryl$C_{1-5}$alkylaminocarbonyl, aminocarbonyl, aminocarbonyl-$C_{1-4}$ alkyl, hydroxycarbonyl, or hydroxycarbonyl $C_{1-5}$ alkyl, provided that the carbon atom to which $R^3$ and $R^4$ are attached bears only one heteroatom, —$(CH_2)_m$ C≡CH, —$(CH_2)_m$ C≡C—$C_{1-6}$ alkyl, —$(CH_2)_m$ C≡C—$C_{3-7}$cycloalkyl, —$(CH_2)_m$ C≡C-aryl, —$(CH_2)_m$ C≡C—$C_{1-6}$ alkyl aryl, —$(CH_2)_m$ CH=$CH_2$, —$(CH_2)_m$ CH=CH $C_{1-6}$ alkyl, —$(CH_2)_m$ CH=CH—$C_{3-7}$cycloalkyl, —$(CH_2)_m$ CH=CH aryl, —$(CH_2)_m$ CH=CH $C_{1-6}$ alkyl aryl, —$(CH_2)_m$ $SO_2C_{1-6}$ alkyl, or —$(CH_2)_m$ $SO_2C_{1-6}$ alkylaryl;

$R^5$is hydrogen, fluorine, $C_{1-8}$ alkyl, hydroxyl, hydroxy $C_{1-6}$ alkyl, carboxy, carboxy $C_{1-6}$ alkyl, $C_{1-6}$ alkyloxy.

$C_{3-8}$ cycloalkyl, aryl $C_{1-6}$ alkyloxy, aryl, aryl $C_{1-6}$ alkyl, $C_{1-6}$ alkylcarbonyloxy, amino, amino $C_{1-6}$ alkyl, $C_{1-6}$ alkylamino, $C_{1-6}$ alkylamino $C_{1-6}$ alkyl, aryl amino, aryl amino $C_{1-6}$ alkyl, aryl $C_{1-6}$ alkylamino, aryl $C_{1-6}$ alkylamino $C_{1-6}$ alkyl, aryl carbonyloxy, aryl $C_{1-6}$ alkylcarbonyloxy, $C_{1-6}$ dialkylamino, $C_{1-6}$ dialkylamino $C_{1-6}$ alkyl, $C_{1-6}$ alkylaminocarbonyloxy, $C_{1-8}$ alkylsulfonylamino, $C_{1-8}$ alkylsulfonylamino $C_{1-6}$ alkyl, aryl sulfonylamino $C_{1-6}$ alkyl, aryl $C_{1-6}$ alkylsulfonylamino, aryl $C_{1-6}$ alkylsulfonylamino $C_{1-6}$ alkyl, $C_{1-8}$ alkyloxycarbonylamino, $C_{1-8}$ alkyloxycarbonylamino $C_{1-8}$ alkyl, aryl oxycarbonylamino $C_{1-8}$ alkyl, aryl $C_{1-8}$ alkyloxycarbonylamino, aryl $C_{1-8}$ alkyloxycarbonylamino $C_{1-8}$ alkyl, $C_{1-8}$ alkylcarbonylamino, $C_{1-8}$ alkylcarbonylamino $C_{1-6}$ alkyl, aryl carbonylamino $C_{1-6}$ alkyl, aryl $C_{1-6}$ alkylcarbonylamino, aryl $C_{1-6}$ alkylcarbonylamino $C_{1-6}$ alkyl, aminocarbonylamino $C_{1-6}$ alkyl, $C_{1-8}$ alkylaminocarbonylamino, $C_{1-8}$ alkylaminocarbonylamino $C_{1-6}$ alkyl, aryl aminocarbonylamino $C_{1-6}$ alkyl, aryl $C_{1-8}$ alkylaminocarbonylamino, aryl $C_{1-8}$ aLkylaminocarbonylamino $C_{1-6}$ alkyl, aminosulfonylamino $C_{1-6}$ alkyl, $C_{1-8}$ alkylaminosulfonylamino, $C_{1-8}$ alkylaminosulfonylamino $C_{1-6}$ alkyl, aryl aminosulfonylamino $C_{1-6}$ alkyl, aryl $C_{1-8}$ alkylaminosulfonylamino, aryl $C_{1-8}$ alkylaminosulfonylamino $C_{1-6}$ alkyl, $C_{1-6}$ alkylsulfonyl, $C_{1-6}$ alkylsulfonyl $C_{1-6}$alkyl, aryl sulfonyl $C_{1-6}$alkyl, aryl $C_{1-6}$ alkylsulfonyl, aryl $C_{1-6}$ alkylsulfonyl $C_{1-6}$alkyl, $C_{1-6}$ alkylcarbonyl, $C_{1-6}$ alkylcarbonyl $C_{1-6}$ alkyl, aryl carbonyl $C_{1-6}$alkyl, aryl $C_{1-6}$ alkylcarbonyl, aryl $C_{1-6}$ alkylcarbonyl $C_{1-6}$alkyl, $C_{1-6}$ alkylthiocarbonylamino, $C_{1-6}$ alkylthiocarbonylamino $C_{1-6}$ alkyl, aryl thiocarbonylamino $C_{1-6}$ alkyl, aryl $C_{1-6}$ alkylthiocarbonylamino, aryl $C_{1-6}$ alkylthiocarbonylamino $C_{1-6}$ alkyl, aminocarbonyl $C_{1-6}$ alkyl, or $C_{1-8}$ alkylaminocarbonyl, or $C_{1-8}$ alkylaminocarbonyl $C_{1-6}$ alkyl, or aryl aminocarbonyl $C_{1-6}$ alkyl, aryl $C_{1-8}$ alkylaminocarbonyl, aryl $C_{1-8}$ alkylaminocarbonyl $C_{1-6}$ alkyl, wherein alkyl groups and aryl groups may be unsubstituted or substituted with one or more substituents selected from $R^1$ and $R^2$; and $R^6$ and $R^7$ are independently hydrogen, $C_{1-8}$ alkyl, aryl, aryl $C_{1-8}$ alkyl, hydroxy, $C_{1-8}$ alkyloxy, aryloxy, aryl $C_{1-6}$ alkyloxy, $C_{1-8}$ alkylcarbonyloxy $C_{1-4}$ alkyloxy, aryl C1-8 alkylcarbonyloxy $C_{1-4}$ alkyloxy, $C_{1-8}$ alkylaminocarbonylmethyleneoxy, or $C_{1-8}$ dialkylaminocarbonylmethyleneoxy
where m and n are integers 0–6.

In a class of compounds of the invention are compounds of the formula:

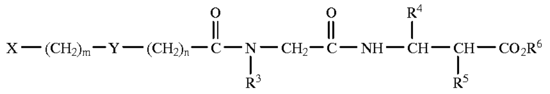

and pharmaceutically acceptable salts thereof, wherein
X is

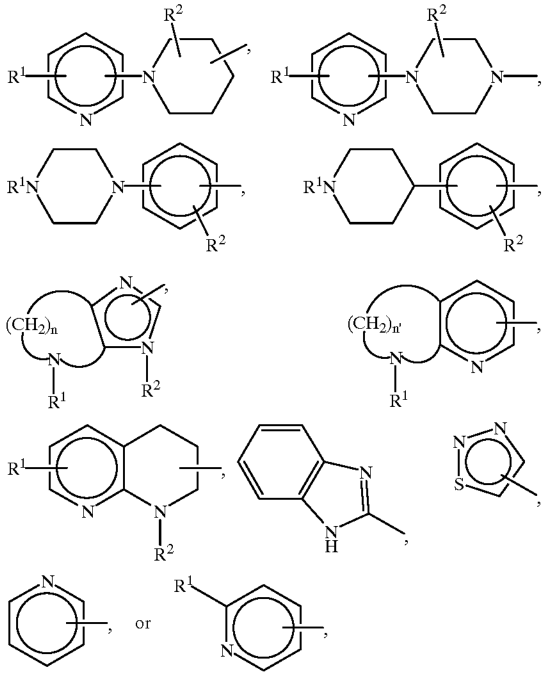

, or , wherein n is 2–4, and n' is 2 or 3, and
wherein $R^1$ and $R^2$ are independently selected from the group consisting of
hydrogen, F, Cl, Br, I,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino,
$C_{1-6}$ alkylamino $C_{1-8}$ alkyl,
$C_{1-6}$ dialkylamino,
$C_{1-6}$ dialkylamino $C_{1-8}$ alkyl,
$C_{1-4}$ alkoxy,
$C_{1-4}$ alkoxy $C_{1-6}$ alkyl,
carboxy,
carboxy $C_{1-6}$ alkyl,
$C_{1-3}$ alkoxycarbonyl,
$C_{1-3}$ alkoxycarbonyl $C_{1-6}$ alkyl,
carboxy $C_{1-6}$ alkyloxy and
hydroxy,
hydroxy $C_{1-6}$ alkyl;

$R^5$ is
hydrogen,
fluorine,
$C_{1-8}$ alkyl,
hydroxyl,
hydroxy $C_{1-6}$ alkyl,
carboxy,
carboxy $C_{1-6}$ alkyl,
$C_{1-6}$ alkyloxy.
$C_{3-8}$ cycloalkyl,
aryl $C_{1-6}$ alkyloxy,
aryl,
aryl $C_{1-6}$ alkyl,
$C_{1-6}$ alkylcarbonyloxy,
amino,
$C_{1-6}$ alkylamino,
amino $C_{1-6}$ alkyl,
$C_{1-6}$ alkylamino $C_{1-6}$ alkyl,
aryl amino,
aryl amino $C_{1-6}$ alkyl,
aryl $C_{1-6}$ alkylamino,
aryl $C_{1-6}$ alkylamino $C_{1-6}$ alkyl,
aryl carbonyloxy,
aryl $C_{1-6}$ alkylcarbonyloxy,
$C_{1-6}$ dialkylamino,
$C_{1-6}$ dialkylamino $C_{1-6}$ alkyl,
$C_{1-6}$ alkylaminocarbonyloxy,
$C_{1-8}$ alkylsulfonylamino,
$C_{1-8}$ alkylsulfonylamino $C_{1-6}$ alkyl,
aryl sulfonylamino $C_{1-6}$ alkyl,
aryl sulfonylamino,
aryl $C_{1-6}$ alkylsulfonylamino,
aryl $C_{1-6}$ alkylsulfonylamino $C_{1-6}$ alkyl,
$C_{1-8}$ alkyloxycarbonylamino,
$C_{1-8}$ alkyloxycarbonylamino $C_{1-8}$ alkyl,
aryl $C_{1-8}$ alkyloxycarbonylamino,
aryl oxycarbonylamino,
aryl oxycarbonylamino $C_{1-8}$ alkyl,
aryl $C_{1-8}$ alkyloxycarbonylamino $C_{1-8}$ alkyl,
$C_{1-8}$ alkylcarbonylamino,
$C_{1-8}$ alkylcarbonylamino CI-6 alkyl,
aryl carbonylamino $C_{1-6}$ alkyl,
aryl carbonylamino,
aryl $C_{1-6}$ alkylcarbonylamino,
aryl $C_{1-6}$ alkylcarbonylamino $C_{1-6}$ alkyl,
$C_{1-8}$ alkylaminocarbonylamino,
aminocarbonylamino,
aminocarbonylamino $C_{1-6}$ alkyl,
$C_{1-8}$ alkylaminocarbonylamino $C_{1-6}$ alkyl,
aryl aminocarbonylamino $C_{1-6}$ alkyl,
aryl aminocarbonylamino,
aryl $C_{1-8}$ alkylaminocarbonylamino,
aryl $C_{1-8}$ alkylaminocarbonylamino $C_{1-6}$ alkyl,
aminosulfonylamino $C_{1-6}$ alkyl,
aminosulfonylamino,
$C_{1-8}$ alkylaminosulfonylamino, $C_{1-8}$ alkylaminosulfonylamino $C_{1-6}$ alkyl,
aryl aminosulfonylamino $C_{1-6}$ alkyl,
aryl aminosulfonylamino,
aryl $C_{1-8}$ alkylaminosulfonylamino,
aryl $C_{1-8}$ alkylaminosulfonylamino $C_{1-6}$ alkyl,
$C_{1-6}$ alkylsulfonyl,
$C_{1-6}$ alkylsulfonyl $C_{1-6}$alkyl,
aryl sulfonyl,
aryl sulfonyl $C_{1-6}$alkyl,
aryl alkylsulfonyl,
aryl $C_{1-6}$ alkylsulfonyl,
aryl $C_{1-6}$ alkylsulfonyl $C_{1-6}$alkyl,
$C_{1-6}$ alkylcarbonyl,
$C_{1-6}$ alkylcarbonyl $C_{1-6}$ alkyl,
aryl carbonyl $C_{1-6}$alkyl,
aryl carbonyl,
aryl $C_{1-6}$ alkylcarbonyl,
aryl $C_{1-6}$ alkylcarbonyl $C_{1-6}$alkyl,
$C_{1-6}$ alkylthiocarbonylamino,
$C_{1-6}$ alkylthiocarbonylamino $C_{1-6}$ alkyl,
aryl thiocarbonylamino $C_{1-6}$ alkyl,
aryl thiocarbonylamino,
aryl $C_{1-6}$ alkylthiocarbonylamino,
aryl $C_{1-6}$ alkylthiocarbonylamino $C_{1-6}$ alkyl,
aminocarbonyl $C_{1-6}$ alkyl,
aminocarbonyl,
$C_{1-8}$ alkylaminocarbonyl,
$C_{1-8}$ alkylaminocarbonyl $C_{1-6}$ alkyl,
aryl aminocarbonyl $C_{1-6}$ alkyl,
aryl aminocarbonyl,
aryl $C_{1-8}$ alkylaminocarbonyl,
aryl $C_{1-8}$ alkylaminocarbonyl $C_{1-6}$ alkyl, wherein alkyl groups and aryl groups may be unsubstituted or substituted with one or more substituents selected from $R^1$ and $R^2$; and $R^6$ and $R^7$ are independently hydrogen,
$C_{1-8}$ alkyl,
aryl $C_{1-8}$ alkyl,
hydroxy,
$C_{1-8}$ alkyloxy,
aryl,
aryl $C_{1-6}$ alkyloxy,
$C_{1-8}$ alkylcarbonyloxy $C_{1-4}$ alkyloxy,
aryl $C_{1-8}$ alkylcarbonyloxy $C_{1-4}$ alkyloxy,
$C_{1-8}$ alkylaminocarbonylmethyleneoxy, or
$C_{1-8}$ dialkylaminocarbonylmethyleneoxy, where m and n are integers 0–6.

In a subclass of the class of compounds described above are compounds of the formula

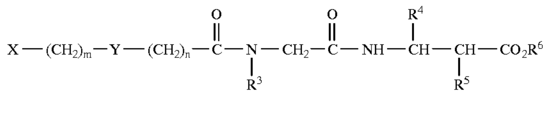

and pharmaceutically acceptable salts thereof, wherein

X is

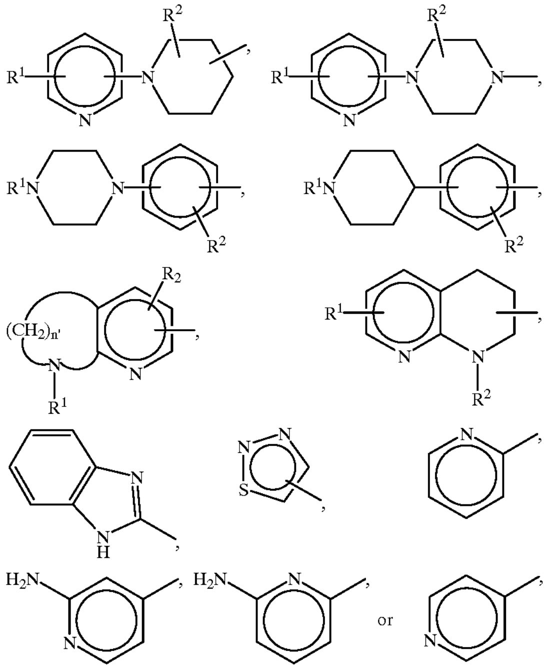

or wherein n' is 2 or 3, and wherein $R^1$ and $R^2$ are independently selected from the group consisting of hydrogen, F, Cl, Br, I,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino,
$C_{1-6}$ alkylamino $C_{1-8}$ alkyl,
$C_{1-6}$ dialkylamino,
$C_{1-6}$ dialkylamino $C_{1-8}$ alkyl,
$C_{1-4}$ alkoxy,
$C_{1-4}$ alkoxy $C_{1-6}$ alkyl,
carboxy,
carboxy $C_{1-6}$ alkyl,
$C_{1-3}$ alkoxycarbonyl,
$C_{1-3}$ alkoxycarbonyl $C_{1-6}$ alkyl,
carboxy $C_{1-6}$ alkyloxy and
hydroxy,
hydroxy $C_{1-6}$ alkyl;

Y is $-(CH_2)_{0-6}-$, $-C\equiv C-$,

-continued

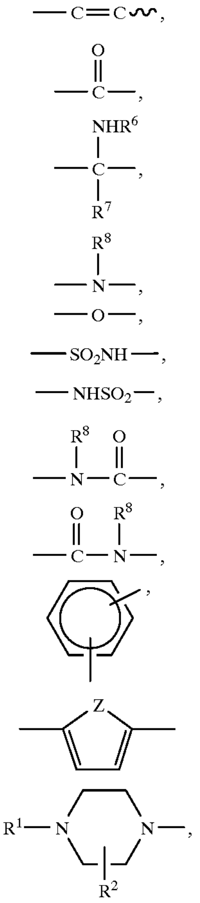

or

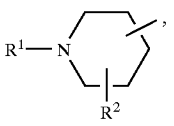

where Z is O, $NR^8$, or S; and $R^8$ is defined as $R^1$ above; $R^3$ and $R^4$ are independently hydrogen, a five or six membered mono or polycyclic aromatic ring system containing 0, 1, 2, 3, or 4 heteroatoms selected from nitrogen, oxygen and sulfur, either unsubstituted or substituted, with one or more groups selected from hydroxyl, halogen, cyano, trifluoromethyl, $C_{1-3}$ alkoxy, $C_{1-5}$ alkylcarbonyloxy, $C_{1-5}$ alkoxycarbonyl, $C_{1-5}$ alkyl, amino$C_{1-5}$ alkyl, hydroxycarbonyl, hydroxycarbonyl$C_{1-5}$ alkyl, or hydroxycarbonyl$C_{1-5}$ alkoxy, —$(CH_2)_n$-aryl, wherein n=1–4 and aryl is defined as a five or six membered mono or polycyclic aromatic ring system containing 0, 1, 2, 3, or 4 heteroatoms selected from nitrogen, oxygen and sulfur, either unsubstituted or substituted, with one or more groups selected from hydroxyl, halogen, cyano, trifluoromethyl, $C_{1-3}$ alkoxy, $C_{1-5}$ alkylcarbonyloxy, $C_{1-5}$ alkoxycarbonyl, $C_{1-5}$ alkyl, amino$C_{1-5}$ alkyl, hydroxycarbonyl, hydroxycarbonyl$C_{1-5}$ alkyl, or hydroxycarbonyl$C_{1-5}$ alkoxy, halogen, hydroxyl, $C_{1-5}$alkylcarbonylamino, aryl$C_{1-5}$ alkoxy, $C_{1-5}$ alkoxycarbonyl, aminocarbonyl, $C_{1-5}$ alkylaminocarbonyl, $C_{1-5}$ alkylcarbonyloxy, $C_{3-8}$ cycloalkyl, oxo, amino, $C_{1-3}$ alkylamino, amino$C_{1-3}$ alkyl, arylaminocarbonyl, aryl$C_{1-5}$alkylaminocarbonyl, aminocarbonyl-$C_{1-4}$ alkyl, hydroxycarbonyl, hydroxycarbonyl $C_{1-5}$ alkyl, $C_{1-6}$alkyl, either unsubstituted or substituted, with one or more groups selected from halogen, bydroxyl, $C_{1-5}$alkylcarbonylamino, aryl$C_{1-5}$ alkoxy, $C_{1-5}$ alkoxycarbonyl, aminocarbonyl, $C_{1-5}$ alkylaminocarbonyl, $C_{1-5}$ alkylcarbonyloxy, $C_{3-8}$ cycloalkyl, oxo, amino, $C_{1-3}$ alkylamino, amino$C_{1-3}$ alkyl, arylaminocarbonyl, aryl$C_{1-5}$alkylaminocarbonyl, aminocarbonyl-$C_{1-4}$ alkyl, hydroxycarbonyl, or hydroxycarbonyl $C_{1-5}$ alkyl, provided that the carbon atom to which $R^3$ and $R^4$ are attached bears only one heteroatom, —$(CH_2)_m$ C≡CH, —$(CH_2)_m$ C≡C—$C_{1-6}$ alkyl, —$(CH_2)_m$ C≡C—$C_{3-7}$cycloalkyl, —$(CH_2)_m$ C—C-aryl, —$(CH_2)_m$ C≡C—$C_{1-6}$ alkyl aryl, —$(CH_2)_m$ CH=$CH_2$, —$(CH_2)_m$ CH=CH $C_{1-6}$ alkyl, —$(CH_2)_m$ CH=CH—$C_{3-7}$cycloalkyl, —$(CH_2)_m$ CH=CH aryl, —$(CH_2)_m$ CH=CH $C_{1-6}$ alkyl aryl, —$(CH_2)_m$ $SO_2C_{1-6}$alkyl, or —$(CH_2)_m$ $SO_2C_{1-6}$ alkylaryl;

$R^5$ is hydrogen, fluorine, $C_{1-8}$ alkyl, hydroxyl, hydroxy $C_{1-6}$ alkyl, carboxy, carboxy $C_{1-6}$ alkyl, $C_{1-6}$ alkyloxy.

$C_{3-8}$ cycloalkyl, aryl $C_{1-6}$ alkyloxy, aryl $C_{1-6}$ alkyl, $C_{1-6}$ alkylcarbonyloxy, amino $C_{1-6}$ alkyl, amino, $C_{1-6}$ alkylamino, $C_{1-6}$ alkylamino $C_{1-6}$ alkyl, aryl amino $C_{1-6}$ alkyl,
aryl amino,
aryl $C_{1-6}$ alkylamino,
aryl $C_{1-6}$ alkylamino $C_{1-6}$ alkyl,
aryl,
aryl $C_{1-6}$ alkylcarbonyloxy,
$C_{1-6}$ dialkylamino,
$C_{1-6}$ dialkylamino $C_{1-6}$ alkyl,
$C_{1-6}$ alkylaminocarbonyloxy,
$C_{1-8}$ alkylsulfonylamino,
$C_{1-8}$ alkylsulfonylamino $C_{1-6}$ alkyl,
aryl sulfonylamino $C_{1-6}$ alkyl,
aryl sulfonylamino,
aryl $C_{1-6}$ alkylsulfonylamino,
aryl $C_{1-6}$ alkylsulfonylamino $C_{1-6}$ alkyl,
$C_{1-8}$ alkyloxycarbonylamino,
$C_{1-8}$ alkyloxycarbonylamino $C_{1-8}$ alkyl,
aryl oxycarbonylamino $C_{1-8}$ alkyl,
aryl oxycarbonylamino,
aryl $C_{1-8}$ alkyloxycarbonylamino,
aryl $C_{1-8}$ alkyloxycarbonylamino $C_{1-8}$ alkyl,
$C_{1-8}$ alkylcarbonylamino,
$C_{1-8}$ alkylcarbonylamino $C_{1-6}$ alkyl,
aryl carbonylamino $C_{1-6}$ alkyl,
aryl carbonylamino,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
aminocarbonylamino,
$C_{1-8}$ alkylaminocarbonylamino,
$C_{1-8}$ alkylaminocarbonylamino $C_{1-6}$ alkyl,
aryl aminocarbonylamino $C_{1-6}$ alkyl,
aryl aminocarbonylamino,
aryl $C_{1-8}$ alkylaminocarbonylamino,
aryl $C_{1-8}$ alkylaminocarbonylamino $C_{1-6}$ alkyl,
aminosulfonylamino $C_{1-6}$ alkyl,
aminosulfonylamino,
$C_{1-8}$ alkylaminosulfonylamino,
$C_{1-8}$ alkylaminosulfonylamino $C_{1-6}$ alkyl,
aryl aminosulfonylamino $C_{1-6}$ alkyl,
aryl aminosulfonylamino,
aryl $C_{1-8}$ alkylaminosulfonylamino,
aryl $C_{1-8}$ alkylaminosulfonylamino $C_{1-6}$ alkyl,
$C_{1-6}$ alkylsulfonyl,
$C_{1-6}$ alkylsulfonyl $C_{1-6}$alkyl,
aryl sulfonyl $C_{1-6}$alkyl,
aryl sulfonyl,
aryl $C_{1-6}$ alkylsulfonyl,
aryl $C_{1-6}$ alkylsulfonyl $C_{1-6}$alkyl,
$C_{1-6}$ alkylcarbonyl,
$C_{1-6}$ alkylcarbonyl $C_{1-6}$ alkyl,
aryl carbonyl $C_{1-6}$alkyl,
aryl carbonyl,
aryl $C_{1-6}$ alkylcarbonyl,
aryl $C_{1-6}$ alkylcarbonyl $C_{1-6}$alkyl,
$C_{1-6}$ alkylthiocarbonylamino,
$C_{1-6}$ alkylthiocarbonylamino $C_{1-6}$ alkyl,
aryl thiocarbonylamino $C_{1-6}$ alkyl,
aryl thiocarbonylamino,
aryl $C_{1-6}$ alkylthiocarbonylamino,
aryl $C_{1-6}$ alkylthiocarbonylamino $C_{1-6}$ alkyl,
aminocarbonyl $C_{1-6}$ alkyl,
aminocarbonyl,
$C_{1-8}$ alkylaminocarbonyl,
$C_{1-8}$ alkylaminocarbonyl $C_{1-6}$ alkyl,
aryl aminocarbonyl $C_{1-6}$ alkyl,
aryl aminocarbonyl,
aryl $C_{1-8}$ alkylaminocarbonyl, or
aryl $C_{1-8}$ alkylaminocarbonyl $C_{1-6}$ alkyl, wherein alkyl groups and aryl groups may be unsubstituted or substituted with one or more substituents selected from $R^1$ and $R^2$; and $R^6$ and $R^7$ are independently hydrogen,
$C_{1-8}$ alkyl,
aryl,
aryl $C_{1-8}$ alkyl,
hydroxy,
$C_{1-8}$ alkyloxy,
aryl oxy,
aryl $C_{1-6}$ alkyloxy,
$C_{1-8}$ alkylcarbonyloxy $C_{1-4}$ alkyloxy,
aryl $C_{1-8}$ alkylcarbonyloxy $C_{1-4}$ alkyloxy,
$C_{1-8}$ alkylaminocarbonylmethyleneoxy, or
$C_{1-8}$ dialkylaminocarbonylmethyleneoxy, where m and n are integers 0–6.

In a group of the subclass are compounds having the formula

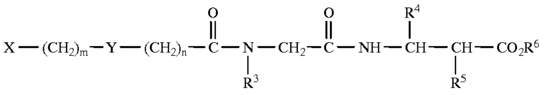

and pharmaceutically acceptable salts thereof, wherein X is

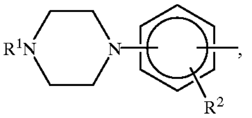

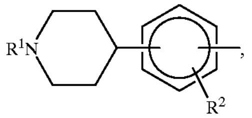

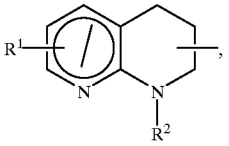

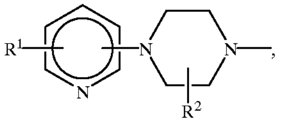

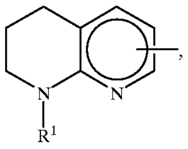

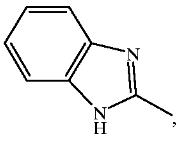

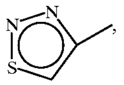

-continued

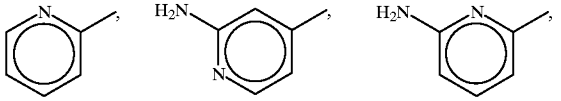

or

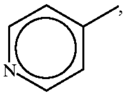

wherein $R^1$ and $R^2$ are independently selected from the group consisting of hydrogen or amino, amino $C_{1-8}$ alkyl;

Y is $-(CH_2)_{0-4}-$,

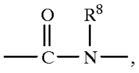

—O—, or

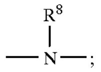

$R^8$ is hydrogen or aryl $C_{0-8}$ alkyl;

$R^3$ is hydrogen, a six membered monocyclic aromatic ring system, either unsubstituted or substituted, with one or more groups selected from hydroxyl, halogen, cyano, trifluoromethyl, $C_{1-3}$ alkoxy, $C_{1-5}$ alkylcarbonyloxy, $C_{1-5}$ alkoxycarbonyl, $C_{1-5}$ alkyl, amino$C_{1-5}$ alkyl, hydroxycarbonyl, hydroxycarbonyl$C_{1-5}$ alkyl, or hydroxycarbonyl$C_{1-5}$ alkoxy, $-(CH_2)_n$-aryl, wherein n=1–4 and aryl is defined as a six membered monocyclic aromatic ring system, either unsubstituted or substituted, with one or more groups selected from hydroxyl, halogen, cyano, trifluoromethyl, $C_{1-3}$ alkoxy, $C_{1-5}$ alkylcarbonyloxy, $C_{1-5}$ alkoxycarbonyl, $C_{1-5}$ alkyl, amino$C_{1-5}$ alkyl, hydroxycarbonyl, hydroxycarbonyl$C_{1-5}$ alkyl, or hydroxycarbonyl$C_{1-5}$ alkoxy, $C_{3-8}$ cycloalkyl, or $C_{1-6}$alkyl, either unsubstituted or substituted, with $C_{3-8}$ cycloalkyl;

$R^4$ is hydrogen, $-(CH_2)_n$-aryl, wherein n=0–4 and aryl is defined as a six membered monocyclic aromatic ring system, either unsubstituted or substituted, with one or more groups selected from hydroxyl, halogen, cyano, trifluoromethyl, $C_{1-3}$ alkoxy, $C_{1-5}$ alkylcarbonyloxy, $C_{1-5}$ alkoxycarbonyl, $C_{1-5}$ alkyl, amino$C_{1-5}$ alkyl, hydroxycarbonyl$C_{0-5}$ alkyl, or hydroxycarbonyl$C_{1-5}$ alkoxy, $C_{1-6}$alkyl, or $-(CH_2)_{0-4}$ C≡CH;

$R^5$ is hydrogen, aryl sulfonylamino $C_{1-6}$ alkyl, aryl sulfonylamino, aryl $C_{1-6}$ alkylsulfonylamino, aryl $C_{1-6}$ alkylsulfonylamino $C_{1-6}$ alkyl, $C_{1-8}$ alkylsulfonylamino, $C_{1-8}$ alkylsulfonylamino $C_{1-6}$ alkyl, aryl sulfonylamino $C_{1-6}$ alkyl, aryl sulfonylamino, aryl $C_{1-6}$ alkylsulfonylamino, aryl $C_{1-6}$ alkylsulfonylamino $C_{1-6}$ alkyl, aminosulfonylamino $C_{1-6}$ alkyl, aminosulfonylamino, $C_{1-8}$ alkylaminosulfonylamino, $C_{1-8}$ alkylaminosulfonylamino $C_{1-6}$ alkyl, aryl aminosulfonylamino $C_{1-6}$ alkyl, aryl aminosulfonylamino, aryl $C_{1-8}$ alkylaminosulfonylamino, aryl $C_{1-8}$ alkylaminosulfonylamino $C_{1-6}$ alkyl, $C_{1-6}$ alkylsulfonyl, $C_{1-6}$ alkylsulfonyl $C_{1-6}$alkyl, aryl sulfonyl $C_{1-6}$alkyl, aryl sulfonyl, aryl $C_{1-6}$ alkylsulfonyl, aryl $C_{1-6}$ alkylsulfonyl $C_{1-6}$alkyl, wherein alkyl groups and aryl groups may be unsubstituted or substituted with one or more substituents selected from R1 and R2;

$R^6$ is hydrogen, $C_{1-8}$ alkyl, or aryl, aryl $C_{1-8}$ alkyl;

m is an integer selected from 0 to 6; and n is an integer selected from 0 to 6.

In a subgroup of the group are compounds having the formula

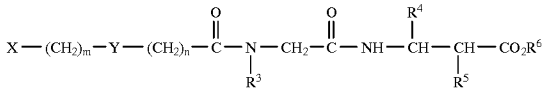

and pharmaceutically acceptable salts thereof, wherein

X is

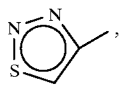

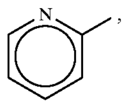

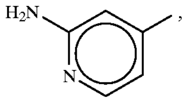

-continued

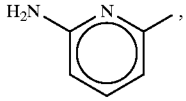,

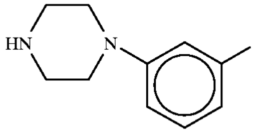,

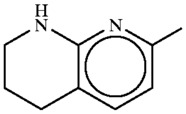;

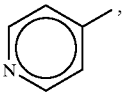,

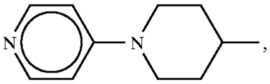,

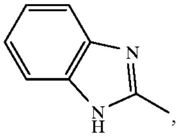, or

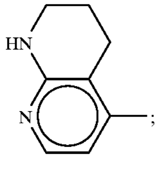;

Y is $-(CH_2)_{0-4}-$,

—O—,

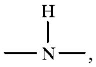, or

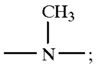;

$R^3$ is hydrogen, methyl,

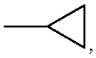, or

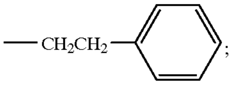;

$R^4$ is hydrogen, methyl,

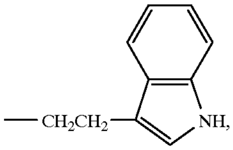,

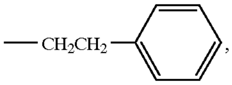,

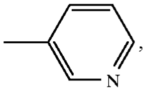,

—≡CH;

$R^5$ is hydrogen, or

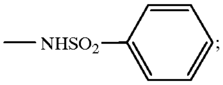;

$R^6$ is hydrogen, methyl, ethyl, or t-butyl;

m is an integer selected from 0 to 6; and n is an integer selected from 0 to 6.

Specific examples of this subgroup include 4-(2-Aminothiazol-4-yl)butanoyl-glycyl-2(S)-phenylsulfonamido-β-alanine t-butyl ester 4-(2-Aminothiazol -4-yl)butanoyl-glycyl-2(S)-phenylsulfonamido-β-alanine 4-(2-Aminothiazol-4-yl)butanoyl-glycyl-3(R)-(2-phenethyl)-β-alanine methyl ester 4-(2-Aminothiazol-4-yl)butanoyl-glycyl-3(R)-(2-phenethyl)-β-alanine trifluoroacetate salt 5-(2-Pyridylamino)pentanoylglycyl-2(S)-phenylsulfonamido-β-alanine ethyl ester 5-(2-Pyridylamino)pentanoylglycyl-2(S)-phenylsulfonamido-β-alanine trifluoroacetate salt 4-(2-Bocamino-pyridin-6-yl)butanoyl-sarcosine-3(R)-[(2-indol-3-yl)ethyl]-β-alanine ethyl ester 4-(2-Aminopyridin-6-yl)butanoyl-sarcosine-3(R)-[(2-indol-3-yl)ethyl]-β-alanine 4-(2-Boc-aminopyridin-6-yl)butanoyl -glycyl-2(S)-phenylsulfonamido-β-alanine t-butyl ester 4-(2-Aminopyridin-6-yl)butanoyl-glycyl-2(S)-phenylsulfonamido-β-alanine 4-(Pyridin-4-yl)butanoyl-sarcosine-3(R)-[2-(indol-3-yl) ethyl]-β-alanine ethyl ester 4-(Pyridin-4-yl)butanoyl-sarcosine-3(R)-[2-(indol-3-yl) ethyl]-β-alanine 4-(2-Bocamino-pyridin-6-yl)butanoyl-N-cyclopropylglycyl-3(R)-(2-phenethyl)-β-alanine ethyl ester 4-(2-Amino-pyridin-6-yl)butanoyl-N-cyclopropylglycyl-3 (R)-(2-phenethyl)-β-alanine ethyl ester hydrochloride 4-(2-Amino-pyridin-6-yl)butanoyl-N-cyclopropylglycyl-3 (R)-(2-phenethyl)-β-alanine 4-(2-Boc-amino-pyridin-6-yl)butanoyl-N-cyclopropylglycyl-3(R)-[(2-indol-3-yl)ethyl]-β-alanine 4-(2-Amino-pyridin-6-yl)butanoyl-N-cyclopropylglycyl-3(R)-[(2-indol-3-yl)ethyl]-β-alanine 4-(2-Bocamino-pyridin-6-yl)butanoyl-N-cyclopropylglycyl-3(R)-methyl-β-alanine ethyl ester 4-(2-Amino-pyridin-6-yl)butanoyl-N-cyclopropylglycyl-3(R)-methyl -β-alanine ethyl ester 4-(2-Amino-pyridin-6-yl)butanoyl-N-cyclopropylglycyl-3(R)-methyl-β-alanine 4-(Pyridin-4-yl)butanoyl-N-(2-phenylethyl)glycyl-3(R)-(2-phenethyl)-β-alanine ethyl ester 4-(Pyridin-4-yl)butanoyl-N-(2-phenyl)glycyl-3(R)-(2-phenethyl)-β-alanine 4-(2-BOC-Aminopyridin-4-yl)butanoyl-N-(2-phenethyl)glycyl-3(R)-methyl-β-alanine benzyl ester 4-(2-BOC-Aminopyridin-4-yl)butanoyl-N-(2-phenethyl)glycyl -3(R)-methyl-β-alanine 4-(2-Aminopyridin-4-yl)butanoyl-N-(2-phenethyl)glycyl-3(R)-methyl-β-alanine 4-(Pyridyloxy)butyrate-N-(2-phenethyl)glycyl-3 (R)-2-phenethyl-β-alanine ethyl ester 4-(Pyridyloxy)butyrate-N-(2-phenethyl)glycyl-3(R)-2-phenethyl-β-alanine 3-[(N-Methyl)-N-(4-pyridyl)]aminopropionyl-sarcosine-3(R)-(2-phenethyl)-β-alanine ethyl ester 3-[(N-Methyl)-N-(4-pyridyl)]aminopropionyl-sarcosine-3(R)-(2-henethyl)-β-alanine N-{N'-3-(4-t-Butoxycarbonyl-1-piperizinyl)benzoyl)glycy}-3(R)-methyl-β-alanine benzyl ester N-[N'-[3-(1-Piperazinyl)benzoyl]glycyl]-3(R)-methyl-β-alanine trifluoroacetic acid salt N-[N'-[3-(4-t-Butoxycarbonyl-1-piperazinyl)benzoyl]glycyl]-3(R)-(2-phenethyl)-β-alanine methyl ester N-[N'-[3-(1-Piperazinyl)benzoyl]glycyl]-3(R)-(2-phenethyl)-β-alanine trifluoroacetic acid salt N-[N'-[3-(4-t-Butoxycarbonyl-1-piperazinyl)benzoyl]-N'-(2-phenethyl)glycyl]-3(R)-(2-phenethyl)-β-alanine methyl ester N-[N'-[3-(1-Piperazinyl)benzoyl]-N -(2-phenethyl)glycyl]-3(R)-(2-phenethyl)-β-alanine trifluoroacetic acid salt 4-(1,2,3,4-Tetrahydro-1,8-naphthyridin-7-yl)butanol-glycyl-β-alanine t-butyl ester 4-(1,2,3,4-Tetrahydro-1,8-naphthyridin-7-yl)butanoyl-glycyl-β-alanine 4-(1,2,3,4-Tetrahydro-1,8-naphthyridin-7-yl)butanoyl-glycyl-3(S)-pyridin-3-yl-β-alanine ethyl ester 4-(1,2,3,4-Tetrahydro-1,8-naphthyridin-7-yl)butanoyl-glycyl-3(S)pyridin-3-yl-β-alanine Ethyl N-pyridin-4-ylisonipecotyl-N-cyclopropylglycine-3(S)-ethynyl-β-alanine N-Pyridin-ylisonipecotyl-N-cyclopropylglycine-3(S)-ethynyl-β-alanine Ethyl N-pyridin-4-ylnipecotyl-N-cyclopropylglycine-3(S)-ethynyl-β-alanine N-Pyridin-4-ylnipecotyl -N-cyclopropylglycine-3(S)-ethynyl-β-alanine 4-(1,2,3,4-Tetrahydro-1,8-naphthyridin-5-yl)butanoyl-N-(cyclo-propyl)gly-3(S)ethynyl-β-alanine ethyl ester 4-(1,2,3,4-Tetrahydro-1,8-naphthyridin-5-yl)butanoyl-N-(cyclo-propyl)glycyl-3(S)-ethynyl-β-alanine, 3-{2-[5-(1H-Benzoimidazol-2-yl-amino)-pentanoylamino]-acetylamino}-3(S)-pyridin-3-yl-propionic acid, and phannaceutically acceptable salts, such as the trifluoroacetate salt and the hydrochloric acid salt.

Compounds of the invention are also useful for inhibiting the bone resorption activity of mammalian osteoclast cells by administering a pharmacologically effective amount of the compound to a patient in need of such activity to inhibit the activity of mammalian osteoclasts.

Compounds of the invention are also useful for inhibiting tumor growth in mammals. Pharmacologically effective amounts of the compounds, including pharamaceutically acceptable salts thereof, are administered to the mammal, to inhibit tumor growth. The growth of tumors depends on an adequate blood supply, which in turn depends on growth of new vessels into the tumor. New vessels are stimulated by factors secreted by the tumor. Inhibition of angiogenesis can cause tumor regression in animals.

Compounds of the invention are also useful for treating and preventing diabetic retinopathy in mammals. Pharmacologically effective amounts of the compounds, including pharamaceutically acceptable salts thereof, are administered to the mammal, to inhibit diabetic retinopathy.

Compounds are also useful in the prevention of restenosis of vessels.

The term "bone resorption activity" means the process by which osteoclasts solubilize bone minerals and increase the activity of enzymes that degrade bone matrix.

Compounds of the invention are useful for inhibiting the binding of fibrinogen to blood platelets and for inhibiting the aggregation of blood platelets. The above-mentioned compounds can be used in a method of acting upon a fibrinogen receptor which comprises administering a therapeutically effective but non-toxic amount of such compound to a mammal, preferably a human. A pharmaceutical composition comprising a pharmaceutically acceptable carrier and, dispersed therein, an effective but non-toxic amount of such compound is another feature of this invention.

The invention also includes the use of a compound of the invention, or a pharmaceutically acceptable salt thereof, in the manufacture of a medicament for inhibiting the aggregation of blood platelets, preventing platelet thrombosis, preventing thromboembolism or preventing reocclusion, in a mammal.

DETALED DESCRIPTION OF THE INVENTION

Fibrinogen receptor antagonist compounds of Formula I are useful in a method of inhibiting the binding of fibrinogen to blood platelets and for inhibiting the aggregation of blood platelets. Fibrinogen receptor antagonists of this invention are illustrated by compounds having the formula:

The following compounds were tested and found to inhibit platelet aggregation with $IC_{50}$ values between about 0.01 $\mu$M and 100 $\mu$M.

4-(2-Aminothiazol-4-yl)butanoyl-glycyl-2(S)-phenylsulfonamido-β-alanine t-butyl ester 4-(2-Aminothiazol-4-yl)butanoyl-glycyl-2(S)-phenylsulfonamido-β-alanine 4-(2-Aminothiazol-4-yl)butanoyl-glycyl-3(R)-(2-phenethyl)-β-alanine methyl ester 4-(2-Aminothiazol-4-yl)butanoyl-glycyl-3(R)-(2-phenethyl)-β-alanine trifluoroacetate salt 5-(2-Pyridylamino)pentanoylglycyl -2(S)-phenylsulfonamido-β-alanine ethyl ester 5-(2-Pyridylamino)pentanoylglycyl -2(S)-phenylsulfonamido-β-alanine trifluoroacetate salt 4-(2-Bocamino-pyridin-6-yl)butanoyl-sarcosine-3(R)-[(2-indol -3-yl)ethyl]-β-alanine ethyl ester 4-(2-Aminopyridin-6-yl)butanoyl-sarcosine-3(R)-[(2-indol-3-yl)ethyl]-β-alanine 4-(2-Boc-aminopyridin-6-yl)butanoyl-glycyl-2(S)-phenylsulfonamido-β-alanine t-butyl ester 4-(2-Aminopyrdin-6-yl)butanoyl-glycyl-2(S)-phenylsulfonamido-β-alanine 4-(Pyridin-4-yl)butanoyl-sarcosine-3(R)-[2-(indol-3-yl)ethyl]-β-alanine ethyl ester 4-(Pyridin-4-yl )butanoyl-sarcosine-3 (R)-[2-(indol -3-yl) ethyl]-β-alanine 4-(2-Bocamino-pyridin-6-yl)butanoyl-N-cyclopropylglycyl-3(R)-(2-phenethyl)-β-alanine ethyl ester 4-(2-Amino-pyridin-6-yl)butanoyl-N-cyclopropylglycyl-3 (R)-(2-phenethyl)-β-alanine ethyl ester hydrochloride 4-(2-Amino-pyridin-6-yl)butanoyl-N-cyclopropylglycyl-3 (R)-(2-phenethyl)-β-alanine 4-(2-Boc-amino-pyridin-6-yl)butanoyl-N-cyclopropylglycyl-3(R)-[(2-indol-3-yl)ethyl]-β-alanine 4-(2-Amino-pyridin-6-yl)butanoyl-N-cyclopropylglycyl-3 (R)-[(2-indol-3-yl)ethyl]-β-alanine 4-(2-Bocamino-pyridin-6-yl)butanoyl-N-cyclopropylglycyl-3(R)-methyl-β-alanine ethyl ester 4-(2-Amino-pyridin-6-yl)butanoyl-N-cyclopropylglycyl-3 (R)-methyl-β-alanine ethyl ester 4-(2-Amino-pyridin-6-yl)butanoyl-N-cyclopropylglycyl-3 (R)-methyl-β-alanine 4-(Pyridin-4-yl)butanoyl-N-(2-phenylethyl)glycyl-3(R)-(2-phenethyl)-β-alanine ethyl ester 4-(Pyridin-4-yl)butanoyl-N-(2-phenyl)glycyl-3(R)-(2-phenethyl)-β-alanine 4-(2-BOC-Aminopyridin-4-yl)butanoyl-N-(2-phenethyl) glycyl -3(R)-ethyl-β-alanine benzyl ester 4-(2-BOC-Aminopyridin-4-yl)butanoyl-N-(2-phenethyl) glycyl-3(R)-methyl-β-alanine 4-(2-Aminopyridin-4-yl)butanoyl-N-(2-phenethyl)glycyl-3 (R)-methyl-β-alanine 4-(Pyridyloxy)butyrate-N-(2-phenethyl)glycyl-3(R)-2-phenethyl-β-alanine ethyl ester 4-(Pyridyloxy)butyrate-N-(2-phenethyl)glycyl-3(R)-2-phenethyl-β-alanine 3-[(N-Methyl)-N-(4-pyridyl)]aminopropionyl-sarcosine-3 (R)-(2-phenethyl)-β-alanine ethyl ester 3-[(N-Methyl)-N-(4-pyridyl)]aminopropionyl-sarcosine-3 (R)-(2-phenethyl)-β-alanine N-{N'-3-(4-t-Butoxycarbonyl-1-piperizinyl)benzoyl) glycyl}-3(R)-methyl-β-alanine benzyl ester N-[N'-[3-(1-Piperazinyl)benzoyl]glycyl]-3(R)-methyl-β-alanine trifluoroacetic acid salt N-[N'-[3-(4-t-Butoxycarbonyl-1-piperazinyl)benzoyl] glycyl]-3(R)-(2-phenethyl)-β-alanine methyl ester N-[N'-[3-(1-Piperazinyl)benzoyl]glycyl]-3(R)-(2-phenethyl)-β-alanine trifluoroacetic acid salt N-[N'-[3-(4-t-Butoxycarbonyl-1-piperazinyl)benzoyl]-N'-(2-phenethyl)glycyl]-β(R)-(2-phenethyl)-β-alanine methyl ester N-[N'-[3-(1-Piperazinyl)benzoyl]-N'-(2-phenethyl)glycyl]-3(R)-(2-phenethyl)-β-alanine trifluoroacetic acid salt 4-(1,2,3,4-Tetrahydro-1,8-naphthyridin-7-yl)butanol-glycyl-β-alanine t-butyl ester 4-(1,2,3,4-Tetrahydro-1,8-naphthyridin-7-yl)butanoyl-glycyl-β-alanine 4-(1,2,3,4-Tetrahydro-1,8-naphthyridin-7-yl)butanoyl-glycyl-3(S)-pyridin-3-yl-β-alanine ethyl ester 4-(1,2,3,4-Tetrahydro-1,8-naphthyridin-7-yl)butanoyl-glycyl-3(S)pyridin-3-yl-β-alnine Ethyl N-pyridin-4-ylisonipecotyl-N-cyclopropylglycyl-3 (S)-ethynyl-β-alanine N-Pyridin-ylisonipecotyl-N-cyclopropylglycyl-3(S)-ethynyl-β-alanine Ethyl N-pyridin-4-ylnipecotyl-N-cyclopropylglycyl-3(S)-ethynyl-β-alanine N-Pyridin-4-ylnipecotyl-N-cyclopropylglycyl-3(S)-ethynyl-β-alanine 4-(1,2,3,4-Tetrahydro-1,8-naphthyridin-5-yl )butanoyl-N-(cyclo-propyl)glycyl-3(S)ethynyl-β-alanine ethyl ester 4-(1,2,3,4-Tetrahydro-1,8-naphthyridin-5-yl)butanoyl-N-(cyclo-propyl)glycyl-3(S)-ethynyl-β-alanine.

One test which is used to evaluate fibrinogen receptor antagonist activity is based on evaluation of inhibition of ADP-stimulated platelets. Aggregation requires that fibrinogen bind to and occupy the platelet fibrinogen receptor site. Inhibitors of fibrinogen binding inhibit aggregation. In the ADP-stimulated platelet aggregation assay used to determine inhibition associated with the compounds claimed in the instant invention, human platelets are isolated from fresh blood, collected into acid citrate/dextrose by differential centrifugation followed by gel filtration on Sepharose 2B in divalent ion-free Tyrode's buffer (pH 7.4) containing 2% bovine serum albumin.

Platelet aggregation is measured at 37° C. in a Chronolog aggregometer. The reaction mixture contains gel-filtered human platelets ($2\times10^8$ per ml), fibrinogen (100 micrograms per ml (ug/ml)), $Ca^{2+}$ (1 mM), and the compound to be tested. The aggregation is initiated by adding 10 mM ADP 1 minute after the other components are added. The reaction is then allowed to proceed for at least 2 minutes. The extent of inhibition of aggregation is expressed as the percentage of the rate of aggregation observed in the absence of inhibitor. The $IC_{50}$ is the dose of a particular compound inhibiting aggregation by 50% relative to a control lacking the compound.

The term "pharmaceutically acceptable salts" shall mean non-toxic salts of the compounds of this invention which are generally prepared by reacting the free base with a suitable organic or inorganic acid. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, trifluoroacetate, and valerate.

Compounds of the present invention are chiral; included within the scope of the present invention are racemic mixtures and separated enantiomers of the general formula. Furthermore, all diastereomers, including E, Z isomers, of the general formula are included in the present scope. Furthermore, hydrates as well as anhydrous compositions and polymorphs of the general formula are within the present invention.

Prodrugs, such as ester derivatives of described compounds, are compound derivatives which, when absorbed into the bloodstream of a warm-blooded animal, cleave in such a manner as to release the drug form and permit the drug to afford improved therapeutic efficacy.

The term "pharmaceutically effective amount" shall mean that amount of a drug or pharmaceutical agent that will elicit the biological or medical response of a tissue, system or animal that is being sought by a researcher or clinician. The term "anti-coagulant" shall include heparin, and warfarin. The term "thrombolytic agent" shall include agents such as streptokinase and tissue plasminogen activator. The term "platelet anti-aggregation agent" shall include agents such as aspirin and dipyridamole.

The term "alkyl" means straight or branched alkane containing 1 to about 10 carbon atoms, e.g., methyl, ethyl, n-propyl, isopropyl, n-butyl, isobutyl, sec-butyl, tert-butyl, pentyl, iso-amyl, hexy, octyl radicals and the like, straight or branched alkene containing 2 to about 10 carbon atoms, e.g., propylenyl, buten-1-yl, isobutenyl, pentenylen-1-yl, 2,2-methylbuten-1-yl, 3-methylbuten-1-yl, hexen-1-yl, hepten-1-yl, and octen-1-yl radicals and the like, or straight or branched alkyne containing 2 to about 10 carbon atoms, e.g., ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "aryl" means a 5- or 6-membered aromatic ring containing 0, 1, or 2 heteroatoms selected from O, N, and S. Examples of aryl include phenyl, pyridine, pyrimidine, imidazole, thiophene, oxazole, isoxazole, thiazole, and amino- and halogen- substituted derivatives thereof.

The terms "alkyloxy" or "alkoxy" include an alkyl portion where alkyl is as defined above. Examples of alkoxy include methyloxy, propyloxy, and butyloxy.

The terms "arylalkyl" and "alkylaryl" include an alkyl portion where alkyl is as defined above and to include an aryl portion where aryl is as defined above. The $C_{0-n}$ or $C_{1-n}$ designation where n may be an integer from 1–10 or 2–10 respectively refers to the alkyl component of the arylalkyl or alkylaryl unit. Examples of arylalkyl include benzyl, fluorobenzyl, chlorobenzyl, phenylethyl, phenylpropyl, fluorophenylethyl, chlorophenylethyl, thienylmethyl, thienylethyl, and thienylpropyl. Examples of alkylaryl include toluene, ethylbenzene, propylbenzene, methylpyridine, ethylpyridine, propylpyridine, butylpyridine, butenylpyridine, and pentenylpyridine.

The term "halogen" includes fluorine, chlorine, iodine and bromine.

The term "oxy" means an oxygen (O) atom. The term "thio" means a sulfur (S) atom. Under standard nonmenclature used throughout this disclosure, the terminal portion of the designated side chain is described first followed by the adjacent functionality toward the point of attachment. For example, a $C_{1-6}$ alkyl substituted with $C_{1-5}$ alkylcarbonylamino is equivalent to

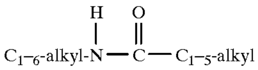

Compounds of the invention where X is a 5-membered monocyclic aromatic ring system, e.g., a thiazole system, can be prepared by forming an alkyl ester substituted derivative of the ring, e.g., methyl 4-(2-aminothiazol-4-yl) butanoate, forming the corresponding acid with HCl, and reacting with an amine to form the final product.

Compounds of the invention where X is a 6-membered monocyclic aromatic ring system, e.g., a pyridine system, can be prepared using 2-aminopyridine, 2-aminopicoline, 4-vinyl pyridine, etc., as described in Schemes 3, 4, and 10.

Compounds of the invention where X is a 9-membered polycyclic aromatic fused ring system can be prepared by reacting a substituted 5-membered ring starting material such as 2-amino-3-bromo thiophene, 2-nitro-3-bromo thiophene, 2-amino-3-bromo pyrrole, and 2-amino-3-bromo furan, with an appropriate compound under suitable ring closure conditions to effect formation of the 9-membered fused ring system.

Compounds of the invention where X is a 10-membered polycyclic aromatic ring system can be prepared using a starting material such as naphthyridin (Hamada, Y. et al., *Chem. Pharm. Bull. Soc.,* 1971, 19(9), 1857–1862), or by reacting an aminoaldehyde pyridine with a suitable ketone under suitable ring closure conditions to effect formation of the 10-membered fused ring system.

The examples illustrate procedures for preparing compounds of the invention where Y is $-(CH_2)_{0-4}-$, —O—, and $-N(R^8)-$. To make compounds where Y is $-N(R^8)C(O)-$, an acid such as compound 1-4 can be subjected to a Curtius reaction to form the amine, and subsequent condensation to give the final product.

In the schemes and examples below, various reagent symbols have the following meanings:

BOC
(or Boc): t-butyloxycarbonyl
Pd-C: Palladium on activated carbon catalyst
DMF: Dimethylformamide
DMSO: Dimethylsulfoxide
CBZ: Carbobenzyloxy
$CH_2Cl_2$: Methylene chloride
$CHCl_3$: chloroform
EtOH: ethanol
MeOH: methanol
EtOAc: ethyl acetate
HOAc: acetic acid
BOP: Benzotriazol-1-yloxytris(dimethylamino) phosphonium, hexafluorophosphate
EDC: 1-(3-Dimethylaminopropyl)-3-ethylcarbodiimide hydrochloride
Oxone: potassium peroxymonosulfate
LDA: Lithium diisopropylamide
PYCLU: Chloro-N,N,N',N'-bis(pentamethylene) formamidinium hexafluorophosphate The compounds of the present invention can be administered in such oral forms as tablets, capsules (each of which includes sustained release or timed release formulations), pills, powders, granules, elixirs, tinctures, suspensions, syrups, and emulsions. Likewise, they may be administered in intravenous (bolus or infusion), intraperitoneal, subcutaneous, or intramusculsar form, all using forms well known to those of ordinary skill in the pharmaceutical arts. An effective but non-toxic amount of the compound desired can be employed as an anti-aggregation agent.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Compounds of this invention may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gp IIb/IIIa on the platelet membranes and fibrinogen adsorbed to the surface of the circuit. (Gluszko et al., *Amer. J. Physiol.,* 252(H), 615–621 (1987)). Platelets released from artificial surfaces show impaired hemostatic function. Compounds of the invention may be administered to prevent adhesion.

Other applications of these compounds include prevention of platelet thrombosis, thromboembolism and reocclusion during and after thrombolytic therapy and prevention of platelet thrombosis, thromboembolism and reocclusion after angioplasty or coronary artery bypass procedures. They may also be used to prevent myocardial infarction.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the present invention, when used for the indicated effects, will range between about 0.01 mg per kg of body weight per day (mg/kg/day) to about 100 mg/kg/day and preferably 0.01–50 mg/kg/day and more preferably 0.01–20 mg/kg/day, e.g. 0.1 mg/kg/day, 1.0 mg/kg/day, 5.0 mg/kg/day, or 10 mg/kg/day. Intravenously, the most preferred doses will range from about 1 to about 10 mg/kg/minute during a constant rate infusion. Advantageously, compounds of the present invention may be administered in divided doses of two, three, or four times daily. Furthermnore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather that intermittent throughout the dosage regime.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidyicholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The compounds of the present invention can also be co-administered with suitable anticoagulation agents or thrombolytic agents such as plasminogen activators or streptokinase to achieve synergistic effects in the treatment of various vascular pathologies. They may also be combined with heparin, aspirin, or warfarin.

The novel compounds of the present invention were prepared according to the procedure of the following examples. The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

SCHEME 1

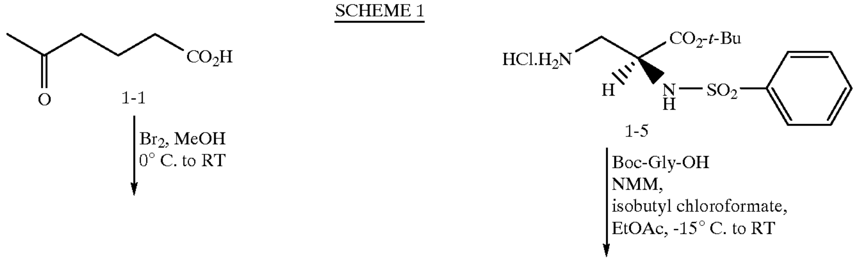

1-1

1-5

-continued

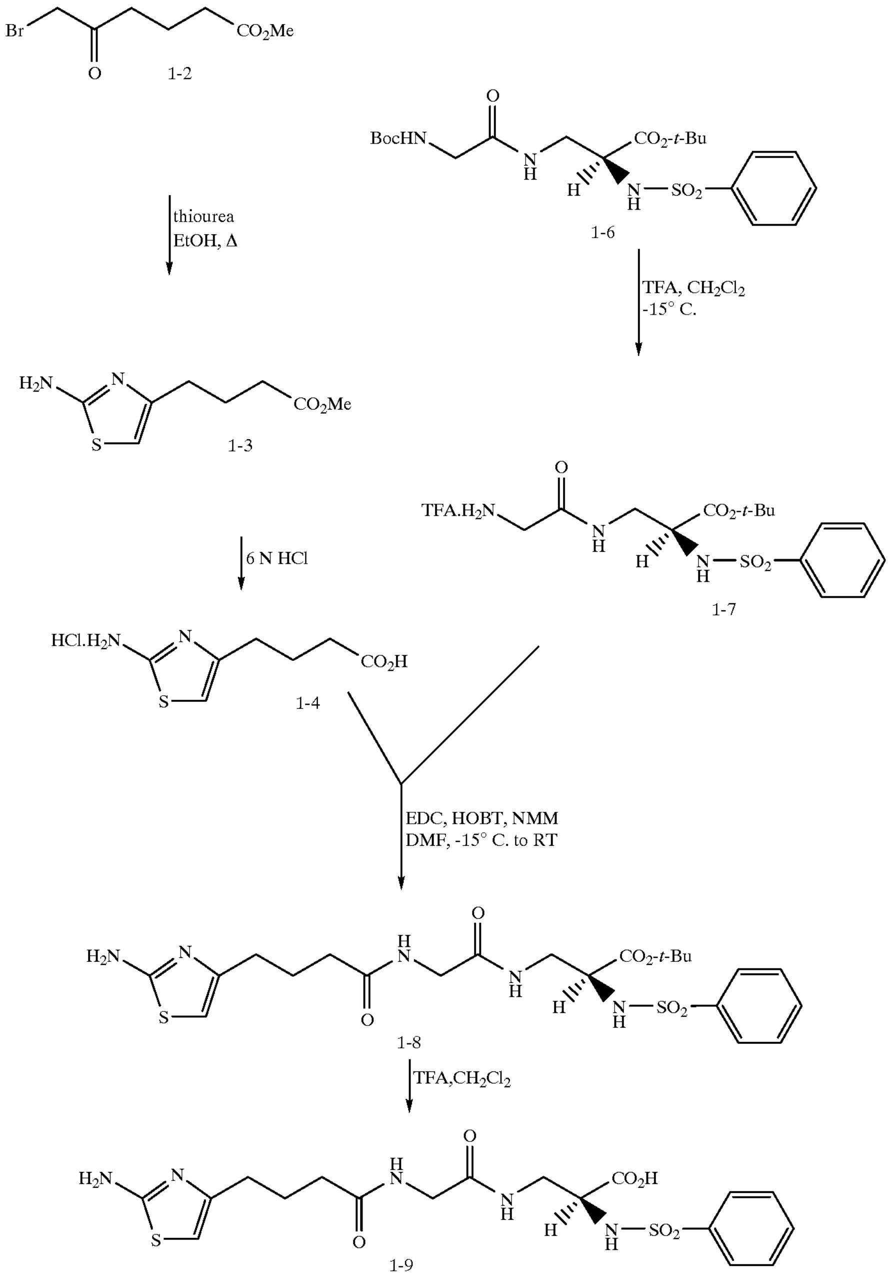

1-2

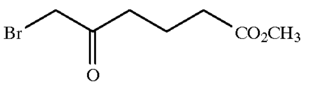

Methyl 6-bromo-5-oxohexanoate (1-2)

5-Oxohexanoic acid (1-1, 5 mL, 42 mmol) was dissolved in 84 mL MeOH and cooled to 0° C. $Br_2$ (2.2 mL, 43 mmol) was added dropwise, and the reaction was stirred at RT overnight. After removing the MeOH by rotary evaporation, the residue was dissolved in ether, washed with water, sat. $NaHCO_3$ and brine, dried ($Na_2SO_4$), filtered and concentrated. Flash chromatography (silica, 10% EtOAc/hexane) provided the bromide-ester 1-2 as a yellow oil.

TLC $R_f$ 0.09 (silica, 15% EtOAc/hexane)

$^1$H-NMR (300 MHz, $CDCl_3$): δ 3.88 (s, 2H), 3.67 (s, 3H), 2.75 (t, J=7 Hz, 2H), 2.37 (t, J=7 Hz, 2H), 1.94 (qn, J=7 Hz, 2H).

1-3

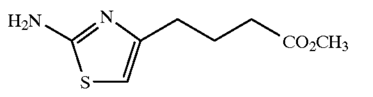

Methyl 4-(2-aminothiazol-4-yl)butanoate (1-3)

Bromide 1-2 (3.45 g, 15.5 mmol) and thiourea (1.4 g, 18 mmol) were combined in 77 mL EtOH and heated to reflux.

After disappearance of 1-2, the EtOH was removed by rotary evaporation and the residue was diluted with EtOAc, washed with water and brine, then dried ($MgSO_4$), filtered and concentrated. The pH of the aqueous phase was adjusted to 7, and the solution was re-extracted with EtOAc (2×). These organic extracts were washed with brine, dried ($MgSO_4$), filtered and concentrated, combined with the first organic residues, then purified by flash chromatography (silica, EtOAc) providing aminothiazole 1-3 as a white solid.
TLC $R_f$ 0.5 (silica, EtOAc)
$^1$H-NMR (400 MHz, $CDCl_3$): δ 6.09 (s, 1H), 5.19 (br s, 2H), 3.66 (s, 3H), 2.55 (t, J=7 Hz, 2H), 2.34 (t, J=7 Hz, 2H), 1.96 (qn, J=7 Hz, 2H).

1-4

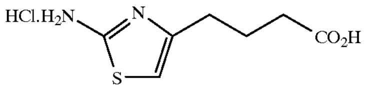

4-(2-Aminothiazol-4-yl)butanoic acid hydrochloride (1-4)

Ester 1-3 (1.3 g, 6.5 mmol) was dissolved in 32 mL 6 N HCl. After stirring overnight, the resulting suspension was concentrated, providing acid 1-4 as a white solid.
$^1$H-NMR (400 MHz, $d_6$-DMSO): δ 9.12 (br s, 1H), 6.51 (s, 1H), 3.50 (br s), 2.51 (t, J=7 Hz, 2H), 2.24 (t, J=7 Hz, 2H), 1.77 (qn, J=7 Hz, 2H).

1-6

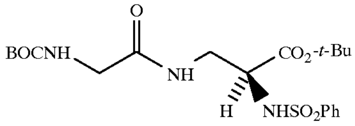

N-Boc-glycyl-2(S)-phenylsulfonamido-β-alanine t-butvl ester (1-6)

N-Boc-glycine (255 mg, 1.5 mmol) was dissolved in 7.4 mL EtOAc, cooled to −15° C., then NMM (179 μL, 1.6 mmol) and isobutyl chloroformate (211 μL, 1.6 mmol) were added. After 20 min, amine 1-5 (500 mg, 1.5 mmol) and additional NMM (422 μL, 3.2 mmol) were added and the reaction was warmed to RT overnight. Following dilution with EtOAc, the mixture was washed with water, sat. $NaHCO_3$, 10% $KHSO_4$, and brine, dried ($MgSO_4$), filtered and concentrated, providing amide 1-6 as a white solid.
TLC $R_f$ 0.73 (silica, EtOAc)
$^1$H-NMR (300 MHz, $CDCl_3$): δ 7.84 (d, J=7 Hz, 2H), 7.59 (ABX t, J=7 Hz, 1H), 7.51 (ABX t, J=7 Hz, 2H), 6.58 (br m, 1H), 5.58 (d, J=8 Hz, 1H), 5.11 (br s, 1H), 3.90–3.78 (m, 3H), 3.72 (m, 1H), 3.40 (m, 1H), 1.48 (s, 9H), 1.28 (s, 9H).

1-7

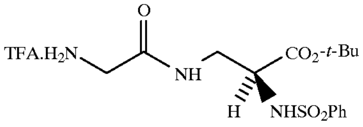

Glycyl-2(S)-phenylsulfonamido-β-alanine t-butyl ester trifluoroacetate salt (1-7)

Protected amide 1-6 (576 mg, 1.26 mmol) was dissolved in 6.3 mL $CH_2Cl_2$, cooled to −15° C., and TFA (6.3 mL) was added. After 25 min the reaction was concentrated, providing amine 1-7.
TLC $R_f$ 0.36 (silica, 9:1:1 $CH_2Cl_2$/MeOH/HOAc).

1-8

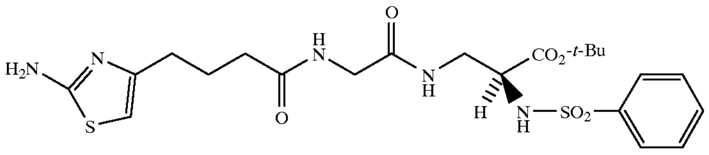

4-(2-Aminothiazol-4-yl)butanoyl-glycyl-2(S)-phenylsulfonamido-β-alanine t-butyl ester (1-8)

Acid 1-4 (300 mg, 1.35 mmol), amine 1-7 (600 mg, 1.37 mmol), HOBT (219 mg, 1.14 mmol) and NMM (445 μL, 4.04 mmol) were combined in 13 mL DMF, cooled to −15° C., and EDC (310 mg, 1.61 mmol) was added. The reaction was warmed to RT, stirred overnight, then diluted with EtOAc, washed with water, sat. $NaHCO_3$, and brine, dried ($MgSO_4$), filtered and concentrated. Flash chromatography (silica, 20% MeOH/EtOAc) provided 1-8 as yellow solid.
TLC $R_f$ 0.55 (silica, 20% MeOH/EtOAc)
$^1$H-NMR (400 MHz, $CDCl_3$): δ 7.80 (d, J=7 Hz, 2H), 7.55 (ABX t, J=7 Hz, 1H), 7.47 (ABX t, J=8 Hz, 2H), 7.35 (br s, 1H), 7.04 (br m, 1H), 6.12 (s, 1H), 5.41 (br s, 2H), 4.05–3.95 (m, 3H), 3.69 (m, 1H), 3.39 (ddd, 1H), 2.70–2.55 (m, 2H), 2.33 (m, 2H), 2.01 (qn, J=7 Hz, 2H), 1.27 (s, 9H).

1-9

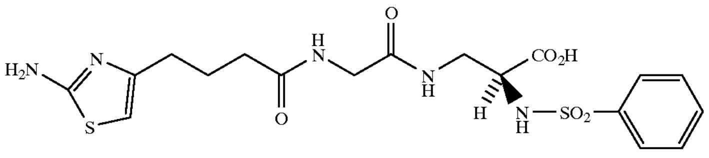

4-(2-Aminothiazol-4-yl)butanoyl-glycyl-2(S)-phenylsulfonamido-β-alanine (1-9)

Ester 1-8 (365 mg, 0.69 mmol) was dissolved in $CH_2Cl_2$ (3.5 mL), then TFA (3.5 mL) was added. After 5 h the reaction mixture was concentrated, azeotroped with toluene, then purified by sequential flash chromatography (silica, 22:20:1:1 EtOAc/EtOH/$H_2O$/$NH_4OH$, then silica, 4:1:1 $CH_2Cl_2$/MeOH/HOAc, then 7:1:1 $CH_2Cl_2$/MeOH/HOAc), providing 1-9 as a white solid.

TLC $R_f$ 0.33 (silica, 7:1:1 $CH_2Cl_2$/MeOH/HOAc)

$^1$H-NMR (400 MHz, $CD_3OD$): δ 7.86 (d, J=7 Hz, 2H), 7.58 (ABX t, J=7 Hz, 1H), 7.52 (ABX t, J=8 Hz, 2H), 6.27 (s, 1H), 3.89 (AB d, J=17 Hz, 1H), 3.77 (AB d, J=17 Hz, 1H), 3.64 (t, J=6 Hz, 1H), 3.53 (AB dd, 1H), 3.41 (AB dd, 1H), 2.57 (t, J=7 Hz, 2H), 2.35–2.25 (m, 2H), 1.95 (m, 2H).

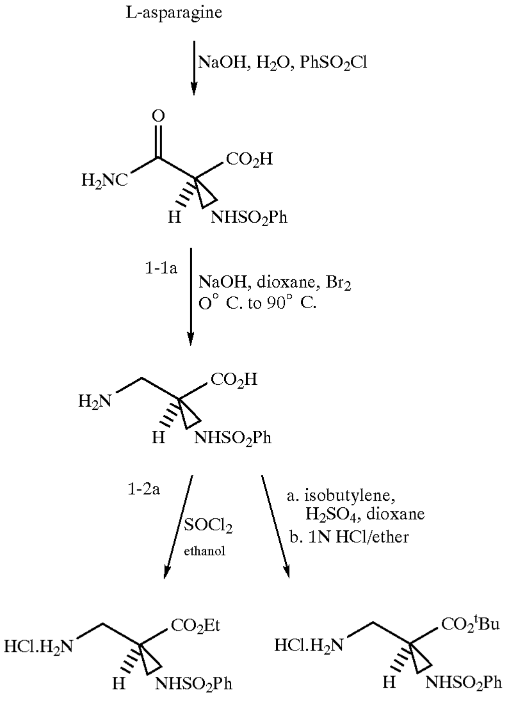

3-4 1-5

N-Phenylsulfonyl-L-asparagine (1-1a)

To a stirred solution of L-asparagine (Aldrich) (10 g, 76 mmol), NaOH (3.4 g, 85 mmol), $H_2O$ (50 mL), and dioxane (50 mL) at 0° C. was added $PhSO_2Cl$ (10.6 mL, 84 mmol). After 1 min, NaOH (3.4 g) in $H_2O$ (50 mL) was added and the reaction mixture stirred for 30 min. The reaction mixture was then concentrated to remove the dioxane then washed with EtOAc. The aqueous phase was then cooled to 0° C. and acidified to pH 5.0 with conc. HCl to effect product precipitation. The resulting solid was collected by filtration, washed with $H_2O$ (20 mL) and dried at 50° C. under vacuum to give N-phenylsulfonyl-L-asparagine (1-1a) as a white solid.

$R_f$ 0.40 (silica, 10:1:1 ethanol/$H_2O$/NH4OH). $^1$H NMR (300 MHz, $D_2O$) δ 7.59 (m, 2H), 7.26 (m, 3H), 3.92 (m, 1H), 3.02 (m, 1H), 2.35 (m, 1H).

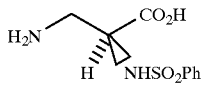

3-Amino-2(S)-phenylsulfonylaminopropionic acid (1-2b)

To stirred solution of NaOH (15.6 g, 0.4 mol) in $H_2O$ (70 mL), cooled with an icebath, was added bromine (3.6 mL, 0.07 mol) dropwise. After 5 min, a cold solution of N-phenylsulfonyl-L-asparagine, 1-1a (14.6 g, 54 mmol) and NaOH (4.3 g, 0.1 mol) in $H_2O$ (50 mL) was added in one portion. The solution was stirred for 20 min at 0° C. then 30 min at 90° C. The reaction mixture was recooled to 0° C., and the pH adjusted to 7 through dropwise addition of conc. HCl. The white precipitate formed was collected by filtration and then dried to give (1-2b) as a white solid. $^1$H NMR (300 MHz, $D_2O$) δ 8.00, 7.50 (m, 5H), 3.88 (m, 1H), 3.37 (m, 1H), 3.12 (m, 1H).

3-4

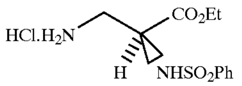

Ethyl 3-Amino-2(S)-phenylsulfonylaminopropionate hydrochloride (3-4)

Amino acid 1-2a (1.0 g, 4.1 mmol) was suspended in 20 mL EtOH, cooled to 0° C., and $SOCl_2$ (1.5 mL, 21 mmol) was added dropwise. After stirring at RT overnight the mixture was concentrated, triturated with $Et_2O$ (2×), and dried, providing 3-4 (1.26 g) as a hygroscopic yellow solid. $^1$H-NMR (300 MHz, $d_6$-DMSO): δ 8.30 (br s), 7.79 (d, J=8 Hz, 2H), 7.70–7.60 (m, 3H), 4.21 (t, J Hz, 1H), 3.90–3.80 (m, 2H), 3.09 (ABX dd, J=13,6Hz, 1H), 2.90 (ABX dd, J=13, 8 Hz, 2H), 0.97 (t, J=7 Hz, 3H).

1-5

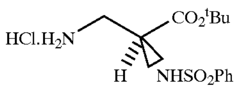

tert-Butyl 3-Amino-2(S)-phenylsulfonylaminopropionate hydro-chloride (1-5)

In a Fischer-Porter tube, a mixture of 1-2a (10.2 g, 42 mmol) and DME (150 mL) was sequentially treated with $H_2SO_4$ (6.4 mL, 0.12 mol), cooled to −78° C., and then condensed isobutylene (75 mL). The cooling bath was removed. After 24 h, ice/water (250 mL) was added followed by washing with ether (2×). The aqueous phase was basified with aq 6N NaOH, then saturated with NaCl, followed by extraction with EtOAc (3×). The combined extracts were washed with brine, dried ($MgSO_4$), and concentrated to give a white solid. This was dissolved in $CH_2Cl_2$ and treated with 1N HCl/ether (22 mL), and then concentrated to give 1-5 as a glassy yellow solid.

$^1$H NMR (400 MHz, DMSO) δ 8.25–8.00 (m, 4H), 7.85–7.58 (m, 5H), 4.08 (m, 1H), 3.10 (m, 1H), 2.73 (m, 1H), 1.17 (s, 9H).

SCHEME 2

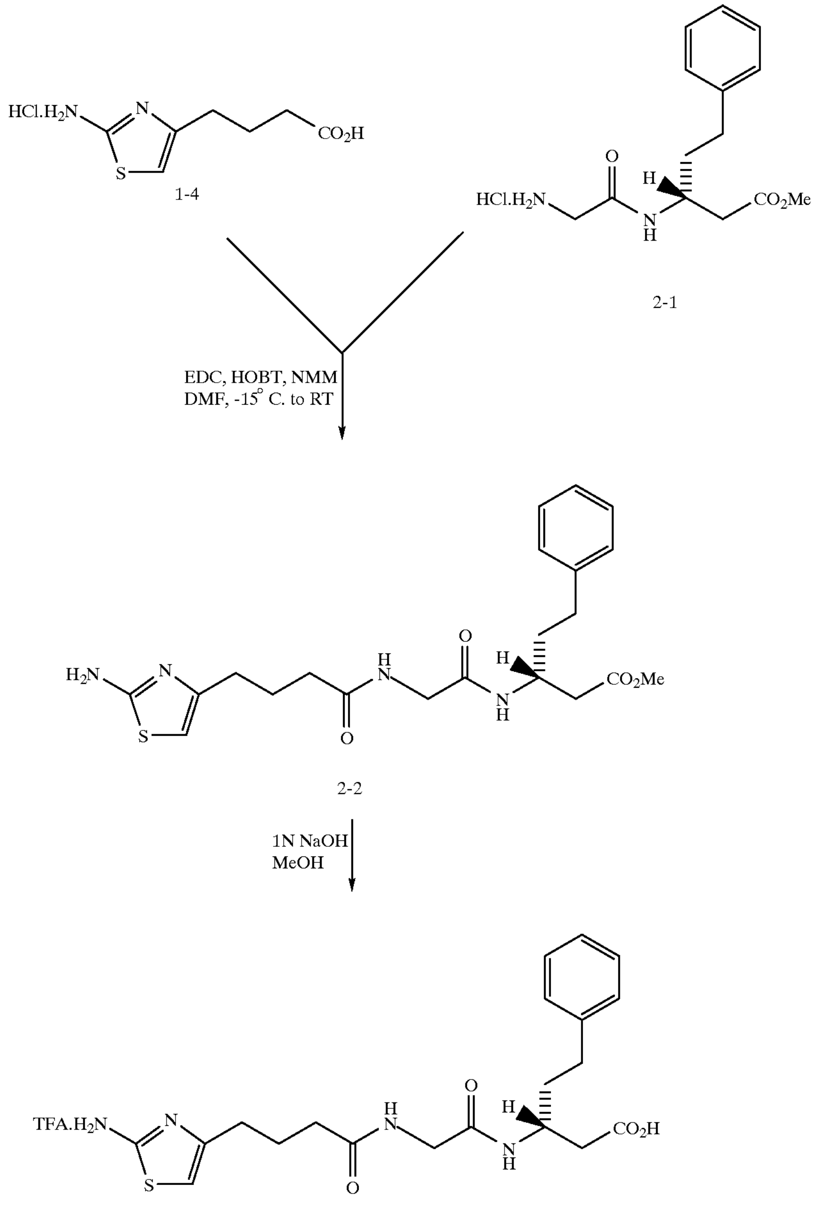

2-2

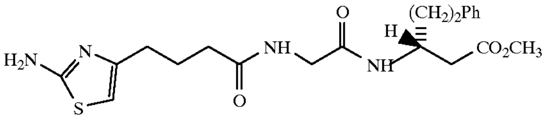

4-(2-Aminothiazol-4-yl)butanoyl-glycyl-3(R)-(2-phenethyl)-β-alanine methvl ester (2-2)

Acid 1-4 (300 mg, 1.35 mmol), amine 2-1 (405 mg, 1.35 mmol) (prepared as described in Duggan et al., U.S. Pat. No. 5,264,420) HOBT (219 mg, 1.62 mmol) and NMM (445 μL, 4.04 mmol) were combined in 7 mL DMF, cooled to −15° C., and EDC (310 mg, 1.61 mmol) was added. The reaction was warmed to RT, stirred overnight, then diluted with EtOAc, washed with water, sat. $NaHCO_3$, and brine, dried ($MgSO_4$), filtered and concentrated. Flash chromatography (silica, 10% MeOHIEtOAc) provided 2-2 as a yellow oil.

TLC $R_f$ 0.32 (silica, 10% MeOH/EtOAc)

$^1$H-NMR (400 MHz, $CDCl_3$): δ 7.82 (d, J=7 Hz, 1H), 7.65 (d, J=8 Hz, 1H), 7.40–7.10 (m, 5H), 6.93 (d, J=8 Hz, 1H), 6.10 (s, 1H), 4.31 (m, 1H), 3.96 (ABX dd, J=17, 6 Hz, 1H), 3.89 (ABX dd, J=17, 5 Hz, 1H), 3.64 (s, 3H), 2.68–2.54 (m), 2.32–2.17 (m, 2H), 2.25–1.80 (m).

2-3

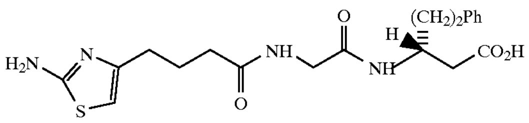

4-(2-Aminothiazol-4-yl)butanoyl-glycyl-3(R)-(2-phenethyl)-β-alanine trifluoroacetate salt (2-3)

Ester 2-2 (220 mg, 0.51 mmol) and 1 N NaOH (1.3 mL, 1.3 mmol) were combined in 5 mL MeOH. After 3 d the reaction mixture was concentrated, purified by flash chromatography (silica, 9:1:1 $CH_2Cl_2$/MeOH/HOAc), then preparative HPLC ($C_{18}$, 0.1% TFA in $CH_3CN/H_2O$), providing, after lyophilization, acid 2-3 as a white solid.

TLC $R_f$ 0.54 (silica, 4:1:1 $CH_2Cl_2$/MeOH/HOAc)

$^1$H-NMR (400 MHz, $CD_3OD$): δ 7.26–7.10 (m, 5H), 6.52 (s, 1H), 4.23 (m, 1H), 3.88 (AB d, J=17 Hz, 1H), 3.79 (AB d, J=17 Hz, 1H), 2.72–2.55 (m, 4H), 2.51 (d, J=7 Hz, 2H), 2.34 (t, J=7 Hz, 2H), 1.99–1.75 (m, 4H).

SCHEME 3

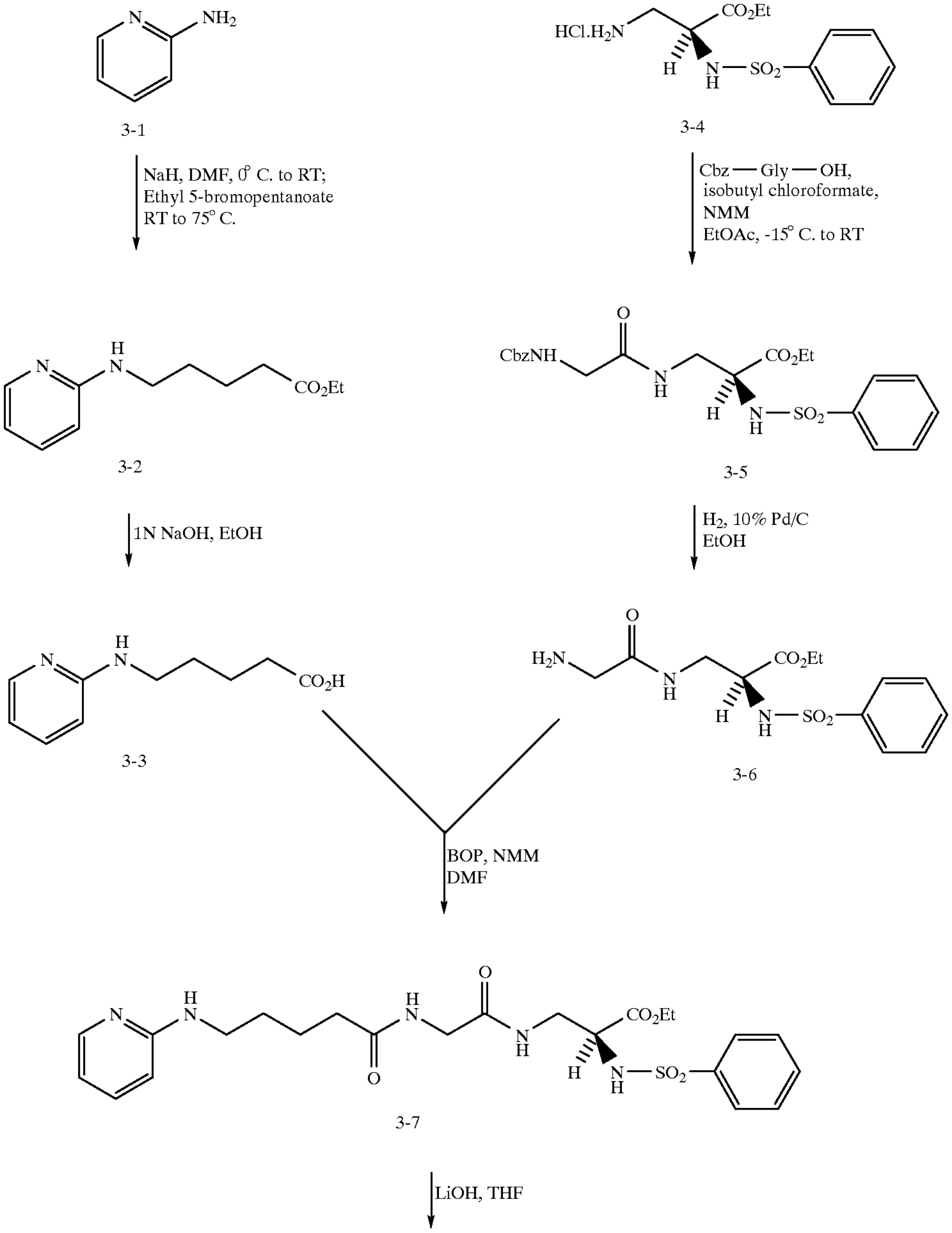

-continued

TFA.
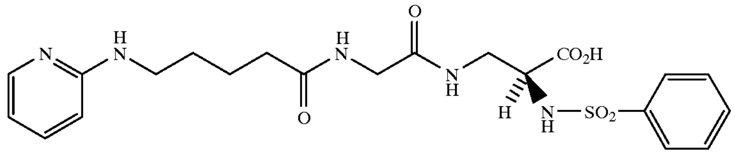
3-8

3-2
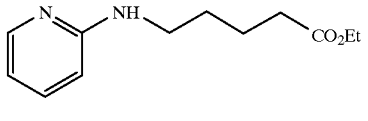

Ethyl 5-(2-pyridylamino)pentanoate (3-2)

2-Aminopyridine (3-1, 1.97 g, 20.9 mmol) in 10 mL DMF was added to a suspension of NaH (60% in oil, 1.00 g, 25 mmol) in 80 mL DMF cooled to 0° C. After warming to RT for 45 min, ethyl 5-bromopentanoate (4.2 mL, 25 mmol) was added dropwise. This mixture was heated at 75° C. overnight, then cooled to RT, diluted with EtOAc, washed with water (2×), sat. $NaHCO_3$, and brine, dried ($MgSO_4$), filtered and concentrated. Flash chromatography (silica, 50% then 70% EtOAc/hexane) provided 3-2 as a yellow oil.

TLC $R_f$ 0.55 (silica, 70% EtOAc/hexane)

$^1$H-NMR (400 MHz, $CDCl_3$): δ 8.07 (dd, J=5, 1 Hz, 1H), 7.40 (m, 1H), 6.55 (m, 1H), 6.37 (d, J=8 Hz, 1H), 4.48 (br s, 1H), 4.13 (q, J=7 Hz, 2H), 3.29 (q, J=7 Hz, 2H), 2.35 (t, J=7 Hz, 2H), 1.80–1.55 (m, 4H), 1.25 (t, J=7 Hz, 3H).

3-3
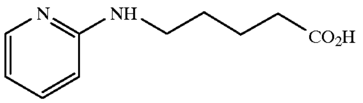

5-(2-Pyridylamino)pentanoic acid (3-3)

Ester 3-2 (0.41 g, 1.84 mmol) was dissolved in 18 mL EtOH, 1 N NaOH (4.6 mL, 4.6 mmol) was added, and the reaction was stirred overnight. The pH of the solution was adjusted to 7 with 1 N HCl, and concentration provided a white solid containing acid 3-3 and NaCl.

TLC $R_f$ 0.06 (silica, 19:1:1 $CH_2Cl_2$/MeOH/HOAc)

$^1$H-NMR (400 MHz, $D_2O$): δ 7.81 (m, 1H), 7.77 (d, J=6 Hz, 1H), 6.96 (d, J=9 Hz, 1H), 6.82 (t, J=7 Hz, 1H), 3.36 (t, J=7 Hz, 2H), 2.24 (m, 2H), 1.72–1.50(m, 4H).

3-5
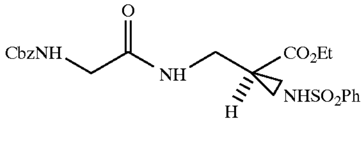

N-Cbz-glycyl-2(S)-phenylsulfonamido-β-alanine ethyl ester (3-5)

N-Cbz-glycine (339 mg, 1.62 mmol) was dissolved in 8 mL EtOAc, cooled to −15° C., then NMM (196 μL, 1.8 mmol) and isobutyl chloroformate (230 μL, 1.8 mmol) were added. After 20 min, the mixed anhydride solution was added to amine 3-4 (0.50 mg, 1.6 mmol) suspended in 5 niL EtOAc and the reaction was warmed to RT for 90 min. Following dilution with EtOAc, the mixture was washed with water, sat. $NaHCO_3$, 5% $KHSO_4$, and brine, dried ($MgSO_4$), filtered and concentrated. Flash chromatography (silica, 75% EtOAc/hexane) provided amide 3-5 as a colorless oil.

TLC $R_f$ 0.29 (silica, 75% EtOAc/hexane)

$^1$H-NMR (300 MHz, $CDCl_3$): δ 7.65–7.45 (m, 3H), 7.40–7.25 (m, 5H), 6.68 (t, J=6 Hz, 1H), 5.83 (d, J=8 Hz, 1H), 5.49 (t, J=6 Hz, 1H), 5.15 (s, 2H), 4.04–3.95 (m, 3H), 3.89–3.85 (m, 2H), 3.73 (m, 1H), 3.46 (m, 1H), 1.11 (t, J=7 Hz, 3H).

3-6
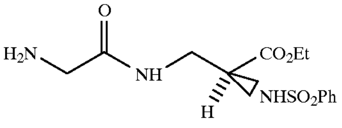

Glycyl-2(S)-phenylsulfonamido-β-alanine ethyl ester (3-6)

Protected amine 3-5 (0.47 g, 1.01 mmol) was dissolved in 10 mL EtOH, 10% Pd/C (94 mg) was added, and the reaction was stirred under an $H_2$ balloon. After 4 h, additional 10% Pd/C was added (94 mg), and the reaction was continued for 3 d. The mixture was filtered through Celite, concentrated, and azeotroped with $CHCl_3$, providing amine 3-6 as a gum.

$^1$H-NMR (300 MHz, $CDCl_3$): δ 7.95 (m), 7.86 (d, J=7 Hz, 2H), 7.60–7.45 (m, 3H), 4.05 (dd, J=5, 6 Hz 1H), 3.96 (q, J=7 Hz, 2H), 3.80–3.55 (m), 1.07 (t, J=7 Hz, 3H).

3-7
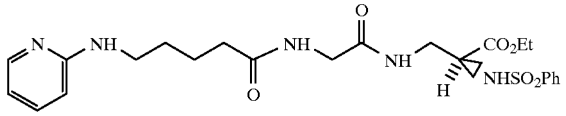

5-(2-Pyridylamino)pentanoylglycyl-2(S)-phenylsulfonamido-β-alanine ethyl ester (3-7)

Acid 3-3 (186 mg, 0.55 mmol), amine 3-6 (150 mg, 0.46 mmol), NMM (0.20 mL, 1.8 mmol) and BOP (302 mg, 0.68 mmol) were combined in 3 mL DMF. After 5 d the DMF was removed on a rotary evaporator, the residue was diluted with EtOAc, then washed with water, sat. $NaHCO_3$, and brine, dried ($MgSO_4$), filtered and concentrated. Flash chromatography (silica, 25% i-PrOH/EtOAc) provided 3-7 as a colorless oil.

TLC $R_f$ 0.30 (silica, 25% i-PrOH/EtOAc)

$^1$H-NMR (400 MHz, $CDCl_3$): δ 8.05 (d, J=4 Hz, 1H), 7.85 (d, J=7 Hz, 2H), 7.57 (t, J=7 Hz, 1H), 7.55–7.45 (m, 2H), 7.42 (m, 1H), 6.80 (br t, 1H), 6.54 (dd, J=6, 4 Hz, 1H), 6.45 (m, 1H), 6.39 (d, J=8 Hz, 1H), 5.19 (m, 1H), 4.16 (ABX dd, J=17, 7 Hz, 1H), 4.08–3.95 (m), 3.85–3.75 (m, 2H), 3.29 (q, J=6 Hz, 2H), 2.40–2.32 (m, 2H), 1.85 (m, J=7 Hz, 2H), 1.75 (m, 2H), 1.10 (t, J=7 Hz, 3H).

3-8

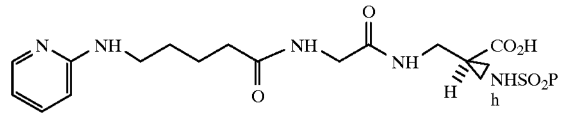

5-(2-Pyridylamino)pentanoylglycyl-2(S)-phenylsulfonamido-β-alanine trifluoroacetate salt (3-8)

Ester 3-7 (59 mg, 0.12 mmol) was dissolved in 1 mL THF, then 1 N LiOH (0.29 mL, 0.29 mmol) was added. After stirring overnight the reaction was concentrated, the mixture was concentrated. Flash chromatography (silica, 22:20:1:1 EtOAc/EtOH/$H_2O$/$NH_4OH$), followed by prep. HPLC (C-18, 0.1% TFA/$CH_3CN$/$H_2O$) and lyophilization provided 3-8 as a white solid.

TLC $R_f$ 0.26 (silica, 22:20:1:1 EtOAc/EtOH/$H_2$/$NH_4OH$)

$^1$H-NMR (400 MHz, $D_2O$): δ 7.83–7.75 (m, 3H), 7.70 (d, J=6 Hz, 1H), 7.67 (d, J=7 Hz, 1H), 7.58 (t, J=7 Hz, 2H), 6.96 (d, J=9 Hz, 1H), 6.80 (t, J=7 Hz, 1H), 3.86–3.80 (m, 3H), 3.55 (dd, J=14, 4 Hz, 1H), 3.36 (m, 2H), 3.29 (dd, J=14, 8 Hz, 1H), 2.39 (m, 2H), 1.72 (m, 4H).

SCHEME 4

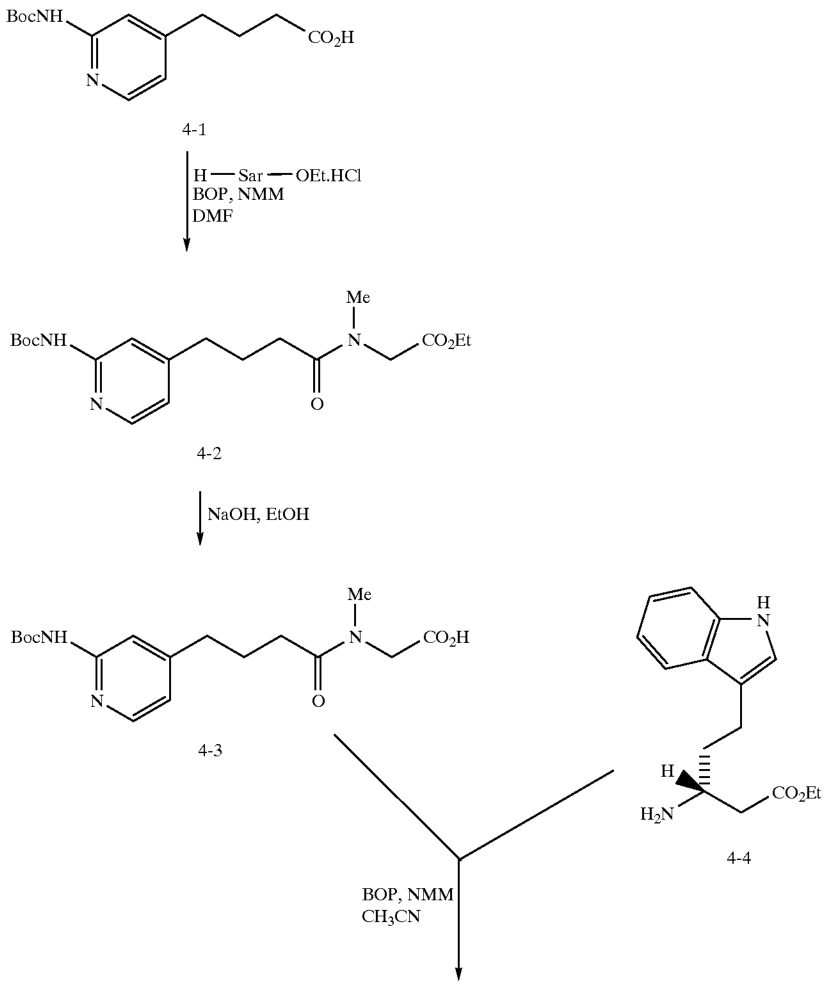

4-1

4-2

4-3

4-4

-continued

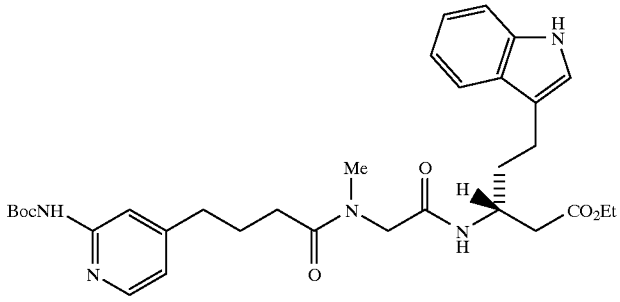

4-5

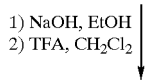

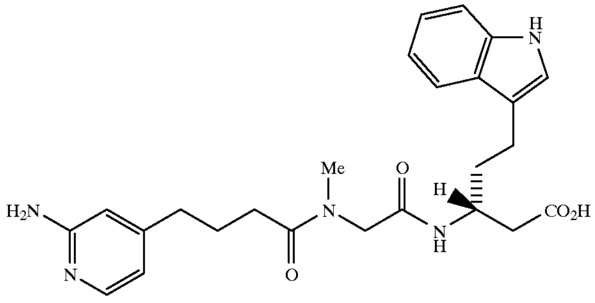

4-6

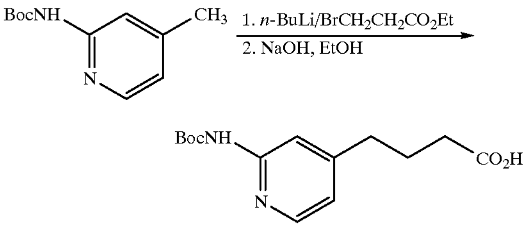

4-1

4-(2-N-Boc-aminopyridin-4-yl)butanoic acid (4-1)

The protected picoline (90 g, 0.43 mol) was dissolved in 3 L THF under $N_2$, cooled to −78° C., and n-BuLi (1.6 M, 675 mL, 1.08 mol) was added during 30 min. The mixture was allowed to warm to RT for 1 h, then the resulting orange suspension was cooled to −78° C. Methyl 3-bromopropionate (79 g, 0.47 mol) was added during 2 min. After 15 min the cooling bath was removed and the mixture was allowed to warm to −20° C. at which point it was quenched with 60 mL HOAc in 250 mL THF. The solution was diluted with 2 L EtOAc, washed with water, sat. $NaHCO_3$, and brine, dried ($MgSO_4$). The aqueous layers were re-extracted with EtOAc (2x), and these organic layers were filtered, concentrated, and dissolved in 1.5 L EtOH and 1.5 L 1 N NaOH (1.5 mol). After 1 h the reaction was concentrated by 1/3, diluted with 4 L EtOAc, the aqueous layer was removed. The pH of the aqueous layer was adjusted to 4-5 with 10% $KHSO_4$, then extracted with EtOAc (2x3L). The EtOAc layers were washed with brine, dried (MgSO4), filtered and concentrated, providing 4-1 as a yellow oil.

4-2

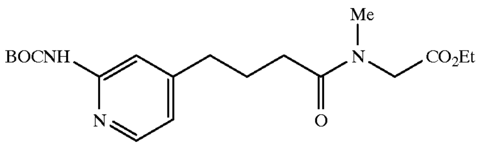

4-(2-Boc-amino-pyridin-6-yl)butanoyl-sarcosine ethyl ester (4-2)

Acid 4-1 (200 mg, 0.71 mmol), H-Sar-OEt·HCl (130 mg, 0.84 mrnol), NMM (314 μL, 2.9 mmol) and BOP (378 mg, 0.86 mmol) were combined in 5 mL DMF. After stirring overnight the reaction mixture was diluted with EtOAc, washed with water (5x), sat. $NaHCO_3$, and brine, dried ($MgSO_4$), filtered and concentrated. Flash chromatography (silica, 50–70% EtOAc/hexane) provided 4-2 as a colorless oil.

TLC $R_f$ 0.54 (silica, 80% EtOAc/hexane)

$^1$H-NMR (400 MHz, $CDCl_3$): 4:1 mixture of amide rotomers, major rotomer δ 8.12 (d, J=5 Hz, 1H), 7.79 (s, 1H), 7.48 (br s, 1H), 6.83 (d, J=6 Hz, 1H), 4.19 (q, J=7 Hz, 2H), 4.11 (s, 2H), 3.03 (s, 3H), 2.68 (t, J=7 Hz, 2H), 2.39 (t, J=7 Hz, 2H), 2.02 (qn, J=7 Hz, 2H), 1.53 (s, 9H) 1.26 (t, J=7Hz, 3H).

4-3

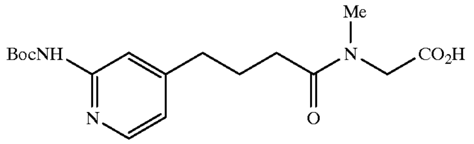

4-(2-Boc-amino-pyridin-4-yl)butanoyl-sarcosine (4-3)

Ester 4-2 (91 mg, 0.24 mmol) was dissolved in 2.4 mL EtOH, and 1 N NaOH (0.60 mL, 0.60 mmol) was added. After 45 min the mixture was concentrated, then diluted with EtOAc, washes with 10% $KHSO_4$ and brine, dried ($MgSO_4$) filtered and reconcentrated, providing acid 4-3 as a glass.

TLC $R_f$ 0.18 (silica, 18:1:1, $CH_2Cl_2$/MeOH/HOAc)

$^1$H-NMR (400 MHz, $CDCl_3$): 1:1 mixture of amide rotomers δ 8.03–7.82 (m, 3H), 6.86 (br s, 1H), 4.15/3.96 (s, 2H), 3.06/3.02 (s, 3H), 2.75–2.65 (m, 2H), 2.40 (m, 2H), 2.22–2.00 (m, 2H), 1.53 (s, 9H).

4-5

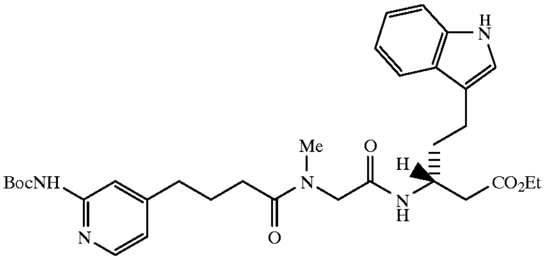

4-(2-Boc-amino-pyridin-4-yl)butanoyl-sarcosine-3(R)-[2-(indol-3-yl)ethyl]-β-alanine ethyl ester (4-5)

Acid 4-3 (84 mg, 0.24 mmol), amine 4-4 (see Duggan et al., U.S. Pat. No. 5,264,420) (68 mg, 0.26 mmol), NMM (104 μL, 0.95 mmol) and BOP (127 mg, 0.29 mmol) were combined in 2.4 mL $CH_3CN$. After stirring overnight the mixture was diluted with EtOAc, washed with water (4×), sat. $NaHCO_3$, and brine, dried ($MgSO_4$) and concentrated. Flash chromatography (silica, EtOAc) provided 4-5 as a colorless oil TLC $R_f$ 0.66 (silica, 20% MeOH/EtOAc)

$^1$H-NMR (400 MHz, $CDCl_3$): 4:1 mixture of amide rotomers, major rotomer δ 8.12 (s, 1H), 8.09 (d, J=5 Hz, 1H), 7.78 (s, 1H), 7.55 (d, J=8 Hz, 1H), 7.39 (s, 1H), 7.34 (d, J=8 Hz, 1H), 7.17 (t, J=8 Hz, 1H), 7.08 (t, J=7 Hz, 1H), 7.03 (d, J=2 Hz, 1H), 6.79 (dd, J=5, 1 Hz, 1H), 6.71 (d, J=9 Hz, 1H), 4.32 (m, 1H), 4.16–4.05 (m, 3H), 4.00 (AB d, J=15 Hz, 1H), 3.94 (AB d, J=15 Hz, 1H), 3.04 (s, 3H), 2.77 (m, 2H), 2.63 (t, J=8 Hz, 2H), 2.53 (m, 2H), 2.36 (m, 2H), 2.02–1.90 (m, 4H), 1.53 (s, 9H), 1.22 (t, J=7 Hz, 3H).

4-6

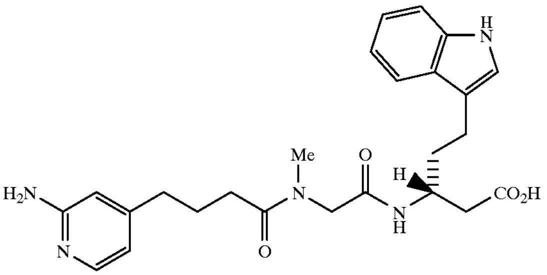

4-(2-Aminopyridin-4-yl)butanoyl-sarcosine-3(R)-[2-(indol-3-yl)ethyl]-β-alanine (4-6)

Ester 4-5 (20 mg, 34 μmol) was dissolved in 350 μL EtOH, then 1 N NaOH (85 μL, 85 μmol) was added. After 2 h the reaction was diluted with EtOAc, washed with 10% $KHSO_4$ and brine, dried ($MgSO_4$), filtered and concentrated. The residue was dissolved in 1 mL $CH_2Cl_2$, treated with 1 mL TFA for 1 h, then concentrated and azeotroped with toluene. Flash chromatography (silica, 50:1:1, EtOH/$H_2O$/$NH_4OH$) provided 4-6 as an off-white solid.

TLC $R_f$ 0.55 (silica, 20:1:1 EtOH/$H_2O$/$NH_4OH$)

$^1$H-NMR (400 MHz, $CD_3OD$): 2:1 mixture of amide rotomers δ 7.72/7.67 (d, J=6 Hz, 1H), 7.52 (t, J=8 Hz, 1H), 7.30 (t, J=8 Hz, 1H), 7.07–6.90 (m, 4H), 6.55/6.54 (s, 1H), 6.49 (s, 1H), 4.36–4.25 (m, 1H), 4.14–3.93 (m, 2H), 3.06/2.93 (s, 3H), 2.60 (t, J=8 Hz, 2H), 2.55–2.45 (m, 4H), 2.34 (t, J=7 Hz, 1H), 2.05–1.84 (m).

SCHEME 5
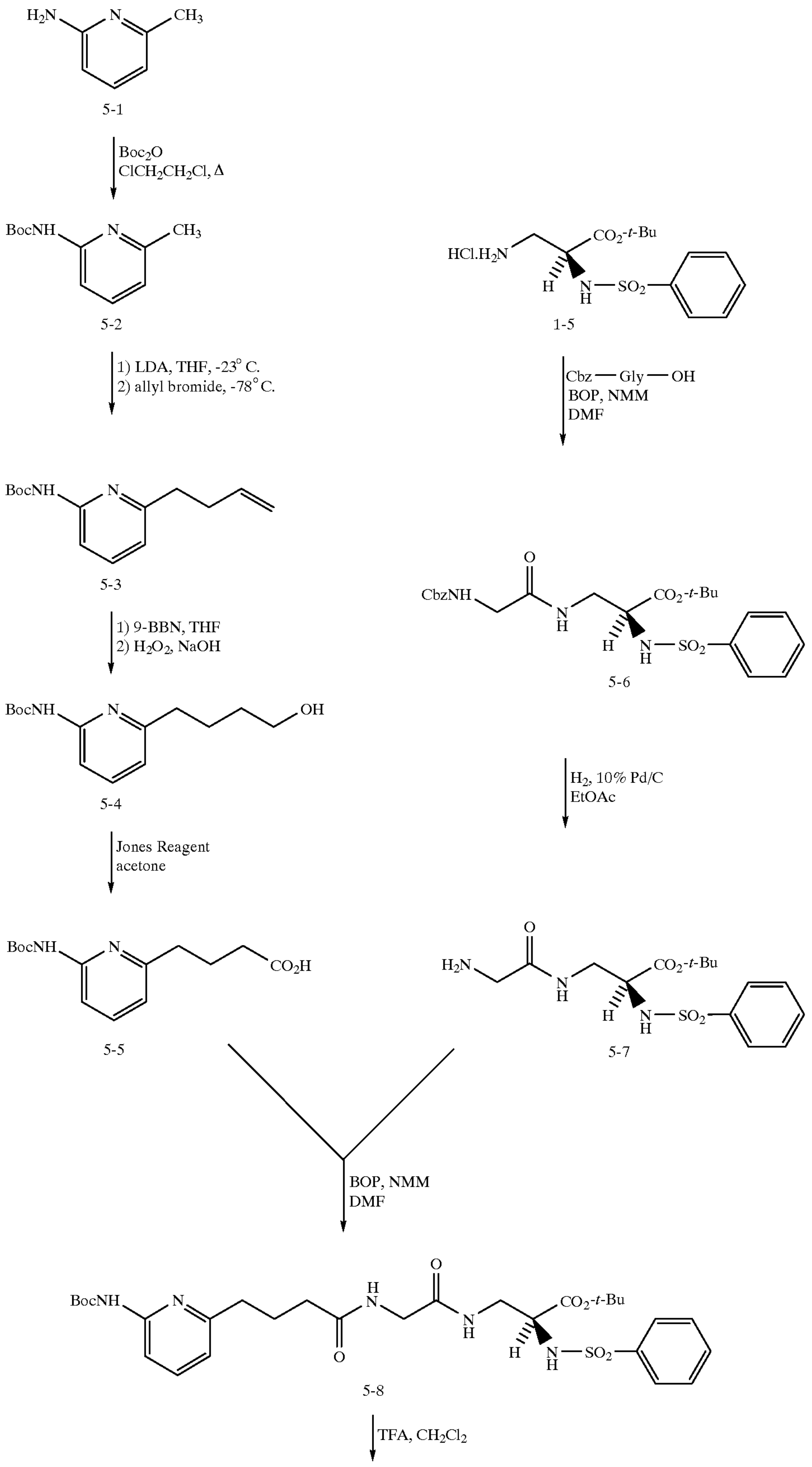

-continued

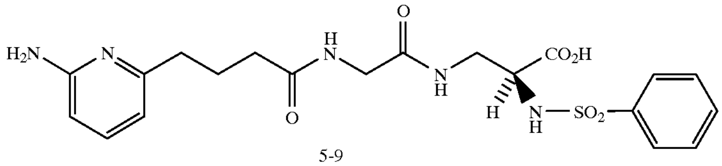

5-9

5-2

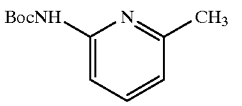

2-(Boc-amino)-6-methvlpvridine (5-2)

2-Amino-6-picoline (5.0 g, 46.2 mmol) and $Boc_2O$ (11.1 g, 50.8 mmol) were combined in 150 mL dichloroethane. After heating at reflux for 6 h, additional $Boc_2O$ (2.0 g, 9.2 mmol) was added, and the reaction was heated overnight. After concentration, the reaction mixture was flash filtered (silica, $CH_2Cl_2$), providing 5-2 as a waxy solid.

TLC $R_f$ 0.21 (silica, $CH_2Cl_2$)

$^1$H-NMR (400 MHz, $CDCl_3$): δ 7.70 (d, J=8 Hz, 1H), 7.54 (t, J=8 Hz, 1H), 7.19 (br s, 1H), 6.80 (d, J=7 Hz, 1H), 2.42 (s, 3H), 1.51 (s, 9H).

5-3

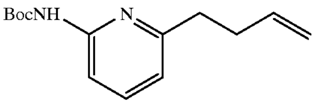

2-Boc-amino-6-(4-butenyl)pyridine (5-3)

Methylpyridine 5-2 (4.0 g, 19.2 mmol) was dissolved in 40 mL THF, cooled to −23° C., and LDA (2 M, 24 mL, 48 mmol) was added dropwise. After 30 min the mixture was cooled to −78° C. and allyl bromide (2.49 mL, 2.88 mmol) was added dropwise. After 15 min more, the reaction was quenched with sat. $NH_4Cl$, warmed to RT, diluted with EtOAc, and the organic layer was washed with brine. After drying ($MgSO_4$), filtration and concentration, flash chromatography provided 5-3 as a yellow oil.

TLC $R_f$ 0.40 (silica, 75% $CH_2Cl_2$/hexane)

$^1$H-NMR (300 MHz, $CDCl_3$): δ 7.72 (d, J=8 Hz, 1H), 7.56 (t, J=8 Hz, 1H), 7.16 (br s, 1H), 6.80 (d, J=7 Hz, 1H), 5.85 (m, 1H), 5.03 (dm, J=17 Hz, 1H), 4.97 (dm, J=10 Hz, 1H), 2.74 (t, J=7 Hz, 2H), 2.42 (qm, J=7 Hz, 2H), 1.52 (s, 9H).

5-4

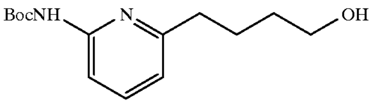

2-(Boc-amino)-6-(4-hydroxybutyl)pyridine (5-4)

A solution of alkene 5-3 (558 mg, 2.25 mmol) in 2 mL THF was added dropwise to a solution of 9-BBN (0.5 M in THF, 4.95 mL, 2.48 mmol). After stirring overnight, and additional portion of 9-BBN (0.5 M, 1.1 mL, 0.55 mmol) was added and the reaction was continued 1 h more. The reaction was quenched by the successive addition of EtOH (1.5 mL), 6 N NaOH (0.5 mL), and 30% $H_2O_2$ (1.0 mL, exothermic), and heating to 50° C. for 1 h. The cooled mixture was saturated with $K_2CO_3$, then partitioned between EtOAc and water. The aqueous phase was reextracted with EtOAc, the combined organic phases were washed with brine, dried ($MgSO_4$), filtered and concentrated. Flash chromatography (silica, 40% EtOAc/hexane) provided alcohol 5-4 as a colorless oil.

TLC $R_f$ 0.26 (silica, 40% EtOAc/hexane)

$^1$H-NMR (400 MHz, $CDCl_3$): δ 7.73 (d, J=8 Hz, 1H), 7.56 (t, J=8 Hz, 1H), 7.20 (br s, 1H), 6.80 (d, J=7 Hz, 1H), 3.67 (t, J=7 Hz, 2H), 2.70 (t, J=7 Hz, 2H), 1.77 (qn, J=7 Hz, 2H), 1.61 (m, 2H), 1.51 (s, 9H).

5-5

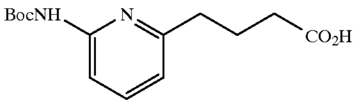

4-(2-Boc-aminopyridin-6-yl)butanoic acid (5-5)

A solution of alcohol 5-4 (247 mg, 0.93 mmol) in 5 mL acetone was cooled to 0° C. and a solution of Jones Reagent was added dropwise. As the color of the reaction changed from brown to green, additional Jones Reagent was added, until the alcohol was no longer detected by TLC (3.5 h). After quenching with i-PrOH the mixture was diluted with EtOAc, washed with 5% $KHSO_4$ and brine, dried ($MgSO_4$), filtered and concentrated, providing 5-5 as an off-white waxy solid.

$^1$H-NMR (400 MHz, $CDCl_3$): δ 9.13 (br s, 1H), 7.90 (d, J=8 Hz, 1H), 7.64 (t, J=8 Hz, 1H), 6.85 (d, J=8 Hz, 1H), 2.80 (t, J=8 Hz, 2H), 2.46 (t, J=7 Hz, 2H), 2.01 (qn, J=7 Hz, 2H), 1.54 (s, 9H).

5-6

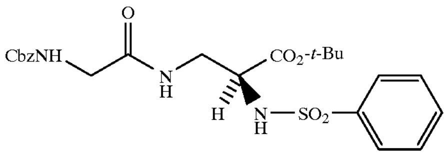

N-Cbz-glycyl-2(S)-phenylsulfonamido-β-alanine t-butyl ester (5-6)

Amine 1-5 (0.42 g, 1.25 mmol), Cbz-Gly-OH (288 mg, 1.38 mmol), NMM (0.55 mL, 5.0 mmol) and BOP (829 mg, 1.88 mmol) were combined in 6 mL DMF. After stirring overnight the solvent was evaporated, the residue was taken up in EtOAc, the organic solution was washed with water (2×), 5% $KHSO_4$, sat. $NaHCO_3$ and brine, dried ($MgSO_4$), filtered and concentrated. Flash chromatography (silica, 60% EtOAc/hexane) provided 5-6 as a white glass.

TLC $R_f$ 0.27 (silica, 60% EtOAc/hexane)

$^1$H-NMR (400 MHz, $CDCl_3$): δ 7.83 (d, J=7 Hz, 2H), 7.58 (t, J=7 Hz, 1H), 7.50 (t, J=8 Hz, 2H), 7.42–7.30 (m, 5H), 6.55 (br s, 1H), 5.59 (d, J=7 Hz, 1H), 5.40 (br s, 1H), 5.16 (s, 2H), 3.95–3.70 (m, 4H), 3.34 (m, 1H), 1.27 (s, 9H).

5-7

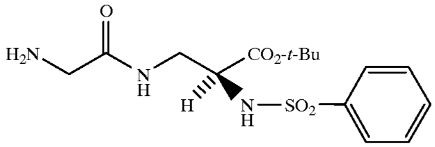

Glycyl-2(S)-phenylsulfonamido-β-alanine t-butyl ester (5-7)

A solution of 5-6 (0.54 g, 1.10 mmol) in 11 mL EtOAc was treated with 10% Pd/C (108 mg) and stirred under a $H_2$ balloon overnight. After addition of more 10% Pd/C (100 mg) and hydrogenation for 5 d the mixture was filtered through Celite and concentrated, providing 5-6 as a white glass.

$^1$H-NMR (400 MHz, $CD_3OD$): δ 7.84 (dm, J=8 Hz, 2H), 7.61 (tm, J=8 Hz, 1H), 7.54 (tm, J=8 Hz, 2H), 4.00 (dd, J=8, 5 Hz, 1H), 3.59 (dd, J=14, 5 Hz, 1H), 3.37 (s, 2H), 1.25 (s, 9H).

5-8

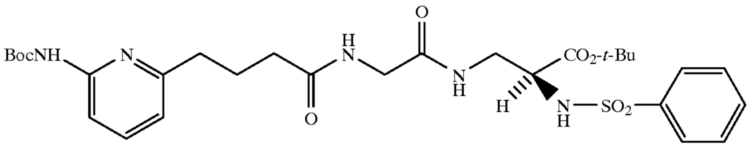

4-(2-Boc-aminopyridin-6-yl)butanoyl-glycyl-2(S)-phenylsulfonamido-β-alanine t-butyl ester (5-8)

Acid 5-5 (144 mg, 0.51 mmol), amine 5-7 (202 mg, 0.56 mmol), NMM (226 μL, 2.1 mmol) and BOP (241 mg, 0.77 mmol) were combined in 2.6 mL DMF. After stirring overnight the solvent was evaporated, the residue was dissolved in EtOAc, washed with water, sat. $NaHCO_3$, 5% $KHSO_4$, and brine, dried ($MgSO_4$), filtered and concentrated. Flash chromatography (silica, 10% $CHCl_3$/EtOAc) provided 5-8 as an off-white glass.

TLC $R_f$ 0.22 (silica, 10% $CHCl_3$/EtOAc)

$^1$H-NMR (400 MHz, $d_6$-DMSO): δ 9.53 (s, 1H), 8.23 (br d, J=7 Hz, 1H), 7.98 (t, J=6 Hz, 1H), 7.91 (t, J=6 Hz, 1H), 7.76 (d, J=7 Hz, 2H), 7.65–7.53 (m, 5H), 6.87 (d, J=7 Hz, 1H), 3.85 (br s, 1H), 3.60 (t, J=5 Hz, 2H), 3.20–3.10 (m, 2H), 2.60 (t, J=7 Hz, 2H), 2.15 (t, J=7 Hz, 2H), 1.85 (qn, J=7 Hz, 2H), 1.46 (s, 9H), 1.18 (s, 9H).

5-9

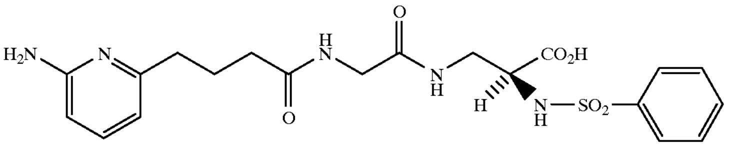

4-(2-Aminopyridin-6-yl)butanoyl-glycyl-2(S)-phenylsulfonamido-β-alanine (5-9)

A solution of 5-8 (138 mg, 0.22 mmol) in 1 mL $CH_2Cl_2$ was cooled to 0° C., treated with 1 mL TFA, and warmed to RT for 5 h. After concentration and azeotroping with toluene the residue was purified by flash chromatography (silica, 12:20:1:1, EtOAc/EtOH/$H_2O$/$NH_4OH$), providing 5-9 as a colorless glass.

TLC $R_f$ 0.34 (silica, 12:20:1:1, EtOAc/EtOH/$H_2O$/$NH_4OH$)

$^1$H-NMR (400 MHz, $D_2O$): δ 7.76 (dm, J=7 Hz, 2H), 7.55–7.48 (m 4H), 6.69 (d, J=7 Hz, 1H), 6.57 (d, J=8 Hz, 1H), 3.72–3.62 (m, 2H), 3.55 (dd, J=8, 5 Hz, 1H), 3.37 (dd, J=13, 8 Hz, 1H), 3.13 (dd, J=13, 8 Hz, 1H), 2.63 (t, J=7 Hz, 2H), 2.34 (t, J=7 Hz, 2H), 1.96 (qn, J=7 Hz, 2H).

SCHEME 6

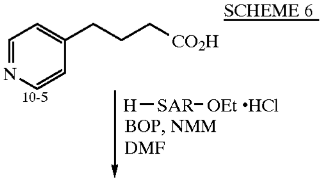

-continued

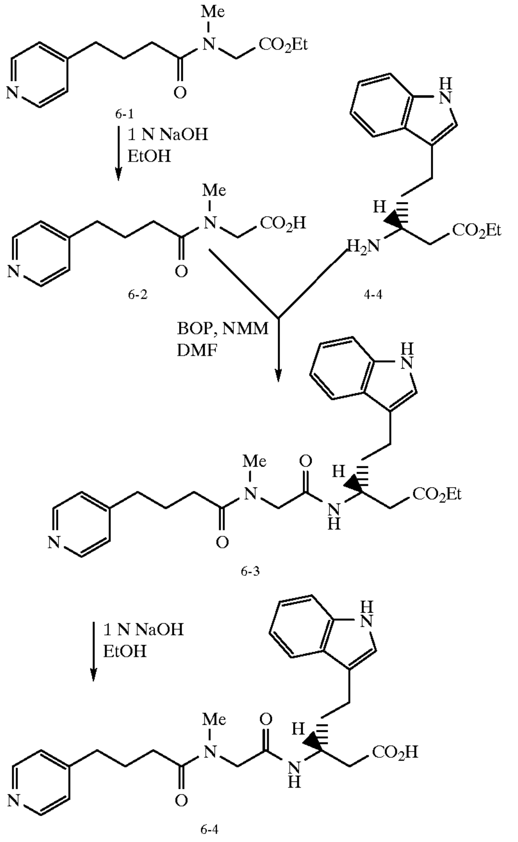

6-1

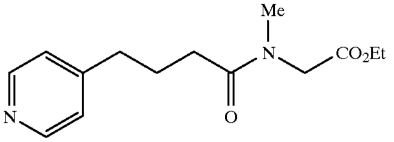

4-(Pyridin-4-yl)butanoyl-sarcosine ethyl ester (6-1)

4-(4-Pyridyl)butanoic acid 10-5 (100 mg, 1.8 mmol), H-Sar-OEt·HCl (300 mg, 2.0 mmol), BOP (965 mg, 2.2 mmol) and NMM (700 μL, 6.4 mmol) were combined in 9 mL DMF. After stirring overnight the mixture was diluted with EtOAc, washed with water (4×), sat. $NaHCO_3$, and brine, dried ($MgSO_4$), filtered and concentrated. Flash chromatography (silica, 80% to 100% EtOAc/hexane) provided 6-1 as a colorless oil.

TLC $R_f$ 0.44 (silica, 20% MeOH/EtOAc)

$^1$H-NMR (400 MHz, $CDCl_3$): 4:1 mixture of amide rotomers, major rotomer δ 8.50 (d, J=5 Hz, 2H), 7.14 (d, J=5 Hz, 2H), 4.20 (q, J=7 Hz, 2H), 4.12 (s, 2H), 3.03 (s, 3H), 2.70 (t, J=8 Hz, 2H), 2.39 (t, J=7 Hz, 2H), 2.02 (qn, J=7 Hz, 2H), 1.23 (t, J=7 Hz, 3H).

6-2

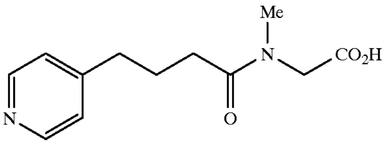

4-(Pyridin-4-yl)butanoyl-sarcosine (6-2)

Ester 6-1 (324 mg, 1.22 mmol) was dissolved in 6 mL EtOH, then 1 N NaOH (2.4 mL, 2.4 mmol) was added. After stirring overnight the mixture was concentrated, rediluted with EtOAc, extracted into 10% $KHSO_4$, then concentrated, providing acid 6-2, along with inorganic salts.

TLC $R_f$ 0.16 (silica, 4:1:1 $CH_2Cl_2$/MeOH/HOAc)

$^1$H-NMR (400 MHz, $CD_3OD$): 1:1 mixture of amide rotomers, δ 8.41 (br s, 2H), 7.33 (m, 2H), 4.00/3.90 (s, 2H), 3.05/2.95 (s, 3H), 2.77–2.67 (m, 2H), 2.48/2.37 (t, J=7 Hz, 2H), 2.00–1.90 (m, 2H).

6-3

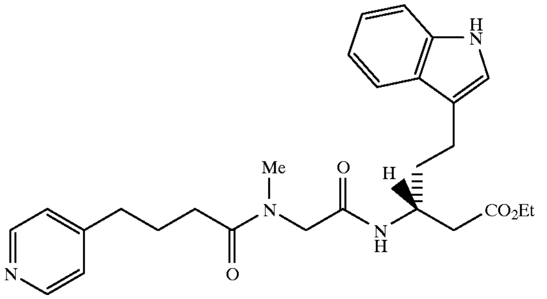

4-(Pyridin-4-yl)butanoyl-sarcosine-3(R)-[2-(indol-3-yl)ethyl]-β-alanine ethyl ester (6-3)

Acid 6-2 (288 mg, 1.22 mmol), amine 4-4 (318 mg, 1.22 mmol), BOP (647 mg, 1.5 mmol), and NMM (462 μL, 4.2 mmol) were combined in 6 mL DMF. After stirring overnight the mixture was diluted with EtOAc, washed with water (4×), sat. $NaHCO_3$, and brine, dried ($MgSO_4$), filtered and concentrated. Flash chromatography (silica, EtOAc then 5% MeOH/EtOAc) provided 6-3 as an orange oil.

TLC $R_f$ 0.4 (20% MeOH/EtOAc)

$^1$H-NMR (400 MHz, $CDCl_3$): 4:1 mixture of amide rotomers, major rotomer δ 8.47 (br d, J=5 Hz, 2H), 8.02 (br d, J=6 Hz, 2H), 7.58 (dd, J=16, 8 Hz, 1H), 7.34 (dd, J=8, 4 Hz, 1H), 7.20–7.03 (m, 3H), 7.01 (s, 1H), 6.72 (d, J=9 Hz, 1H), 4.33 (m, 1H), 4.1 (t, J=7 Hz, 3H), 3.98 (s, 2H), 3.05 (s, 3H), 2.90–2.45 (m), 2.39 (t, J=7 Hz, 2H), 2.02–1.70 (m), 1.23 (t, J=7 Hz, 3H).

6-4

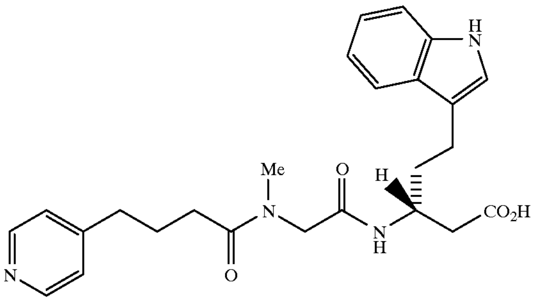

4-(Pyridin-4-yl)butanoyl-sarcosine-3(R)-[2-(indol-3-yl)ethyl]-β-alanine (6-4)

Ester 6-3 (400 mg, 0.84 mmol) was dissolved in 4 mL EtOH, then 1 N NaOH (1.7 mL, 1.7 mmol) was added. After 90 min the reaction was neutralized with 1 N HCl (1.7 mL, 1.7 mmol) and concentrated to an oil. Flash chromatography (silica, 50:1:1 EtOH/$H_2O$/$NH_4OH$, then again with 12:10:1:1 EtOAc/EtOH/$H_2O$/$NH_4OH$) provided 6-4.

TLC $R_f$ 0.17 (silica, 12:10:1:1 EtOAc/EtOH/$H_2O$/$NH_4OH$) $^1$H-NMR (400 MHz, $CD_3OD$): 2:1 mixture of amide rotomers, δ 8.38–8.28 (m, 2H), 7.54–7.48 (m, 1H), 7.30–7.25 (m, 2H), 7.21–7.19 (m, 1H), 7.07–6.92 (m, 3H), 4.36–4.27 (m, 1H), 4.03–3.98 (m, 2H), 3.06/2.93 (s, 3H), 2.86–2.60 (m, 4H), 2.52–2.32 (m), 2.05–1.85 (m).

SCHEME 7

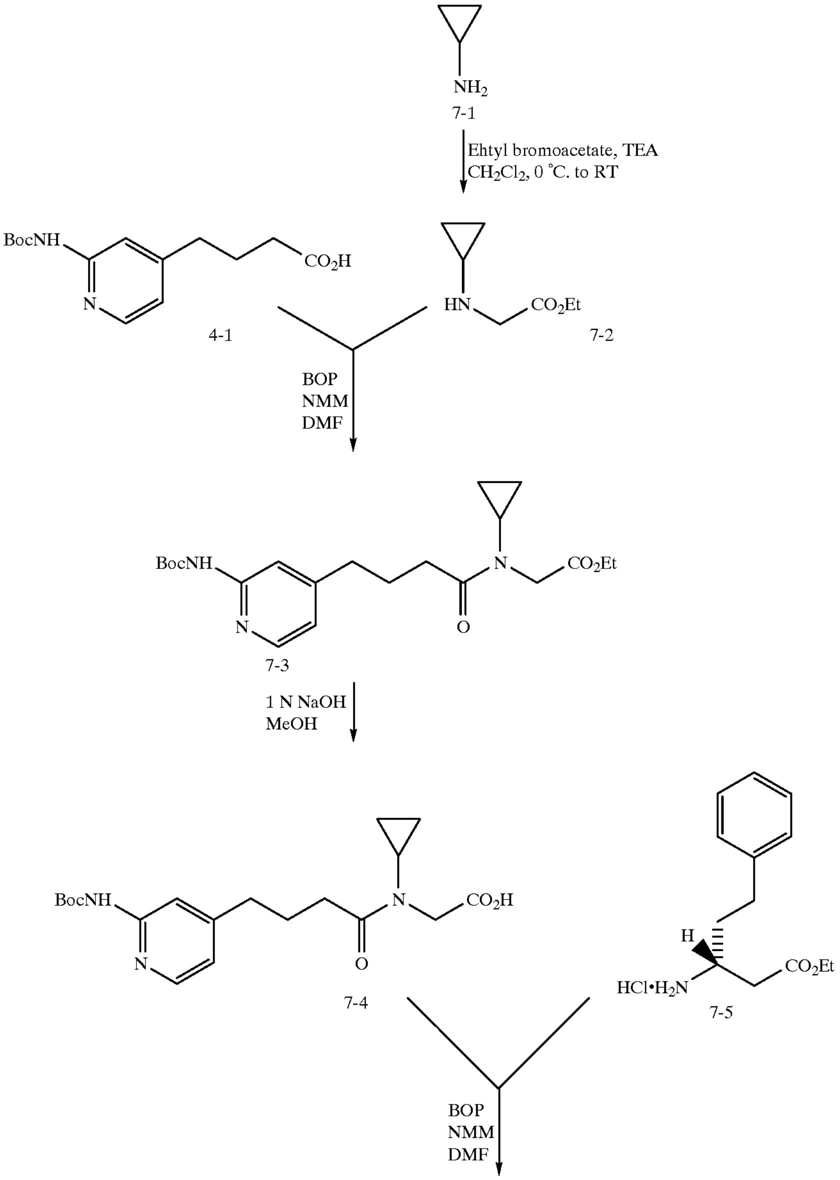

-continued

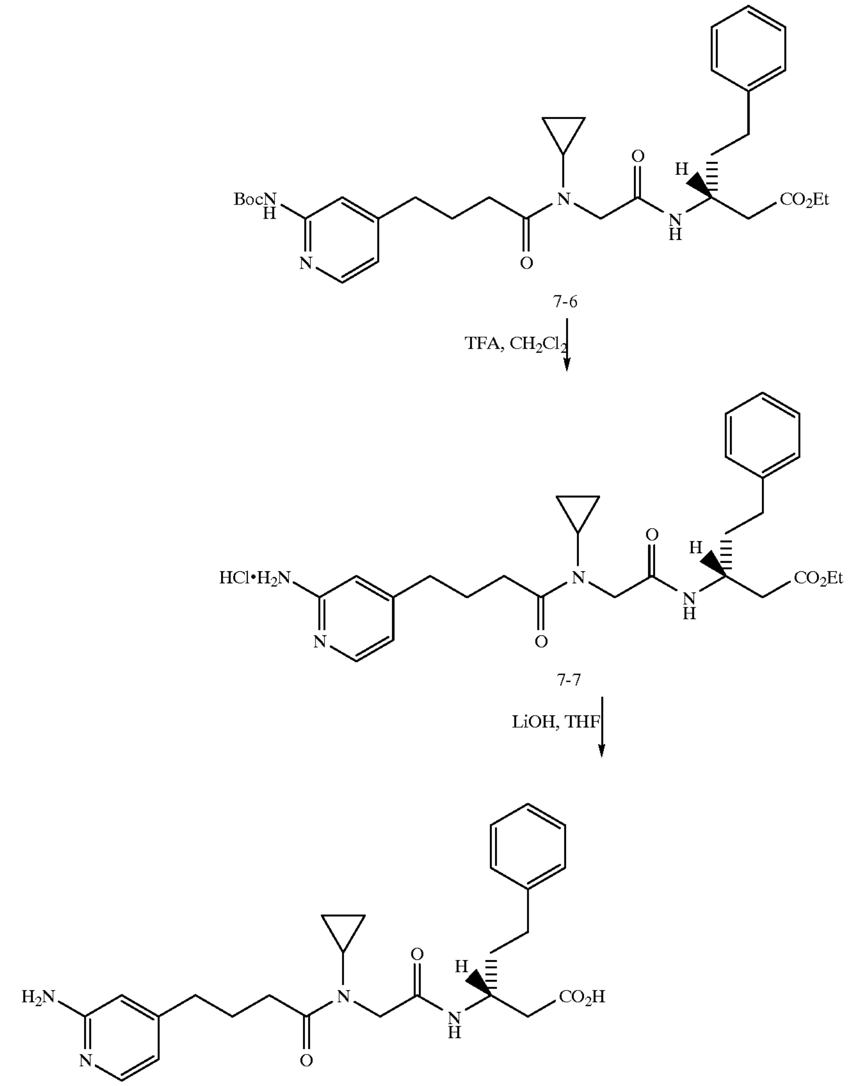

7-8

7-2

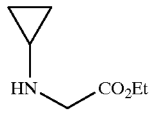

7-3

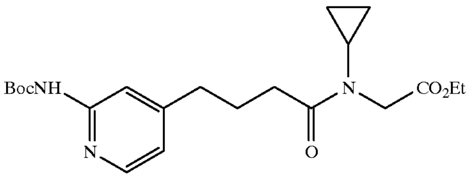

N-Cyclopropylglycine ethyl ester (7-2)

Cyclopropylamine (12.1 mL, 175 mmol) and TEA (42 mL, 385 mmol) were combined at 0° C. in 350 mL $CH_2Cl_2$, then ethyl bromoacetate (19.4 mL, 175 mmol) was added dropwise. The reaction was warmed to RT for 3 h, then diluted with additional $CH_2Cl_2$, washed with water, sat. $NaHCO_3$, and brine, dried ($Na_2SO_4$), filtered and concentrated. Flash filtration (silica, 30% EtOAc/hexane) provided 7-2 as a light yellow oil.

TLC $R_f$ 0.70 (silica, EtOAc)

$^1$H-NMR (400 MHz, $CDCl_3$): δ 4.20 (q, J=7 Hz, 2H), 3.45 (s, 2H), 2.23 (tt, J=6, 3 Hz, 1H), 1.29 (t, J=7 Hz, 3H), 0.43 (m, 2H), 0.36 (m, 2H).

4-(2-Boc-amino-pyridin-4-yl)butanoyl-N-cyclopropylglycine ethyl ester (7-3)

Acid 4-1 (0.86 g, 3.1 mmol), amine 7-2 (0.48 g, 3.4 mmol), NMM (1.35 mL, 12.3 mmol) and BOP (2.04 g, 4.61 mmol) were combined in 15 mL DMF. After stirring overnight the mixture was concentrated, redissolved in EtOAc, washed with water, 5% $KHSO_4$, sat. $NaHCO_3$ and brine, dried over $MgSO_4$, filtered and concentrated. Flash chromatography (silica, 50% EtOAc/hexane) provided 7-3 as a colorless oil.

TLC $R_f$ 0.29 (silica, 50% EtOAc/hexane)

$^1$H-NMR (400 MHz, $CDCl_3$): δ 8.14 (d, J=5 Hz, 1H), 7.81 (s, 1H), 7.77 (br s, 1H), 6.84 (dd, J=5, 1 Hz, 1H), 4.18 (q, J=7 Hz, 2H), 4.08 (s, 2H), 2.80 (tt, J=7, 4 Hz, 1H), 2.69 (t, J=7 Hz, 2H), 2.60 (t, J=7 Hz, 2H), 2.02 (qn, J=7 Hz, 2H), 1.53 (s, 9H), 1.27 (t, J=7 Hz, 3H), 0.83 (m, 2H), 0.72 (m, 2H).

7-4

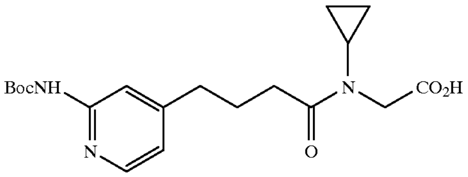

4-(2-Boc-amino-pyridin-4-yl)butanoyl-N-cyclopropylglycine (7-4)

Ester 7-3 (1.07 g, 2.64 mmol) was dissolved in 26 mL MeOH, then treated with 1 N NaOH (6.6 mL, 6.6 mmol). After stirring overnight the reaction was concentrated, redissolved in water, the pH was adjusted to 1 with 10% $KHSO_4$, then extracted with EtOAc (5×). The aqueous phase was adjusted to pH 3 with aq. NaOH, then reextracted with EtOAc (2×). The combined organic phases were washed with brine, dried ($MgSO_4$), filtered and concentrated, providing 7-4 as a white foam.

TLC $R_f$ 0.24 (silica, 19:1:1, $CH_2Cl_2$/MeOH/HOAc)

$^1$H-NMR (300 MHz, $CDCl_3$): δ 9.15 (br s, 1H), 7.97 (d, J=5 Hz, 1H), 7.94 (s, 1H), 6.89 (dd, J=5, 1 Hz, 1H), 4.14 (s, 2H), 2.81 (tt, J=7, 3 Hz, 1H), 2.73 (t, J=7 Hz, 2H), 2.61 (t, J=7 Hz, 2H), 2.04 (qn, J=7 Hz, 2H), 1.51 (s, 9H), 0.85 (m, 2H), 0.76 (m, 2H).

7-6

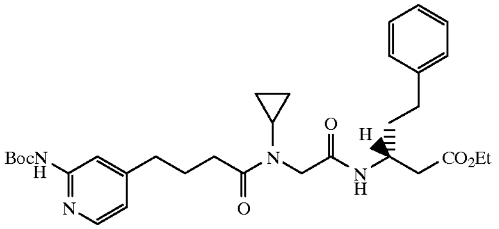

4-(2-Boc-amino-pyridin-4-yl)butanoyl-N-cyclopropylglycyl-3 (R)-(2-phenethyl)-β-alanine ethvl ester (7-6)

Acid 7-4 (415 mg, 1.1 mmol), amine hydrochloride 7-5 (see procedure in EP 478 362 utilizing Boc-Gly(OEt) as starting material) (284 mg, 1.1 mmol), NMM (0.48 mL, 4.4 mmol) and BOP (729 mg, 1.65 mmol) were combined in 5 mL DMF. After stirring overnight the reaction was concentrated, redissolved in EtOAc, washed with water, 5% $KHSO_4$, sat. $NaHCO_3$, and brine, dried ($MgSO_4$), filtered and concentrated. Flash chromatography (silica, EtOAc) provided 7-6 as a colorless waxy solid.

TLC $R_f$ 0.39 (silica, EtOAc)

$^1$H-NMR (400 MHz, $d_6$-DMSO): δ 9.66 (s, 1H), 8.11 (d, J=5 Hz, 1H), 7.76 (d, J=9 Hz, 1H), 7.68 (s, 1H), 7.25 (t, J=7 Hz, 2H), 7.20–7.12 (m, 3H), 6.88 (dd, J=5, 1 Hz, 1H), 4.01 (q, J=7 Hz, 2H), 3.91 (AB d, J=16 Hz, 1H), 3.83 (AB d, J=16 Hz, 1H), 3.32 (s, 2H), 2.78 (m, 1H), 2.65–2.40 (m), 1.86–1.77 (m), 1.46 (s, 9H), 1.14 (t, J=7 Hz, 3H), 0.77–0.70 (m, 4H).

7-7

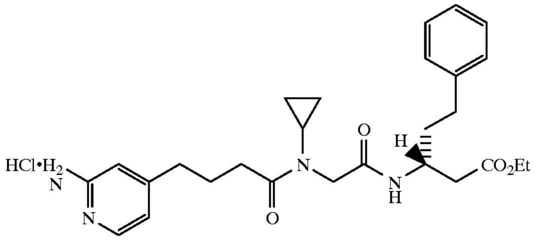

4-(2-Amino-pyridin-4-yl)butanoyl-N-cyclopropylglycyl-3(R)-(2-phenethyl)-β-alanine ethyl ester hydrochloride (7-7)

A solution of 7-6 (530 mg, 0.91 mmol) in 4.6 mL $CH_2Cl_2$ was cooled to 0° C., 4.6 mL TFA was added, and after 1 h the reaction was warmed to RT for 90 min. After concentration and azeotroping with toluene the residue was purified by flash chromatography (silica, 10:1, EtOAc:$NH_3$-saturated EtOH). The residue was dissolved in EtOAc, treated with 1 N HCl in ether, concentrated, then lyophilized from aq. acetonitrile, providing 7-7 as a glassy solid.

TLC $R_f$ 0.25 (10:1, EtOAc:$NH_3$-saturated EtOH)

$^1$H-NMR (400 MHz, $d_6$-DMSO): δ 7.94 (br s, 1H), 7.86–7.82 (m, 2H), 7.25 (t, J=7 Hz, 2H), 7.20–7.13 (m, 3H), 6.80–6.75 (m, 2H), 4.05 (m), 4.02 (q, J=7 Hz, 2H), 3.93 (AB d, J=16 Hz, 1H), 3.85 (AB d, J=16 Hz, 1H), 2.78 (qn, 1H), 2.65 (t, J=7 Hz, 2H), 2.59 (t, J=7 Hz, 2H), 2.55–2.40 (m), 1.82 (qn, J=7 Hz, 2H), 1.80–1.70 (m, 2H), 1.15 (t, J=7 Hz, 3H), 0.80–0.70 (m, 4H).

7-8

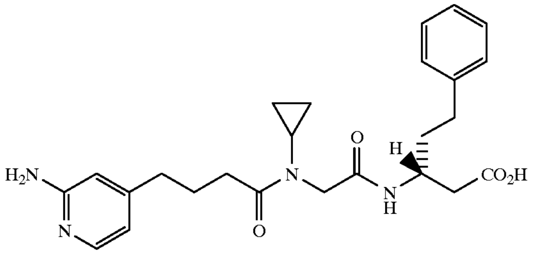

4-(2-Amino-pyridin-6-yl)butanoyl-N-cyclopropylglycyl-3(R)-(2-phenethyl)-β-alanine (7-8)

Ester 7-7 (100 mg, 0.18 mmol) was dissolved in 4 mL THF, then treated with 1 N LiOH (0.9 mL, 0.9 mmol). After stirring overnight the mixture was concentrated and purified by flash chromatography (silica, 15:20:1:1 EtOAc/EtOH/$H_2O$/$NH_4OH$) to provide 7-8 as a white solid.

TLC $R_f$ 0.36 (silica, 15:20:1:1 EtOAc/EtOH/$H_2O$/$NH_4OH$)

$^1$H-NMR (400 MHz, $d_6$-DMSO): δ 7.81 (d, J=9 Hz, 1H), 7.77 (d, J=5 Hz, 1H), 7.27 (t, J=7 Hz, 2H), 7.20–7.12 (m, 3H), 6.34 (dd, J=5, 1 Hz, 1H), 6.28 (s, 1H), 5.76 (br s, 2H), 4.03 (m, 1H), 3.91 (AB d, J=16 Hz, 1H), 3.85 (AB d, J=16 Hz, 1H), 2.76 (m, 1H), 2.65–2.50 (m), 2.45 (t, J=7 Hz, 2H), 2.37 (d, J=7 Hz, 2H), 1.82–1.60 (m), 0.77–0.68 (m, 4H).

SCHEME 8
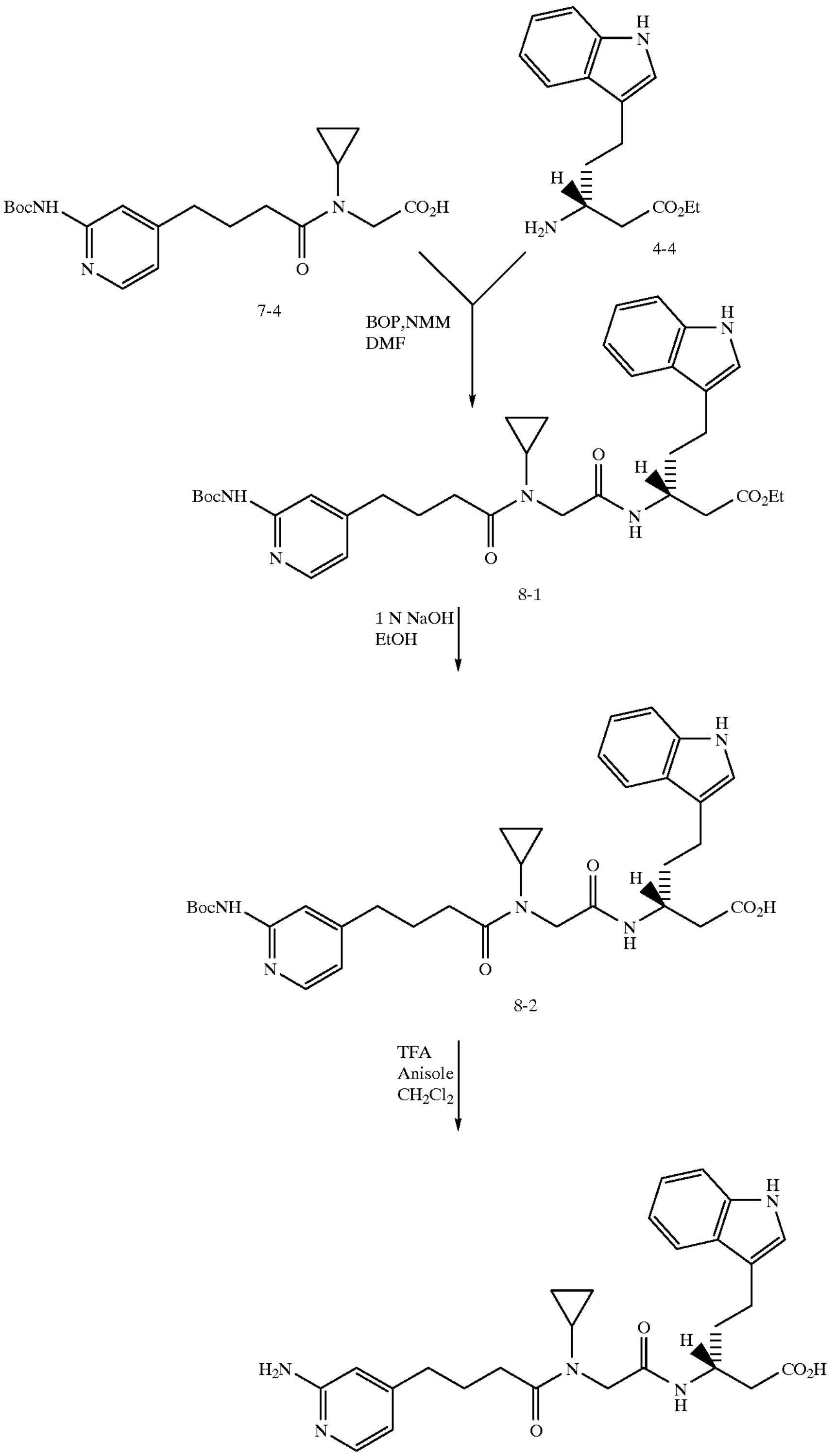
7-4
4-4
8-1
8-2
8-3

8-1

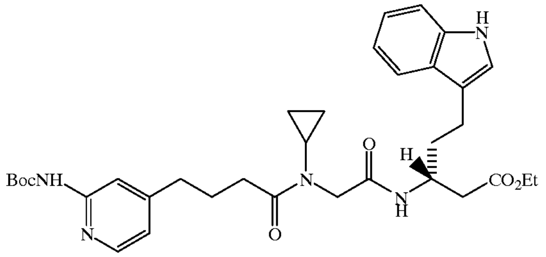

4-(2-Boc-amino-pyridin-4-yl)butanoyl-N-cyclopropylglycyl-3(R)-[2-(indol-3-yl)ethyl]-β-alanine ethyl ester (8-1)

Acid 7-4 (180 mg, 0.48 mmol), amine 4-4 (130 mg, 0.50 mmol), NMM (183 μL, 1.7 mmol) and BOP (253 mg, 0.57 mmol) were combined in 5 mL DMF. After stirring overnight the reaction was concentrated, redissolved in EtOAc, washed with water (3x), 10% $KHSO_4$, sat. $NaHCO_3$, and brine, dried ($MgSO_4$), filtered and concentrated. Flash chromatography (silica, 80% EtOAc/hexane) provided 8-1 as a glassy solid.

TLC $R_f$ 0.34 (silica, EtOAc)

$^1$H-NMR (400 MHz, $CDCl_3$): δ 8.10–8.00 (m, 2H), 7.79 (s, 1H), 7.56 (d, J=8 Hz, 1H), 7.35–7.30 (m, 2H), 7.16 (t, J=8 Hz, 1H), 7.08 (t, J=8 Hz, 1H), 7.04 (s, 1H), 6.80 (d, J=5 Hz, 1H), 6.71 (d, J=9 Hz, 1H), 4.29 (m, 1H), 4.09 (q, J=7 Hz, 2H), 3.99 (s, 2H), 2.85–2.70 (m, 4H), 2.66 (t, J=7 Hz, 2H), 2.61 (t, J=7 Hz, 2H), 2.51 (m), 2.05–1.87 (m, 4H), 1.53 (s, 9H), 1.21 (t, J=7 Hz, 3H), 0.90–0.75 (m, 4H).

8-2

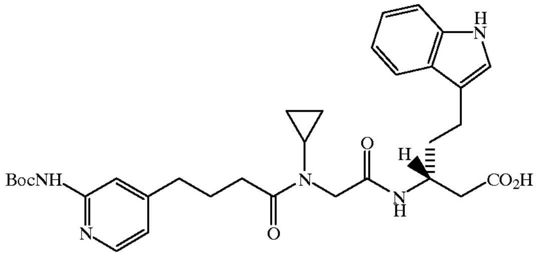

4-(2-Boc-amino-pyridin-4-yl)butanoyl-N-cyclopropylglycyl-3(R)-[2-(indol-3-yl)ethyl]-β-alanine (8-2)

Ester 8-1 (223 mg, 0.36 mmol) was dissolved in 4 mL EtOH, then 1 N NaOH (0.90 mL, 0.90 mmol) was added. After a few hours the reaction was diluted with EtOAc, extracted with water and the pH of the aq. phase was adjusted to 1 with 10% $KHSO_4$. The aqueous layer was extracted with EtOAc (2x), the combined organic layers were washed with brine, dried ($MgSO_4$), filtered and concentrated, providing 8-2 as an oil.

TLC $R_f$ 0.64 (silica, 9:1:1 $CH_2Cl_2$/MeOH/HOAc)

8-3

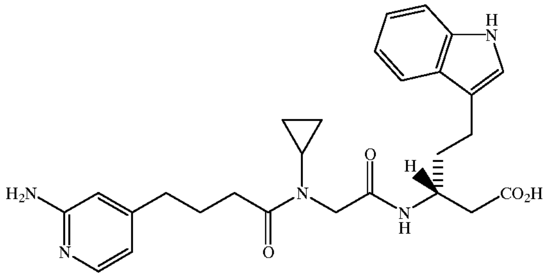

4-(2-Amino-pyridin-4-yl)butanoyl-N-cyclopropylglycyl-3(R)-[2-(indol-3-yl)ethyl]-β-alanine (8-3)

Acid 8-2 (144 mg, 0.24 mmol) was dissolved in 3 mL $CH_2Cl_2$, then anisole (120 μL, 0.96 mmol) and TFA (3 mL) were added. After ca 1 h the reaction was concentrated. Flash chromatography (silica, 18:10:1:1 EtOAc/EtOH/$H_2O$/$NH_4OH$, twice) provided 8-3 as a white solid.

TLC $R_f$ 0.29 (silica, 18:10:1:1 EtOAc/EtOH/$H_2O$/$NH_4OH$)

$^1$H-NMR (400 MHz, $D_2O$): δ 7.88 (m, 1H), 7.70 (m, 1H), 7.53 (m, 1H), 7.30–7.10 (m, 3H), 6.69 (m, 1H), 6.58 (m, 1H), 4.23 (m, 1H), 3.99 (m, 2H), 2.84 (m, 3H), 2.70 (m, 2H), 2.62 (m, 2H), 2.44 (m), 2.10–1.82 (m), 0.88–0.72 (m, 4H).

SCHEME 9

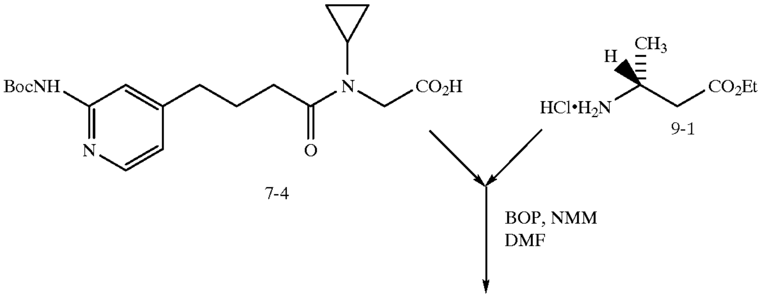

7-4

9-1

-continued

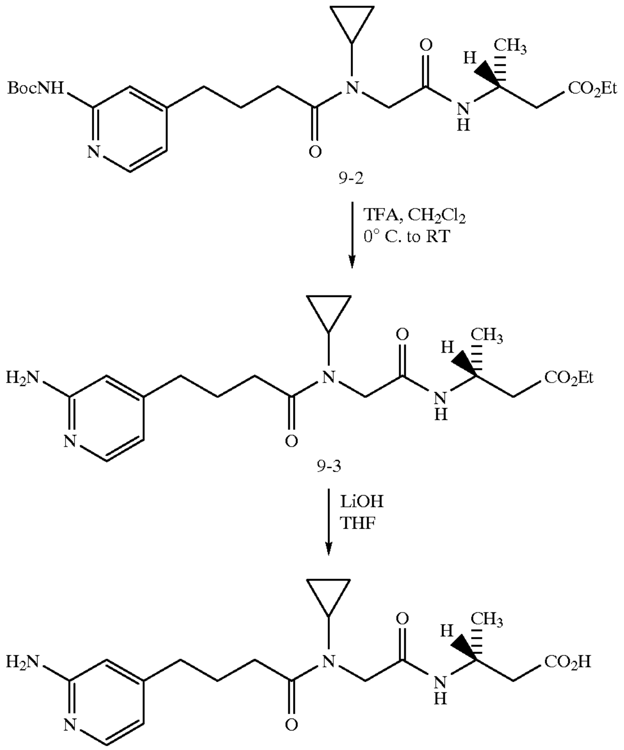

9-2

9-3

9-4

9-2

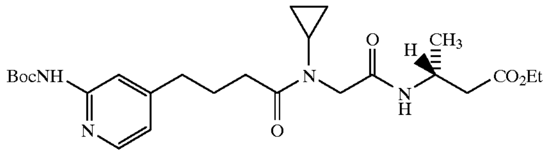

4-(2-Boc-amino-pyridin-4-yl)butanoyl-N-cyclopropylglycyl-3(R)-methyl-β-alanine ethyl ester (9-2)

Acid 7-4 (100 mg, 0.26 mmol), amine hydrochloride 9-1 (see U.S. Pat. No. 5,281,585) (49 mg, 0.29 mmol), NMM (117 μL, 1.1 mmol) and BOP (176 mg, 0.40 mmol) were combined in 1.3 mL DMF. After 3 d the mixture was concentrated, redissolved in EtOAc, washed with water (2×), 5% $KHSO_4$, sat. $NaHCO_3$, and brine, dried ($MgSO_4$), filtered and concentrated. Flash chromatography (silica, EtOAc) provided 9-2 as a colorless oil.

TLC $R_f$ 0.27 (silica, EtOAc)

$^1$H-NMR (400 MHz, $CDCl_3$): δ 8.10 (d, J=5 Hz, 1H), 8.00 (br s, 1H), 7.85 (s, 1H), 6.90 (dd, J=5, 1 Hz, 1H), 6.63 (d, J=8 Hz, 1H), 4.30 (m, 1H), 4.12 (q, J=7Hz, 2H), 4.02 (AB d, J=15 Hz, 1H), 3.93 (AB d, J=15 Hz, 1H), 2.77 (m, 1H), 2.73 (t, J=7 Hz, 2H), 2.62 (t, J=7 Hz, 2H), 2.47 (m, 2H), 2.04 (m, 2H), 1.53 (s, 9H), 1.25 (t, J=7 Hz, 3H), 1.20 (d, J=7 Hz, 3H), 0.88–0.78 (m, 4H).

9-3

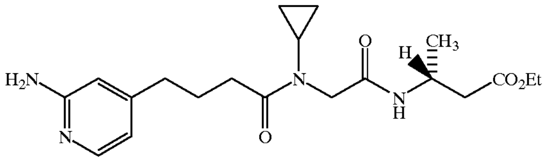

4-(2-Amino-pyridin-4-yl)butanoyl-N-cyclopropylglycyl-3(R)-methyl-β-alanine ethyl ester (9-3)

A solution of 9-2 (84 mg, 0.17 mmol) in 1 mL $CH_2Cl_2$ at 0° C. was treated with 1 mL TFA. After 3 h the mixture was warmed to RT for 1 h, then concentrated and azeotroped with toluene. Flash chromatography (silica, 15% $NH_3$ satd. i-PrOH/EtOAc) and lyophilization from aq. acetonitrile provided 9-3 as a semi-solid.

TLC $R_f$ 0.19 (silica, 15% $NH_3$ satd. i-PrOH/EtOAc)

$^1$H-NMR (400 MHz, d6-DMSO): δ 7.78 (d, J=5 Hz, 1H), 7.76 (d, J=8 Hz, 1H), 6.37 (dd, J=5, 1 Hz, 1H), 6.30 (s, 1H), 5.90 (br s, 1H), 4.09 (m, J=7 Hz, 1H), 4.04 (q, J=7 Hz, 2H), 3.86 (AB d, J=16 Hz, 1H), 3.79 (AB d, J=16 Hz, 1H), 2.73 (m, 1H), 2.45 (t, J=7 Hz, 2H), 2.35 (ABX dd, J=15,7Hz, 1H), 1.77 (qn, J=7Hz, 2H), 1.17 (t, J=7 Hz, 3H), 1.07 (d, J=7 Hz, 3H), 0.76–0.67 (m, 4H).

9-4

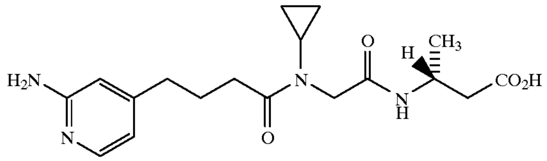

4-(2-Amino-pyridin-4-yl)butanoyl-N-cyclopropylglycyl-3(R)-methyl-β-alanine (9-4)

Ester 9-3 (44 mg, 0.1 1 mmol) was dissolved in 1.1 mL THF, then 1 N LiOH (0.28 mL, 0.28 mmol) was added. After stirring overnight the reaction mixture was loaded directly onto a flash chromatography column (silica, eluting with 7:20:1:1 EtOAc/EtOH/$H_2O$/$NH_4OH$) providing 9-4 as a white solid.

TLC $R_f$ 0.62 (silica, 7:20:1:1 EtOAc/EtOH/$H_2O$/$NH_4OH$)

$^1$H-NMR (300 MHz, $D_2O$): δ 7.72 (d, J=7 Hz, 1H), 6.90–6.90 (m, 2H), 4.16 (hex, J=7 Hz, 1H), 4.04 (s, 2H), 2.86 (tt, J=7, 4 Hz, 1H), 2.80–2.65 (m, 4H), 2.41 (ABX dd, J=14, 6 Hz, 1H), 2.31 (ABX dd, J=14, 7 Hz, 1H), 1.98 (qn, J=7 Hz, 2H), 1.16 (d, J=7 Hz, 3H), 0.89 (m, 2H), 0.80 (m, 2H).

SCHEME 10

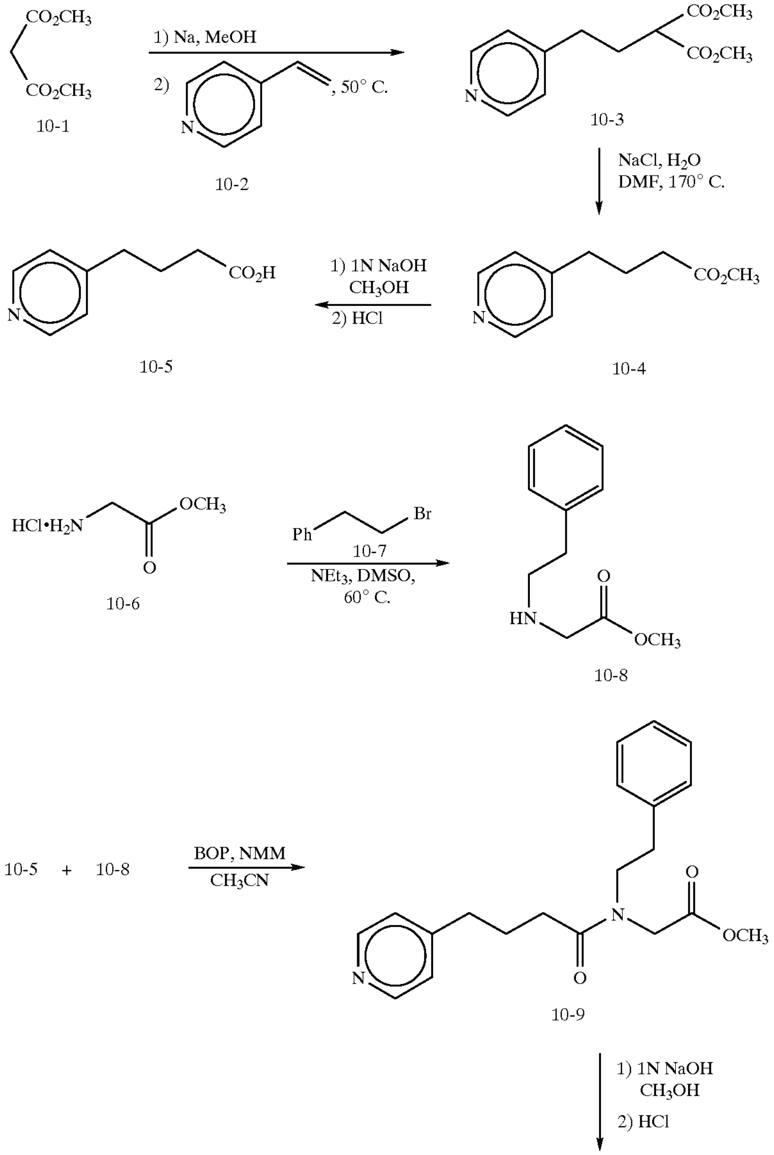

10-1, 10-2, 10-3, 10-4, 10-5, 10-6, 10-8, 10-5 + 10-8, 10-9

-continued

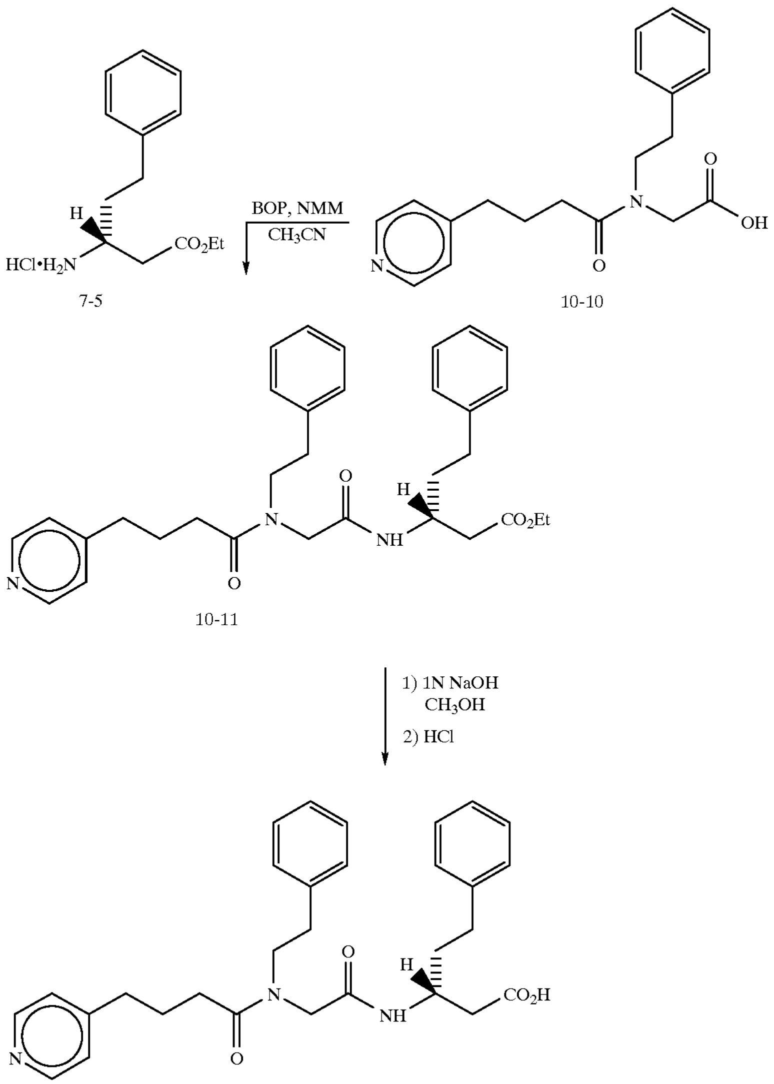

7-5

10-10

10-11

10-12

10-3

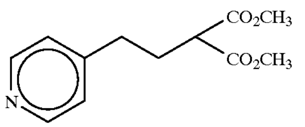

Methyl 2-(methoxycarbonyl)-4-(pyridin-4-yl) butyrate (10-3)

To a stirred solution of elemental sodium (20 g, 840 mmol) and $CH_3OH$ (600 ml) was added dimethyl malonate 10-1 (135 ml, 1120 mmol). After 5 minutes, 4-vinyl pyridine 10-2 (15.3 ml, 140 mmoles) was added and the solution was heated to 50° C. for 18 h. The reaction was diluted with EtOAc and then washed with sat $NaHCO_3$, brine, dried ($MgSO_4$) and concentrated. Flash chromatoraphy (silica, 60% EtOAc/hexanes) furnished the diether 10-3 (19.1 g) as a yellow oil.

TLC $R_f$=0.43 (silica, EtOAc)

$^1$H NMR (400 MHz, $CDCl_3$) δ 8.52 (d, J=6 Hz, 2H), 7.12 (d, J=6 Hz, 2H), 3.75 (s, 6H), 3.38 (t, J=8 Hz, 1H), 2.64 (t, J=8 Hz, 2H), 2.24 (m, 2H).

10-4

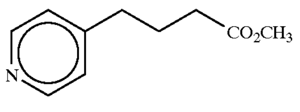

Methyl 4-(Pyridin-4-yl)butyrate (10-4)

A solution of diester 10-3 (19.0 g, 80.1 mmol), $H_2O$ (1.45 ml, 80.1 mmol), NaCl (10.5 g, 160.2 mmol) and DMF was heated to 170° C. for 18 h. The reaction was diluted with EtOAc and then washed with sat. $NaHCO_3$, brine, dried ($MgSO_4$) and concentrated. Flash chromatography (silica, 60% EtOAc/hexanes) afforded ester 10-4 as a brown oil.

TLC $R_f$ 0.32 (silica, EtOAc)

$^1$H NMR (400 MHz, $CD_3OD$) δ 8.40 (d, J=6 Hz, 2H), 7.28 (d, J=6 Hz, 2H), 3.64 (s, 3H), 2.67 (t, J=8 Hz, 2H), 2.36 (t, J=8 Hz, 2H), 1.94 (m, 2H).

10-5

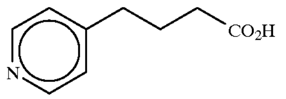

4-(Pyridin-4-yl)butanoic acid (10-5)

A solution of ester 10-4 (10.0 g, 56 mmol), 1N NaOH (84 ml, 84 mmole) and $CH_3OH$ (200 ml) was stiffed at ambient temperature for 1.0 h. Concentrated HCl (7.0 ml, 84 mmol) was added followed by concentration. The residue was dissolved in $CHCl_3$, dried ($MgSO_4$) and concentrated to give acid 10-5 as a yellow solid.

TLC $R_f$ 0.41 (silica 10:1:1 $CH_2Cl_2$/MeOH/AcOH)

$^1$H NMR (400 MHz, $CD_3OD$) δ 8.40 (d, J=6 Hz, 2H), 7.30 (d, J=6 Hz, 2H), 2.71 (t, J=8 Hz, 2H), 2.32 (t, J=7 Hz, 2H), 1.93 (m, 2H).

10-8

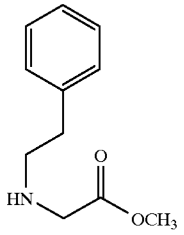

N-(2-Phenethyl)glycine methyl ester (10-8)

A solution of amine methyl ester 10-6 (1.0 g, 7.96 mmol), bromide 10-7 (1.09 ml, 7.96 mmole), $NEt_3$ (3.33 ml, 23.9 mmol) and DMSO (25 ml) was heated to 60° C. for 16 h. The reaction mixture was diluted with EtOAc and then washed with sat. $NaHCO_3$, brine, dried ($MgSO_4$) and concentrated. Flash chromatography (silica, 80% EtOAc/hexanes) furnished ester 10-8 as a yellow oil.

TLC $R_f$ 0.29 (silica, EtOAc)

$^1$H NMR (400 MHz, $CDCl_3$) δ 7.29 (m, 2H), 7.22 (m, 3H), 3.71 (s, 3H), 3.43 (s, 2H), 2.89 (m, 2H), 2.82 (m, 2H).

10-9

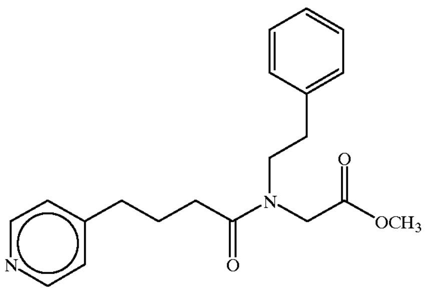

4-(Pyridin-4-yl)butanoyl-N-(2-phenethyl)glycine methyl ester (10-9)

To a stirred solution of acid 10-5 (342 mg, 2.07 mmol), NMM (910 μl, 8.28 mmol) and $CH_3CN$ (15 ml) was added BOP reagent (1.01 g, 2.28 mmol). After 30 minutes, amine 10-8 (400 mg, 2.07 mmol) was added and stirring continued for an additional 18 h. The reaction was diluted with EtOAc and then washed with sat. $NaHCO_3$, brine, dried ($MgSO_4$) and concentrated. Flash chromatography (silica, EtOAc) furnished ester 10-9 as a yellow oil.

TLC $R_f$=0.23 (silica, EtOAc)

$^1$H NMR ($CD_3OD$) 8.39 (d, J=8 Hz, 2H), 7.14–7.29 (m, 7H), 4.84 (s, 2H), 3.70 (s, 3H), 3.58 (t, J=7 Hz, 2H), 2.82 (t, J=7 Hz, 2H), 2.66 (t, J=8 Hz, 0.56H), 2.55 (t, J=8 Hz, 1.44H), 2.28 (t, J=7 Hz, 0.56H), 2.10 (t, J=7Hz, 1.44H).

10-10

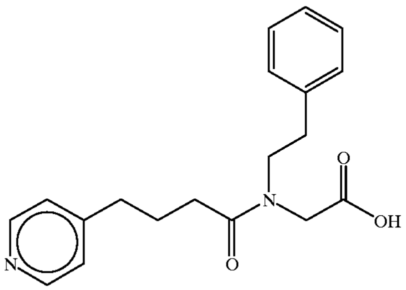

4-(Pyridin-4-yl)butanoyl-N-(2-phenethyl)glycyl (10-10)

A solution of ester 10-9 (500 mg, 1.47 mmole), 1N NaOH (2 ml, 2 mmol) and $CH_3OH$ (5 ml) was stirred at ambient temperature for 2.0 h. Concentrated HCl (167 μl, 2.0 mmol) was added followed by concentration. The residue was dissolved in $CHCl_3$, dried ($MgSO_4$) and concentrated to give acid 10-10 as a white solid.

$^1$H NMR (400 MHz, $CD_3OD$) δ 8.47 (d, J=5 Hz, 2H), 7.44 (m, 2H), 7.25 (m, 5H), 4.02 (s, 1.44H), 3.96 (s, 0.56H), 3.58 (m, 2H), 2.84 (m, 2H), 2.74 (t, J=8 Hz, 0.56H), 2.63 (t, J=8 Hz, 1.44H), 2.33 (t, J=7Hz, 0.56H), 2.14 (t, J=7 Hz, 1.44H), 1.94 (m, 0.56H), 1.79 (m, 1.44H).

10-11

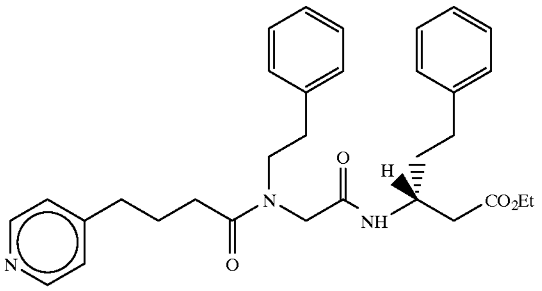

4-(Pyridin-4-yl)butanoyl-N-(2-phenylethyl)glycyl-3(R)-(2-phenethyl)-β-alanine ethyl ester (10-11)

A solution of acid 10-10 (160 mg, 0.4903 mmol) amine 7-5 (164 mg, 0.49 mmol), NMM (216 μl, 1.96 mmol), BOP reagent (239 mg, 0.539 mmol) and $CH_3CN$ (5 ml) was stirred at ambient temperature for 18 h. The reaction was diluted with EtOAc and then washed with sat. $NaHCO_3$, brine, dried ($MgSO_4$) and concentrated. Flash chromatography (silica, EtOAc) furnished ester 10-11 (220 mg) as a colorless oil.

TLC $R_f$=0.21 (silica, EtOAc)

$^1$H NMR (400 MHz, $CD_3OD$) δ 8.37 (m, 2H), 7.24 (m, 12H), 4.23 (m, 1H), 4.06 (m, 2H), 3.95 (m, 2H), 2.84 (m,

2H), 2.56 (m, 6H), 2.34 (t, J=7 Hz, 0.56H), 2.16 (t, J=7 Hz, 1.44H), 1.83 (m, 0.56H), 1.81 (m, 1.44H), 1.91 (m, 3H).

10-12

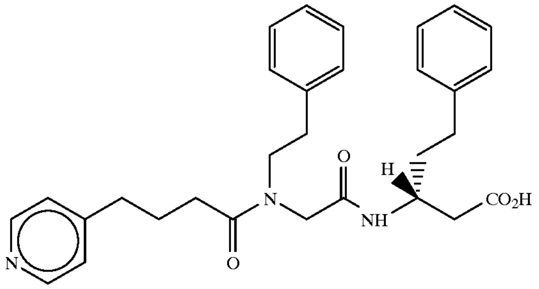

4-(Pyridin-4-yl)butanoyl-N-(2-phenyl)glycyl-3(R)-(2-phenethyl)-β-alanine (10-12)

A solution of ester 10-11 (200 mg, 0.3778 mmole), IN NaOH (0.5 ml, 0.5 mmol) and $CH_3OH$ was stirred at ambient temperature for 1.5 h followed by concentration. The crude acid was dissolved in $H_2O$, acidified with conc. HCl, concentrated and then azeotroped with toluene. Flash chromatography (silica, 20:20:1:1 EtOAc/EtOH/$NH_4OH$/$H_2O$) furnished acid 10-12 (100 mg) as a white solid.

TLC $R_f$ 0.18 (20:20:1:1 EtOAc/EtOH/$NH_4OH$/$H_2O$)

$^1H$ NMR (400 MHz, $D_2O$) δ8.47 (d, J=6 Hz, 1.36H), 8.43 (d, J=6 Hz, 0.64H), 7.71 (d, J=6 Hz, 0.64H), 7.66 (d, J=6 Hz, 1.36H), 7.20 (m, 10H), 4.07 (m, 1H), 3.81 (s, 1.36H), 3.73 (d, J=6 Hz, 0.64H), 3.51 (bt, 1.36H), 3.43 (m, 0.64H), 2.73 (m, 3H), 2.60 (t, J=7 Hz, 1.36H), 2.53 (m, 3.64H), 2.18 (t, J=7 Hz, 0.64H), 1.78 (m, 5.36H).

SCHEME 11

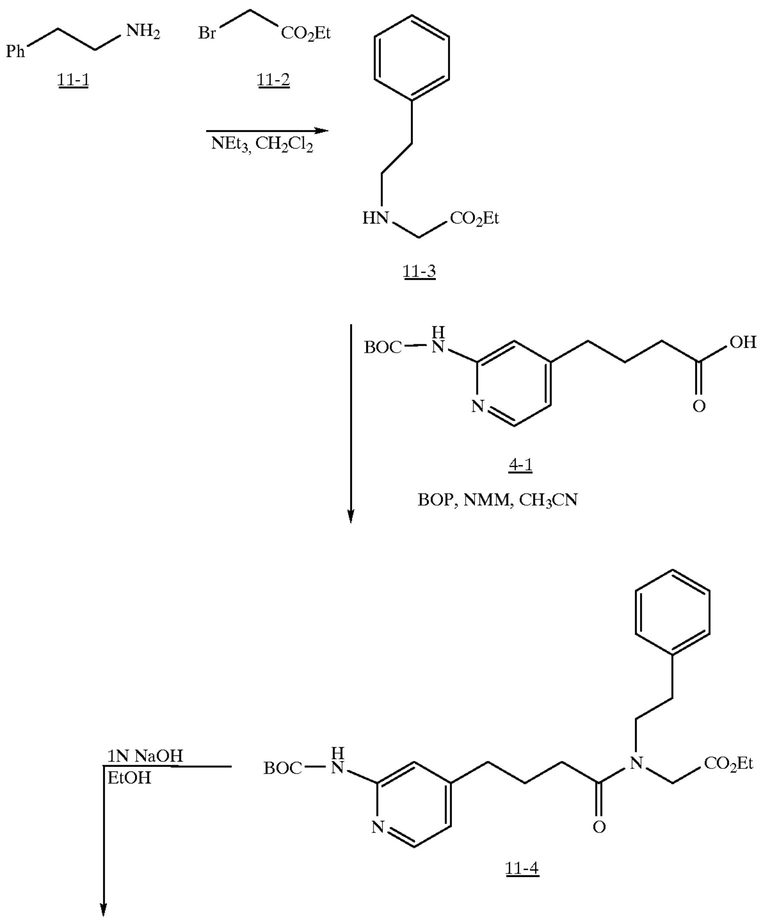

-continued
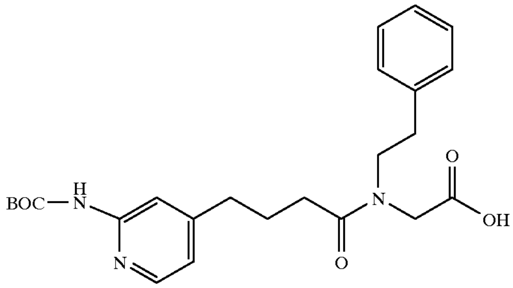
11-5
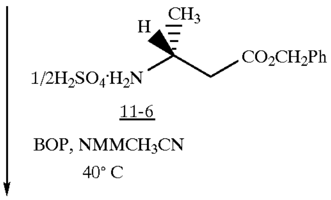
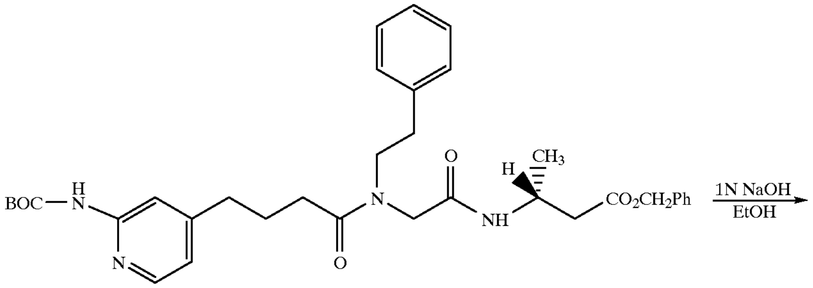
11-7
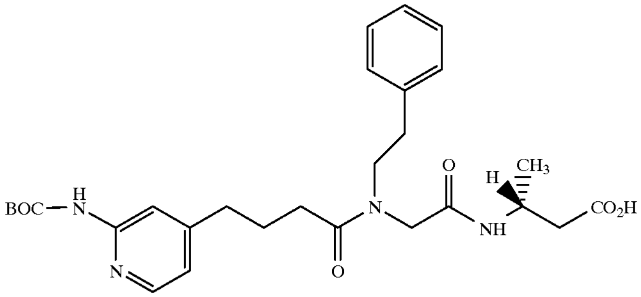
11-8
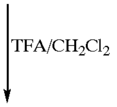

-continued

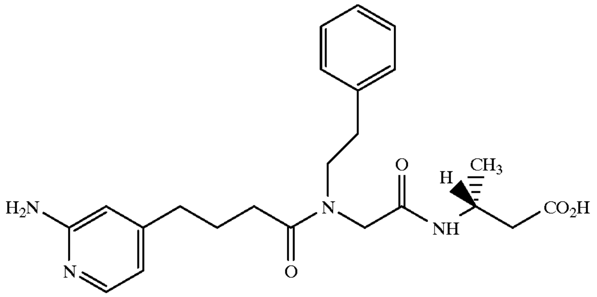

11-9

11-3

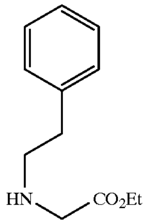

N-(2-Phenethyl)glycine ethyl ester (11-3)

A solution of amine 11-1 (20.0 g, 165 mmol), $NEt_3$ (47 ml, 330 mmol) in $CH_2Cl_2$ at 0° C. was treated with bromide 11-2 (22.4 ml, 182 mmol) followed by the removal of the cooling bath. After 1.0 h, the solution was washed with sat. $NaHCO_3$, brine, dried ($MgSO_4$) and concentrated. Flash chromatography (silica, 50% EtOAc/hexanes) afforded ester 11-3 as a yellow oil.

TLC $R_f$ 0.25 (silica, 50% EtOAc/hexanes)

$^1H$ NMR (400 MHz, $CD_3OD$) 7.25 (m, 5H), 4.15 (q, J=7 Hz, 2H), 3.37 (s, 2H), 2.81 (m, 4H), 1.23 (t, J=7 Hz, 3H).

11-4

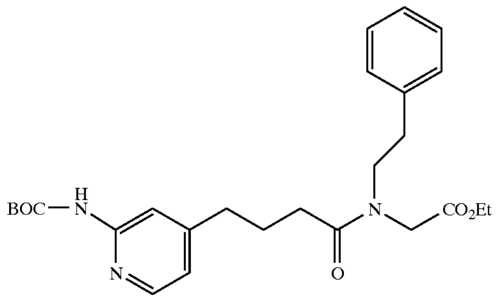

[4-(2-Boc-aminopyridin-4-yl)butanoyl]-N-(2-phenethyl)glycine ethyl ester (11-4)

A solution of acid 4-1 (1.5 g, 5.35 mmol), amine 11-3 (1.66 g, 8.03 mmol), BOP reagent (2.61 g, 5.89 mmol), NMM (3.0 ml, 1.4 mmol) and $CH_3CN$ (30 ml) was stirred at ambient temperature for 18 h. The solution was diluted with EtOAc and then washed with $H_2O$, sat. $NaHCO_3$, 10% $KHSO_4$, brine, dried ($MgSO_4$) and concentrated. Flash chromatography (silica, 50% EtOAc/hexanes 80% EtOAc/hexanes) furnished ester 11-4 as a yellow solid.

TLC $R_f$ 0.35 (silica, 50% EtOAc/hexanes)

$^1H$ NMR (400 MHz, $CDCl_3$) δ 8.12 (d, J=5 Hz, 1H), 7.77 (m, 2H), 7.21 (m, 4H), 7.10 (d, J=7 Hz, 1H), 6.79 (m, 1H), 4.18 (q, J=7 Hz, 2H), 4.02 (s, 2H), 3.58 (m, 2H), 2.82 (m, 2H), 2.62 (t, J=7 Hz, 0.64 H), 2.57 (t, J=7 Hz, 1.36H), 2.15 (m, 2H), 1.91 (m, 2H), 1.52 (s, 9H), 1.27 (m, 3H).

11-5

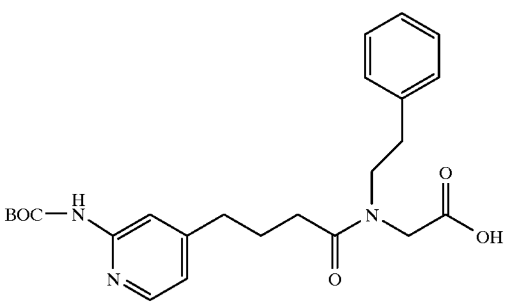

[4-(2-BOC-Aminopyridin-4-yl)butanoyl]-N-(2-phenethyl)glycine (11-5)

A solution of ester 11-4 (1.8 g, 3.84 mmol), 1N NaOH (6 ml, 6 mmol) and EtOH (10 ml) was stirred at ambient temperature for 30 minutes. The solution was acidified with 10% $KHSO_4$ and then extracted with EtOAc. The EtOAc phase was washed with brine, dried ($MgSO_4$) and concentrated to furnish acid 11-5 as a yellow solid.

TLC $R_f$ 0.80 (silica, 20:1:1 $CH_2Cl_2$/MeOH/AcOH)

$^1H$ NMR (400 MHz, $CD_3OD$) δ 8.12 (m, 1H), 7.17–7.29 (m, 7H), 4.06 (m, 2H), 3.61 (t, J=7 Hz, 2H), 2.85 (t, J=7 Hz, 2H), 2.81 (m, 0.64H), 2.63 (t, J=8Hz, 1.36H), 2.35 (t, J=7Hz, 0.64H), 2.14 (t, J=7 Hz, 1.36H), 1.79 (m, 2H), 1.57 (s, 9H).

11-7

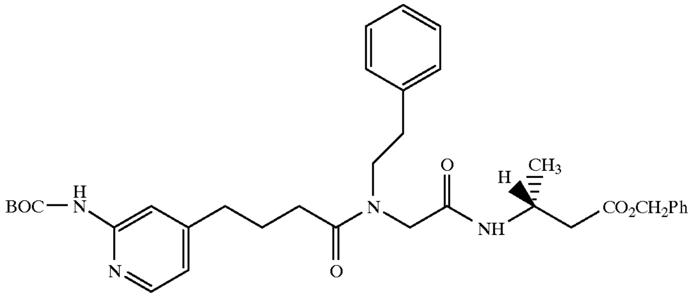

4-(2-BOC-Aminopyridin-4-yl)butanoyl-N-(2-phenethyl)glycyl-3(R)-methyl-β-alanine benzyl ester (1 1-7)

A solution of acid 11-5 (400 mg, 0.91 mmol), amine 11-6 (available from Celgene) (285 mg, 1.09 mmol), BOP reagent (440 mg, 0.997 mmol), NMM (502 μl, 3.63 mmol) and $CH_3CN$ (20 ml) was stirred at ambient temperature for 18 h. The solution was diluted with EtOAc and then washed with $H_2O$, sat. $NaHCO_3$, 10% $KHSO_4$, brine, dried ($MgSO_4$) and then concentrated. Flash chromatography (silica, 90% EtOAc/hexanes) furnished benzyl ester 11-7 as a yellow oil.

TLC $R_f$ 0.49 (silica, EtOAc)

$^1H$ NMR (400 MHz, $CD_3OD$) δ 8.06 (d, J=5 Hz, 1H), 7.7 (s, 0.32H), 7.68 (s, 0.68H), 7.09–7.36 (m, 10H), 6.83 (m, 1H), 5.16 (s, 1.36H), 5.08 (s, 0.64H), 4.29 (m, 1H), 3.93 (m, 2H), 3.51 (t, J=7 Hz, 2H), 2.79 (q, J=7 Hz, 2H), 2.50–2.61 (m, 4H), 2.25 (t, J=8 Hz, 0.64H), 2.09 (t, J=7 Hz, 1.36H), 1.73–1.84 (m, 4H), 1.51 (s, 9H), 1.25 (d, J=7 Hz, 3H).

11-8

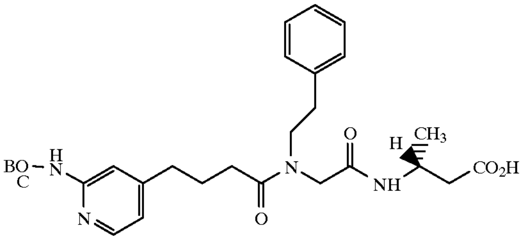

4-(2-BOC-Aminopyridin-4-yl)butanoyl-N-(2-phenethyl)glycyl-3(R)-methyl-β-alanine (11-8)

A solution of benzyl ester 11-7 (380 mg, 0.597 mmol), 1N NaOH (1 ml, 1.0 mmol) and EtOH (5 ml) was stirred at ambient temperature for 1.0 h. The solution was acidified with 10% $KHSO_4$ and then extracted with EtOAc. The EtOAc phase was washed with brine, dried ($MgSO_4$) and concentrated to furnish acid 11-8 as a yellow oil.

$^1H$ NMR (400 MHz, $CD_3OD$) δ 8.13 (m, 1H), 7.15–7.35 (m, 7H), 4.24 (m, 1H), 3.91 (m, 2H), 3.58 (m, 2H), 2.81 (m, 2.64H), 2.62 (t, J=8 Hz, 1.36H), 2.36 (t, J=7 Hz, 0.64H), 2.14 (t, J=7 Hz, 1.36H), 1.79 (m, 2H), 1.57 (s, 9H), 1.19 (m, 3H).

11-9

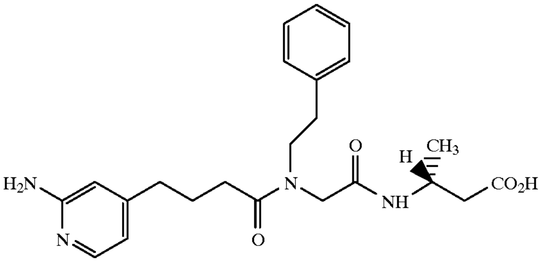

4-(2-Aminopyridin-4-yl)butanoyl-N-(2-phenethyl) glycyl-3(R)-methyl-β-alanine (11-9)

A solution of acid 11-8 (320 mg, 0.59 mmol) in $CH_2Cl_2$ (5 ml) was treated with TFA (5 ml). After 1.0 h, the solution was concentrated and then azeotroped with toluene. Flash chromatography (silica, 10:10:1:1 EtOAc/EtOH/$NH_4OH$/$H_2O$) furnished amine 11-10 (210 mg) as a white solid.

TLC $R_f$=0.28 (silica, 5:5:.5:.5 EtOAc/EtOH/$NH_4OH$/$H_2O$)

$^1H$ NMR (400 MHz, $CD_3ODD$) δ 7.71 (d, J=6 Hz, 1H), 7.15–7.32 (m, 5H), 6.62–6.69 (m, 2H), 4.25 (m, 1H), 3.99 (m, 2H), 3.58 (t, J=7 Hz, 2H), 2.81 (m, 2H), 2.61 (t, J=7 Hz, 0.64H), 2.31–2.51 (m, 3.36H), 2.12 (td, J=3 Hz, 7 Hz, 1.36H), 1.89 (t, J=8 Hz, 0.64H), 1.79 (m, 2H), 1.19 (m, 3H).

SCHEME 12
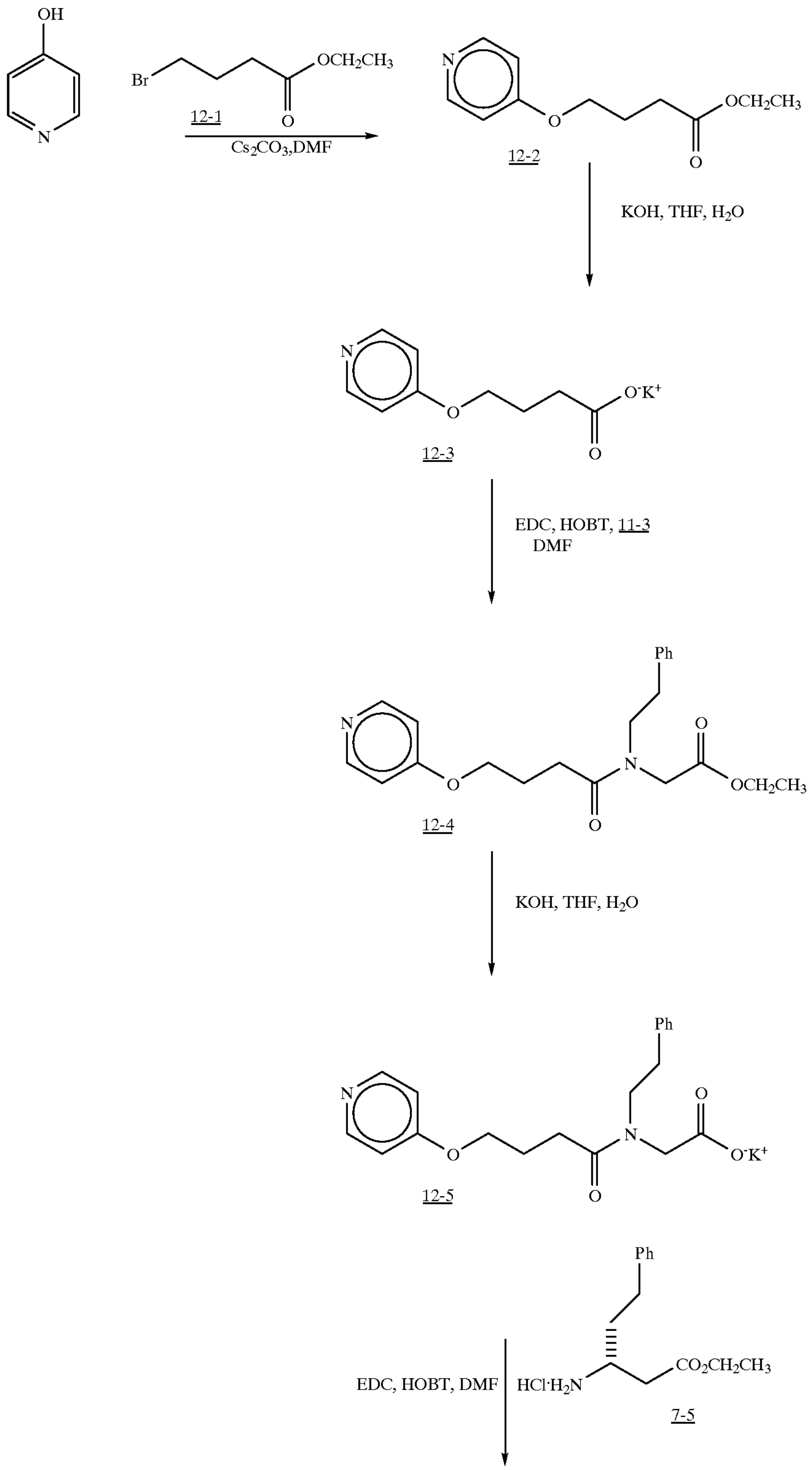
12-1 12-2 12-3 12-4 12-5 7-5

-continued

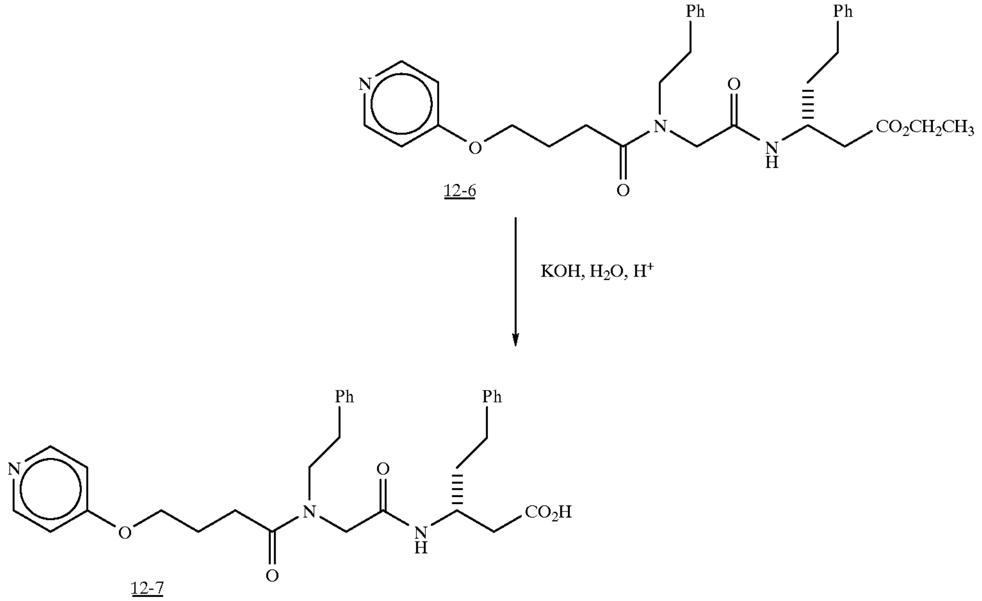

12-6

12-7

12-1

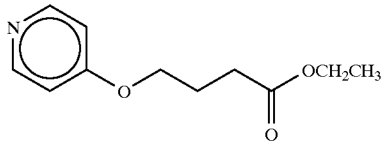

Ethyl-4-(4-Pyridyloxy)butyrate (12-2)

A mixture of 4-hydroxypyridine (10 g, 105 mmol), ethyl 4-bromobutyrate 12-1 (15.0 ml, 105 mmol) and $Cs_2CO_3$ (34.2 g, 105 mmol) in DMF (100 ml) was stirred at room temperature for 24 h. The reaction was filtered and the filtrate diluted with ethyl acetate (300 ml) and washed with water (4×100 ml) and brine (100 ml) then dried ($Na_2$ $SO_4$), filtered, and evaporated. The resulting oil was purified by chromatography on silica gel (3% $CH_3OH/CH_2Cl_2$) to give 12-2 as a colorless glass.

TLC $R_f$ 0.45 (silica, 5% $CH_3OH/CH_2Cl_2$)

$^1H$ NMR (300 MHz, $CDCl_3$) δ 8.41 (d, J=6.8 Hz, 2H), 6.83 (d, J=6 Hz, 2H), 4.16 (q, J=7 Hz, 2H), 4.07 (t, J=7 Hz, 2H), 2.52 (t, J=7 Hz, 2H), 2.81 (t, J=7 Hz, 2H), 1.23 (t, J=7.0 Hz, 3H).

12-3

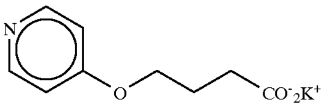

Potassium 4-(4-pyridyloxy)butyrate (12-3)

The ester 12-1 (2.5 g, 12.0 mmol) was dissolved in 10 ml THF and treated with 0.5 N KOH (24 ml, 12.0 mmol) and $H_2O$ (10 ml). The resulting solution was stirred at room temperature for 78 h then evaporated at reduced pressure to give 12-2 as a white solid.

$^1H$ NMR (300 MHz, $D_2O$) δ 8.19 (d, J=6.8 Hz, 2H), 6.83 (d, J=6.8 Hz, 2H), 6.83 (d, J=6.8 Hz, 2H), 3.96 (t, J=7.1 Hz, 2H), 2.18 (t, J=7.1 Hz, 2H), 1.93 (m, 2H).

12-4

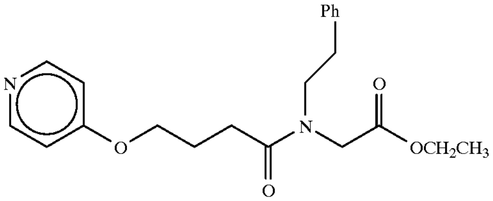

4-(4-Pyridyloxy)butyrate-N-(2-phenethyl)glycine ethyl ester (12-4)

The alkoxy pyridine 12-3 (298 mg, 1.36 mmol) and amine 11-3 (450 mg, 1.36 mmol) were combined with EDC (260 mg, 136 mmol), HOBT (208 mg, 136 mmol), in DMF (30 ml) and stirred at room temperature for 16 h. The solution was then diluted with ethyl acetate (200 ml) and washed with sat. $NaHCO_3$ (2×100 ml) and brine (100 ml). The organic layer was dried ($Na_2SO_4$), filtered, and evaporated and the residue chromatographed on silica gel (3% $CH_3OH/CH_2Cl_2$) to give 12-4 as a colorless glass.

$^1H$ NMR (300 MHz, $CDCl_3$) δ 8.41 (d, J=6.5 Hz, 2H), 7.25 (m, 5H), 6.78 (d, J=6.5 Hz, 2H), 61.23 (m, 2H), 4.02 (s, 2H), 4.00 (m, 2H), 3.63 (m, 2H), 3.41 (m, 2H), 2.15 (m, 2H), 1.31 (m, 3H).

12-5

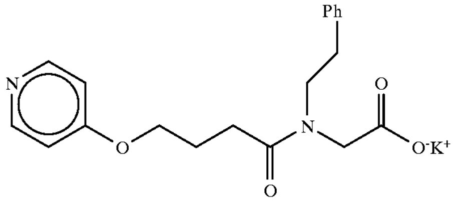

4-(4-Pyridyloxy)butyrate-N-(2-phenethyl)glycine potassium salt (12-5)

Ester 12-4 (360 mg, 0.97 mmol) was hydrolyzed in 0.5 N KOH (1.94 ml, 0.97 mmol) to give the potassium salt 12-5 as a white solid.

$^1$H NMR (300 MHz, DMSO-$d_6$) δ 8.38 (d, J=6.5 Hz, 2H), 7.25 (m, 5H), 6.93 (d, J=6.5 Hz, 2H), 4.016 m, 2H), 3.45 (m, 2H), 3.25 (s, 2H), 2.68 (m, 2H), 2.21 (m, 2H), 1.86 (m, 2H).

12-6

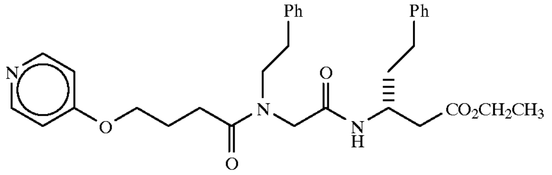

4-(Pyridyloxy)butyrate -N-(2-phenethyl)glycyl-3 (R)-2-phenethyl-β-alanine ethyl ester (12-6)

Acid salt 12-5 (352 mg, 0.93 mmol) and amino ester 7-5 (240 mg, 193 mmol), HOBT (142 mg, 0.93 mmol), EDC (198 mg, 0.93 mmol), and triethylamine (130 μl, 0.93 mmol) was dissolved in DMF (15 ml) and stirred at room temperature for 18 h. The solution was diluted with ethyl acetate (200 ml) washed with sat. $NaHCO_3$, water and brine (100 ml each), dried ($Na_2SO_4$) and concentrated to give a colorless oil. Chromatography on silica gel afforded 12-6 as a colorless glass.

TLC $R_f$ 0.50 (silica, 3% $CH_3OH/CH_2Cl_2$)

$^1$H NMR (300 MHz, $CDCl_3$) δ 8.40 (d, J=6.6 Hz, 2H), 7.25 (m, 10H), 6.85 (t, J=7.4 Hz, 1H), 7.25 (d, J=6.6 Hz, 2H), 4.25 (m, 1H), 4.18 (m, 2H), 4.00 (m, 2H), 3.60 (m, 2H), 2.95 (m, 2H), 2.63 (m, 2H), 2.58 (m, 2H), 2.40 (m, 2H), 2.08 (m, 2H), 1.85 (m, 2H), 1.16 (m, 3H).

12-7

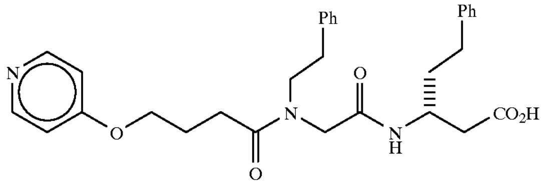

4-(4-Pyridyloxy)butyrate-N-(2-phenethyl)glycyl-3 (R)-2-phenethyl-β-alanine (12-7)

Ester 12-6 (123 mg, 0.23 mmol) was hydrolyzed with 0.5 N KOH and the acid was isolated as its TFA salt following preparative reverse phase chromatography.

$^1$H NMR (300 MHz, $CD_3OD$) δ 8.63 (d, J=6.5 Hz, 2H), 7.52 (d, J=6.5 Hz, 2H), 7.20 (m, 10H), 4.41 (m, 1H), 4.32 (m, 2H), 4.01 (m, 2H), 3.81 (m, 2H), 2.85 (m, 2H), 2.63 (m, 2H), 2.30 (m, 2H), 2.41 (m, 2H), 2.20 (m, 2H), 1.85 (m, 2H).

SCHEME 13

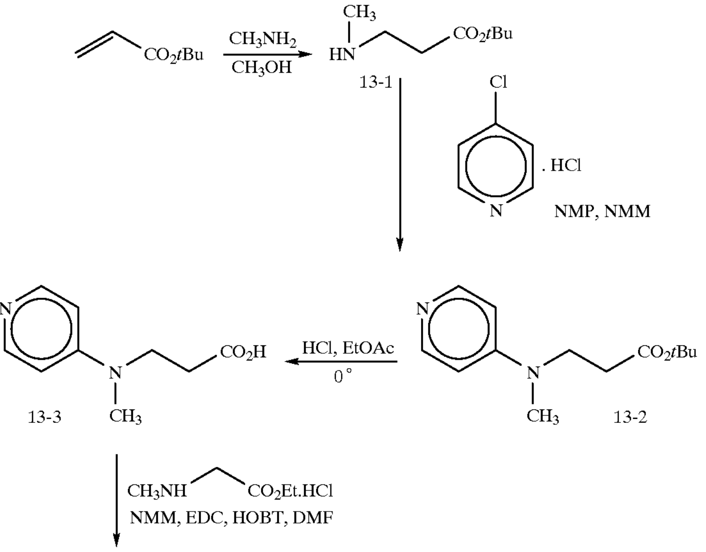

-continued

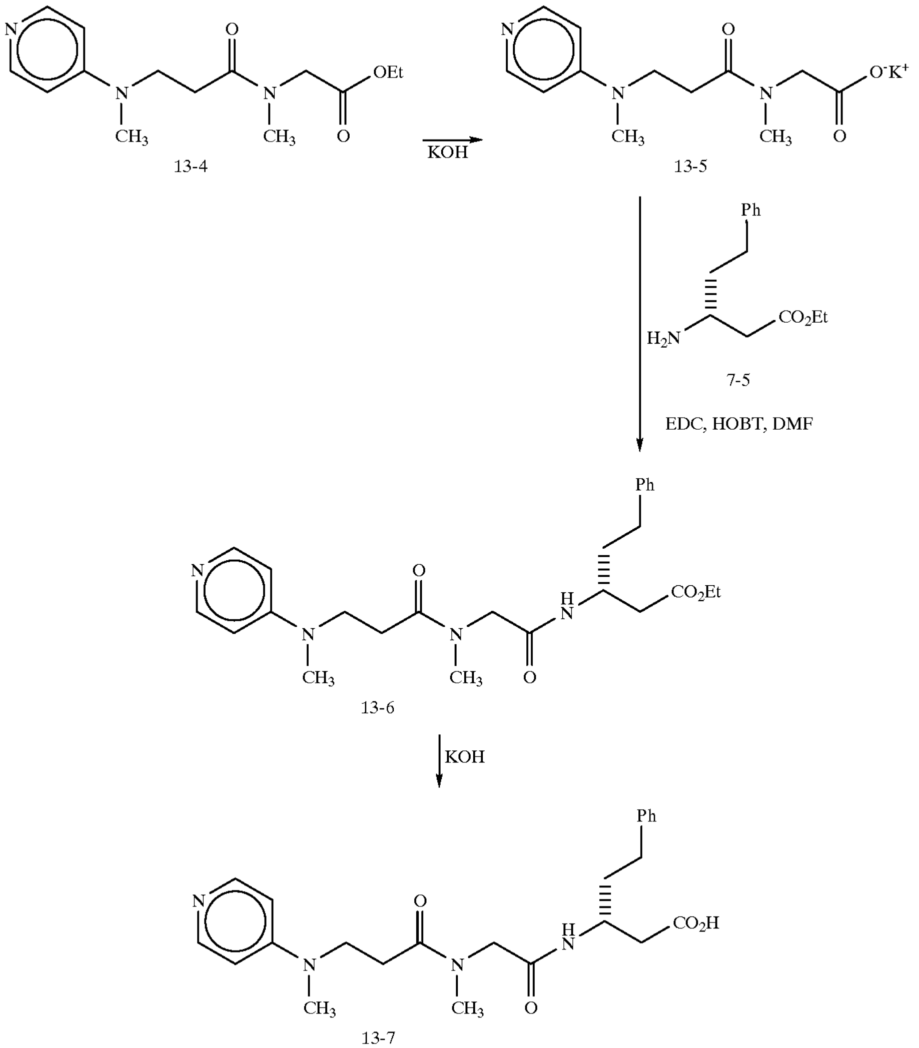

13-4 13-5 7-5 13-6 13-7

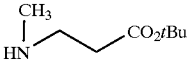

13-1 tert-Butyl 3-N-methylaminopropionate (13-1)

Tert-butyl acrylate (15 g, 117 mmol) was added to a solution or methanol saturated with $CH_3NH_2$ (300 ml) and stirred at room temperature for 16 h. The solution was evaporated to afford 13-1 as a colorless liquid.

$^1H$ NMR (300 MHz, $CDCl_3$) δ 2.81 (t, J=7.2 Hz, 2H), 2.43 (t, J=7.2 Hz, 2H), 1.45 (s, 9H).

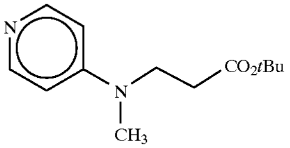

13-2 tert-Butvl 3-[(N-methyl-N-(4-pyridyl)] aminopropionate (13-2)

A mixture of 4-chloropyridine hydrochloride (10 g, 75 mmol), 13-1 (12 g, 75 mmol) and N-methylmorpholine (9.1 ml, 82.5 mmol) in N-methyl pyrrolidinone (100 ml) was heated at 120° C. for 16 h. The solvent was removed at reduced pressure and the residue partitioned between EtOAc (100 ml) and water (50 ml). The organic layer was washed with water and brine (50 ml each) then dried ($Na_2SO_4$), filtered and evaporated. The ester 13-2 was isolated as a colorless glass following flash chromatography on silica gel (5% $CH_3OH/CH_2Cl_2$).

$^1$H NMR (300 MHz, $CDCl_3$) δ 8.30 (d, J=6.8 Hz, 2H), 6.91 (d, J=6.8 Hz, 2H), 3.81 (t, J=7.1 Hz, 3H), 3.22 (s, 3H), 2.65 (t, J=7.1 Hz, 2H), 1.41 (s, 9H).

13-3

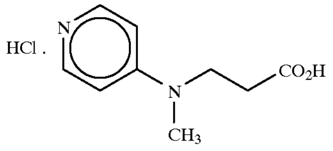

3-[(N-Methyl-N'-(4-pyridyl)]aminopropionate hydrochloride (13-3)

A solution of 13-2 (2.2 g, 9.3 mmol) in 75 ml anhydrous EtOAc was cooled to 0° and treated with HCl gas for 10 min. The solution was warmed to room temperature and stirred. For 16 h the resulting solid was filtered to give 13-3 as a hygroscopic yellow solid.

$^1$H NMR (300 mHz, DMSO-$d_6$) δ 8.26 (d, J=6.8 Hz, 2H), 7.0 (br d, 2H), 3.82 (t, J=7.1 Hz, 2H), 3.21 (s, 3H), 2.60 (t, J=7.1 Hz, 2H).

13-4

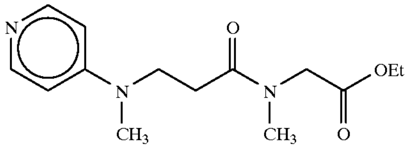

3-[(N-methyl-N-(4-pyridyl)]aminopropionyl-sarcosine ethyl ester (13-4)

Acid 13-3 (383 mg, 1.5 mmol) was coupled with sarcosine ethyl ester hydrochloride (253 mg, 1.65 mmol) following the EDC/HOBT procedure previously described to give 13-4 as a colorless glass.

TLC $R_f$ 0.45 (silica, 3% $CH_3OH/CH_2Cl_2$)

$^1$H NMR (300 MHz, $CDCl_3$) δ 8.21 (d, J=6.8 Hz, 2H), 6.51 (d, J=6.8 Hz, 2H), 4.20 (q, J=7.0 Hz, 2H), 4.18 (s, 2H), 3.75 (t, J=7.0 Hz, 2H), 3.09 (s, 3H), 3.04 (s, 3H), 2.65 (t, J=7.0 Hz, 2H), 1.31 (t, J=7.0 Hz, 3H).

13-5

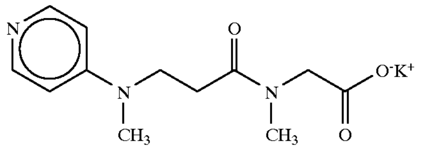

3-[(N-Methyl)-N'-(4-pyridyl)]aminopropionyl-sarcosine potassium salt (13-5)

A solution of 13-4 (353 mg, 1.26 mmol) in THF (5 ml) was treated with 0.5 N KOH (2.52 ml, 1.21 mmol) and $H_2O$ (5 ml) and stirred at room temperature for 18 h. The solvent was removed in vacuo to afford the potassium salt 13-5 as a white solid.

$^1$H NMR (300 MHz, DMSO-$d_6$) δ 8.08 (d, J=6.7 Hz, 2H), 6.57 (d, J=6.7 Hz, 2H), 3.61 (t, J=7 Hz, 2H), 3.51 (s, 2H), 2.86 (s, 3H), 2.75 (s, 3H), 2.42 (t, J=7.0 Hz, 2H).

13-6

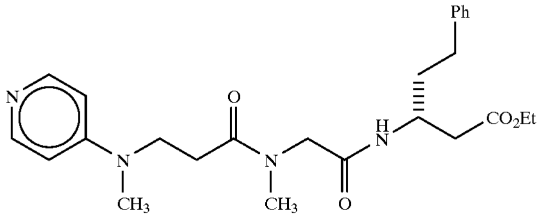

3-[(N-Methyl)-N'-(4-pyridyl)]aminopropionyl-sarcosine-3(R)-(2-phenethvl)-β-alanine ethyl ester (13-6)

The acid 13-5 was coupled with 7-5 (229 mg, 0.88 mmol) under the EDC/HOBT procedure to afford 13-6 following chromatography ($CH_2Cl_2/CH_3OH/NH_2/OH$, 90:8:2)

$^1$H NMR (300 MHz, $CDCl_3$) δ 8.21 (d, J=6.8 Hz, 2H) 7.25 (m, 2H), 6.73 (d, J=7.0 Hz, 1H), 6.51 (d, J=6.8 Hz, 2H), 4.36 (m, 1H), 61.18 (m, 2H), 3.89 (m, 2H), 3.81 (t, J=7.0 Hz, 2H), 3.06 (s, 3H), 2.98 (s, 3H), 2.85 (m, 2H), 2.65 (m, 2H), 2.51 (m, 2H), 1.83 (m, 2H), 1.20 (m, 3H).

13-7

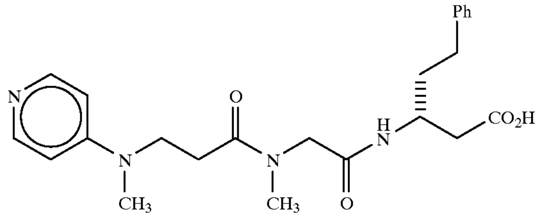

3-[(N-Methyl)-N'-(4-pyridyl)]aminopropionyl-sarcosine-3(R)-(2-phenethyl)-β-alanine (13-7)

A solution of the ester 13-6 (75 mg, 0.16 mmol) in THF (5 ml) was treated with 0.5N KOH (320 ml, 0.16 mmol) and $H_2O$ (5 ml). The resulting solution was stirred at room temperature for 7.5 h then evaporated at reduced pressure. The resulting residue was purified by reverse phase a white powder.

1H NMR (300 MHz, DMSO-$d_6$) δ 8.61 (d, J=6.8 Hz, 2H), 7.25 (m, 5H), 7.18 (d, J=7.0 Hz, 1H), 6.83 (d, J=6.8 Hz, 2H), 4.35 (m, 1H), 3.83 (m, 2H), 3.81 (t, 2H), 3.13 (s, 2H), 2.95 (s, 3H), 2.85 (m, 2H), 2.65 (m, 2H), 2.56 (m, 2H), 1.86 (m, 2H).

SCHEME 14

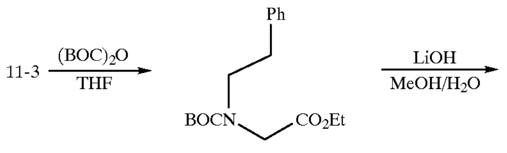

14-1

-continued

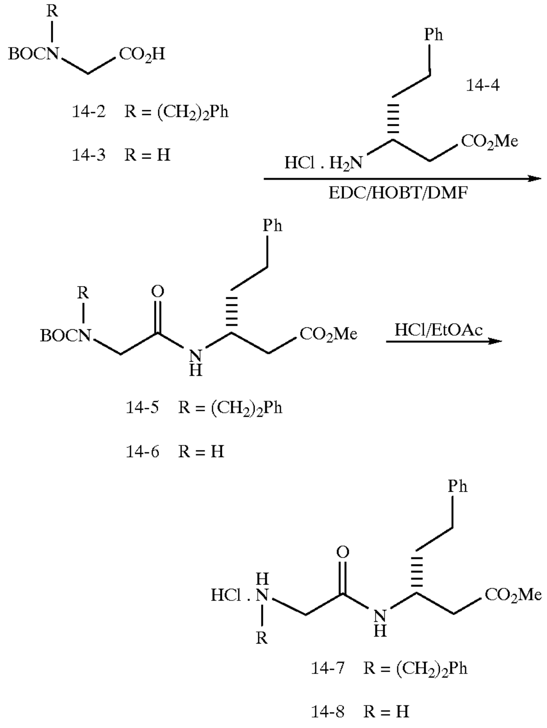

14-1

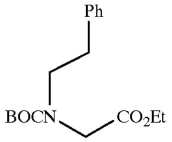

N-(t-Butoxycarbonyl)-N-(2-phenylethyl)glycine ethyl ester (14-1)

The amine 11-3 (1.11 g, 5.36 mmol) and (BOC)20 (1.28 g, 5.9 mmol) in 10 ml THF were stirred for 48 h under argon. Removal of the solvent in vacuo gave a yellow oil which was purified by chromatography (silica, hexane/EtOAc 9:1) to afford 14-1 as a colorless oil.

$R_f$ (silica, hexane/EtOAc 9:1) 0.41.

14-2

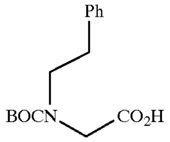

N-(t-Butoxycarbonyl)-N-(2-phenylethyl)glycine (14-2)

A solution of the ester 14-1 (1.7 g, 5.5 mmol), 11.1 mL 1N LiOH and 11 mL MeOH was stirred at room temperature for 16 h. The mixture was poured into water/EtOAc and acidified with 1N HCl to pH≈3. After extraction with EtOAc (2×), the organic layers were washed with brine, dried ($MgSO_4$) and evaporated to give 14-2 as a foam which was used as such in the next step.

14-5

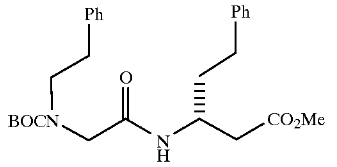

N-[N-(t-Butoxycarbonyl)-N'-(2-phenylethyl)glycyl-3 (R)-(2-phenylethyl)-β-alanine methyl ester (14-5)

The acid 14-5 (502 mg, 1.8 mmol), 3(R)-(2-phenylethyl)-β-alanine methyl ester hydrochloride 14-4 (see U.S. Pat. No. 5,291,585) (482 mg, 2.0 mmol), HOBT (267 mg, 2.0 mmol), EDC hydrochloride (515 mg, 2.7 mmol) and N-methylmorpholine (0.22 ml, 2.0 mmol) were stirred in 10 ml DMF for 16 h under argon. After pouring the solution into EtOAc/10% citric acid (aqueous solution) the mixture was extracted twice with EtOAc, washed with water then brine, dried ($MgSO_4$) and the solvent removed in vacuo. The residual yellow oil was subjected to column chromatography (silica, hexane/EtOAc 1:1 ) to give 14-5 as a colorless oil. $R_f$ (silica, hexane/EtOAc 1:1) 0.44.

14-7

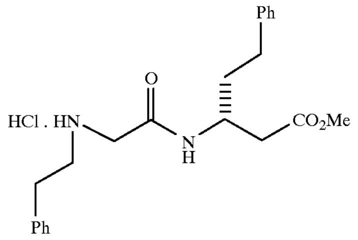

N-[N'-(2-phenethyl)glycyl]-3 (R)-(2-phenethyl)-β-alanine methyl ester hydrochloride (14-7)

A solution of 14-5 (719 mg, 1.5 mmol) in 40 mL of EtOAc as treated with HCl (g) until saturated. After 30 min the solvent was removed in vacuo and the residue was triturated with ether from which 14-10 crystallized as a white solid. $^1H$ NMR ($CD_3OD$) δ 1.87 (2H, m), 2.5–2.8 (4H, m), 3.05 (2H, m), 3.28 (2H, m), 3.62 (3H, s), 3,78 (1H, d), 3.84 (1H, d), 4.26 (1H, m), 7.1–7.4 (10H, m).

14-6

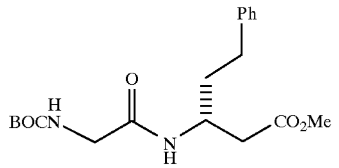

N-[N'-(t-Butoxycarbonyl)glycyl]-3(R)-(2-phenethyl)-β-alanine methyl ester (14-6)

N-(t-butoxycarbonyl)glycine 14-3 (Aldrich) was coupled with 14-4 according to the procedure described for the preparation of 14-5. The title compound 14-6 was purified by column chromatography (silica, hexane/EtOAc 1:1).

$R_f$ (silica, hexane/EtOAc 1:1) 0.22.

14-8

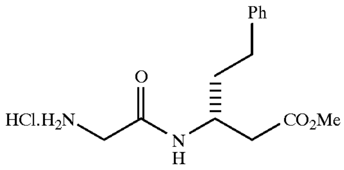

N-Glycyl-3(R)-(2-phenethyl)-β-alanine methyl ester hydrochloride (14-8)

Following the procedure described for the preparation of 14-7 compound 14-6 was converted into 14-8.

$^1$H NMR ($CD_3OD$) δ 1.88 (2H, m), 2.5–2.8 (4H, m), 3.64 (5H, s), 4.25 (1H, m), 7.1–7.3 (5H, m).

SCHEME 15

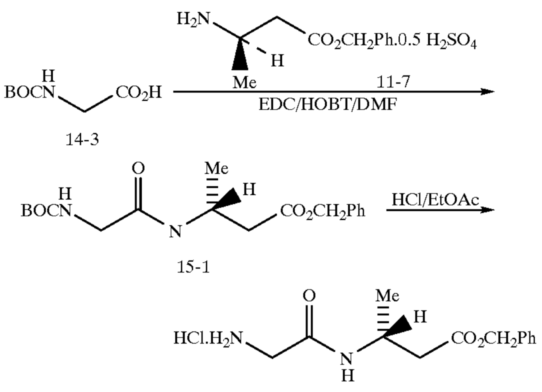

14-3

15-1

15-2

15-1

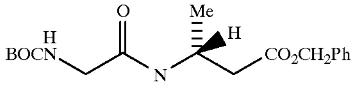

N-[N'-(t-Butoxycarbonyl)glycyl]-3(R)-methyl-β-alanine benzyl ester (15-1)

N-(t-Butoxycarbonyl)glycine 14-3 (Aldrich) was coupled with 3(R)-methyl-β-alanine benzyl ester 0.5 $H_2SO_4$ 11-7 (Celgene) according to the procedure described for the preparation of 14-5. The title product 15-1 was then obtained by chromatography (silica, hexane/EtOAc 2:3).

$R_f$ (silica, hexane/EtOAc 1:1) 0.3.

15-2

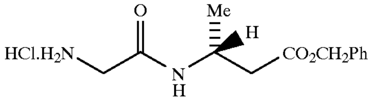

N-(Glycyl-3(R)-methyl-β-alanine benzyl ester hydrochloride (15-2)

Following the procedure for the preparation of 14-7, compound 15-1 was converted into 15-2 which was isolated as a white solid.

$^1$H NMR ($CD_3OD$) δ 1.22 (3H, d), 2.58 (2H, m), 3.53 (1H, d), 3.63 (1H, d), 6.3 (2H, s), 7.35 (5H, m).

SCHEME 16

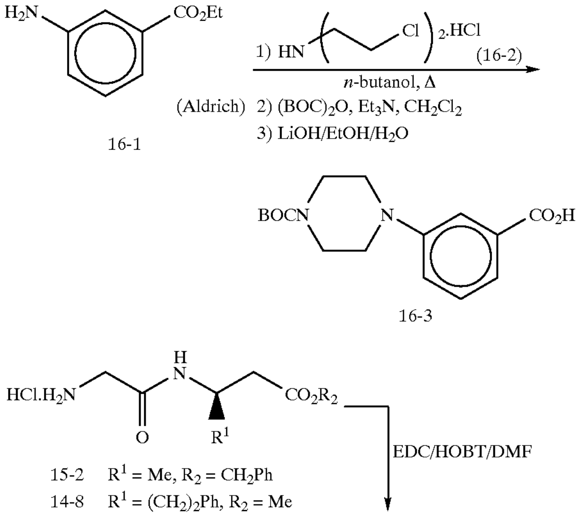

16-1

16-3

15-2 $R^1$ = Me, $R_2$ = $CH_2Ph$ 14-8 $R^1$ = $(CH_2)_2Ph$, $R_2$ = Me

-continued

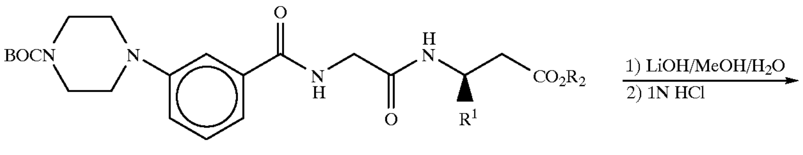

16-4 $R^1$ = Me, $R_2$ = $CH_2Ph$
16-5 $R^1$ = $(CH_2)_2Ph$, $R_2$ = Me

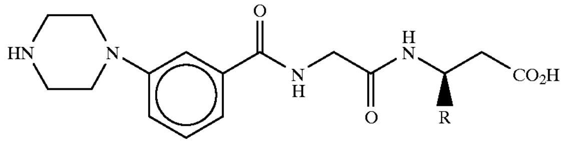

16-6 R = Me
16-7 R = $(CH_2)_2Ph$

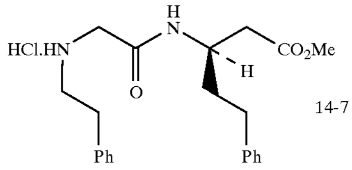

14-7

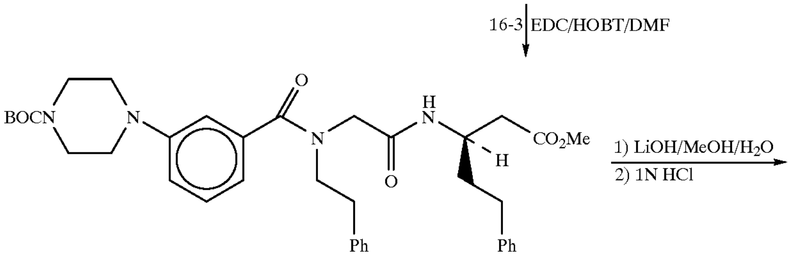

16-8

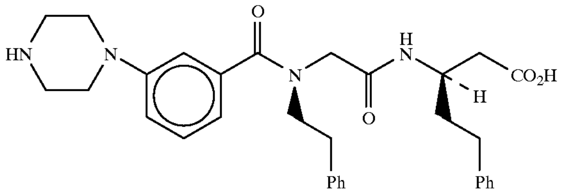

16-9

16-3

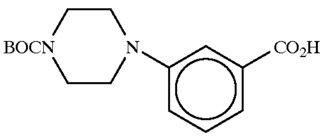

3-($^4$-t-Butoxycarbonyl-1-piperizinyl)benzoic acid (16-3)

Ethyl 3-aminobenzoate 16-1 (Aldrich, 24.3 g, 0.147 mol) and bis (2-chloroethyl)amine hydrochloride 16-2 (Aldrich, 26.3 g, 0.147 mol) were heated at reflux in 500 mL n-butanol for 24 h. The solution was concentrated in vacuo, the residue was taken up in EtOAc and washed successively with saturated aqueous $NaHCO_3$ then brine. After drying ($MgSO_4$), the solvent was removed and the resulting black oil chromatographed (silica, EtOAc then EtOAc/MeOH 1:1 then MeOH) to give the corresponding piperizine derivative as a mixture of ethyl and butyl esters.

This piperazine (17.8 g, 76 mmol) was dissolved in 500 mL dry $CH_2Cl_2$ and $Et_3N$ (13.3 ml, 95.6 mmol) was then added. To this cooled −5° C. solution was added $(BOC)_2O$ (17.4 g, 79.9 mmol) in 45 ml dry $CH_2Cl_2$ and stirring was continued until the reaction was complete (as monitored by TLC). The solution was poured into 10% citric acid solution then the organic layer was washed with water, saturated aqueous $NaHCO_3$ and brine. After drying over $MgSO_4$, the solvent was removed in vacuo to give a brown oil. Silica gel chromatography (hexane/EtOAc 1:1) gave the BOC-protected piperazine as a mixture of ethyl and butyl esters.

The BOC-protected piperazine (22.1 g) was dissolved in 150 ml 1N LiOH and 600 ml absolute ethanol and this solution was heated at reflux for 16 h. After removal of the ethanol, EtOAc and 10% citric acid solution were added. The organic layer was washed with 1N NaOH, the aqueous layer was then re-acidified with IN HCI and extracted with EtOAc. This EtOAc extract was washed with brine, dried ($MgSO_4$) and concentrated to give 16-3 as a white solid.

$R_f$ (silica, hexane/EtOAc 1:1) 0.22.

$^1H$ NMR ($CDCl_3$) δ 1.49 (9H, s), 3.21 (4H, br t), 3.61 (4H, br t), 7.16 (1H, dd), 7.36 (1H, t), 7.64 (2H, m).

16-4

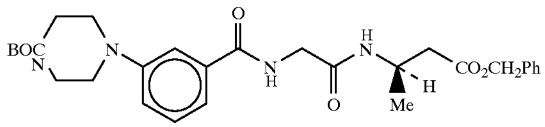

N-{N'-3-(4-t-Butoxycarbonyl-1-piperizinyl)benzoyl) glycyl}-3(R)-methyl-β-alanine benzyl ester (16-4)

The acid 16-3 was coupled with 15-2 according to the procedure described for the preparation of 14-5 to yield 16-4.

$R_f$ (silica, EtOAc) 0.45.

16-6

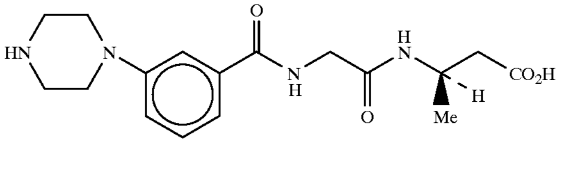

N-[N'-[3-(1-Piperazinyl)benzoy]glycyl]-3(R)-methyl-β-alanine trifluoroacetic acid salt (16-6)

The ester 16-4 (452 mg, 0.84 mmol) was dissolved in 4 ml MeOH, treated with 1N LiOH (2.5 ml, 2.5 mmol) and stirred for 48 h. The solvent was removed under reduced pressure and to the residue was added 10 ml 1N HCl. After 10 min, the solution was concentrated and the residue purified by preparative HPLC ($H_2O/CH_3CN$ with 0.1% TFA, gradient) to give 16-6.

FAB mass spectrum m/z=349 (m+1)

1H NMR ($CD_3OD$) δ 1.22 (3H, d), 2.43 (1H, dd), 2.57 (1H, dd), 3.38 (4H, m), 3.46 (4H, m), 3.96 (1H, d), 4.04 (1H, d), 4.30 (1H, sextet), 7.25 (1H, m), 7.4 (2H, m), 7.5 (1H, m).

16-5

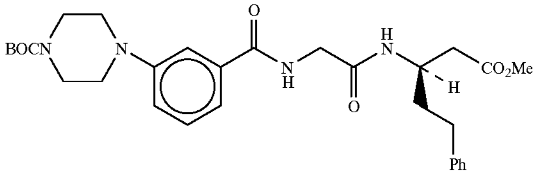

N-[N'-[3-(4-t-Butoxycarbonyl-1-piperazinyl) benzoyl]glycyl]-3(R)-(2-phenethyl)-β-alanine methyl ester (16-5)

The acid 16-3 was coupled with 14-8 according to procedure described for the preparation 14-5 to yield 16-5.

$^1H$ NMR ($CDCl_3$) δ 1.49 (9H, s), 1.90 (2H, m), 2.58 (2H, d), 2.63 (2H, m), 3.15 (6H, m), 3.55 (4H, m), 3.62 (3H, s), 4.10 (2H, d), 4.32 (1H, m), 7.0–7.5 (9H, m).

16-7

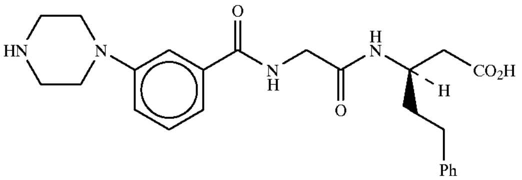

N-[N'-[3-(1-Piperazinyl)benzoyl]glycyl]-3(R)-(2-phenethyl)-β-alanine trifluoroacetic acid salt (16-7)

Following the procedure described for the preparation of 16-6, 16-5 was converted into 16-7.

FAB mass spectrum m/z=439 (m+1)

Anal. calcd. for $C_{24}$ $H_{30}N_4O_4$·1.35 TFA·1.0 $H_2O$ C, 52.53; H, 5.51; N, 9.18 found: C, 52.57; H, 5.44; N, 9.26

16-8

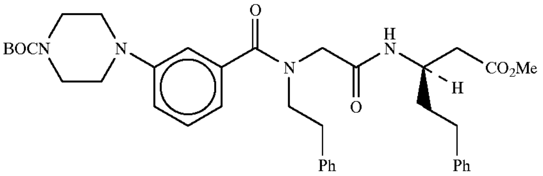

N-[N'-[3-(4-t-Butoxycarbonyl-1-piperazinyl) benzoyl]-N'-(2-phenethyl)glycyl]-3(R)-(2-phenethyl)-β-alanine methyl ester (16-8)

The acid 16-3 was coupled with 14-7 according to the procedure described for the preparation of 14-5 to yield 16-8.

$R_f$ (silcia, EtOAc/hexane 2:1) 0.37.

16-9

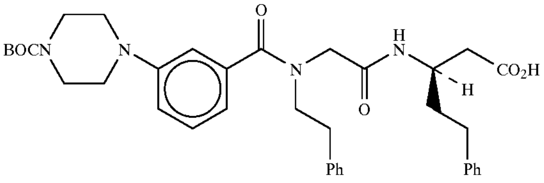

N-[N'-[3-(1-Piperazinyl)benzoyl]-N'-(2-phenethyl) glycyl]-3(R)-(2-phenethyl)-β-alanine trifluoroacetic acid salt (16-9)

Following the procedure described for the preparation of 16-6, 16-8 was converted into 16-9.

FAB mass spectrum m/z=543 (m+1)

Anal. calcd. for $C_{32}$ $H_{38}N_4O_4$·1.8 TFA·0.8 $H_2O$ C, 56.09; H, 5.47; N, 7.35 found: C, 56.09; H, 5.41; N, 7.74

SCHEME 17

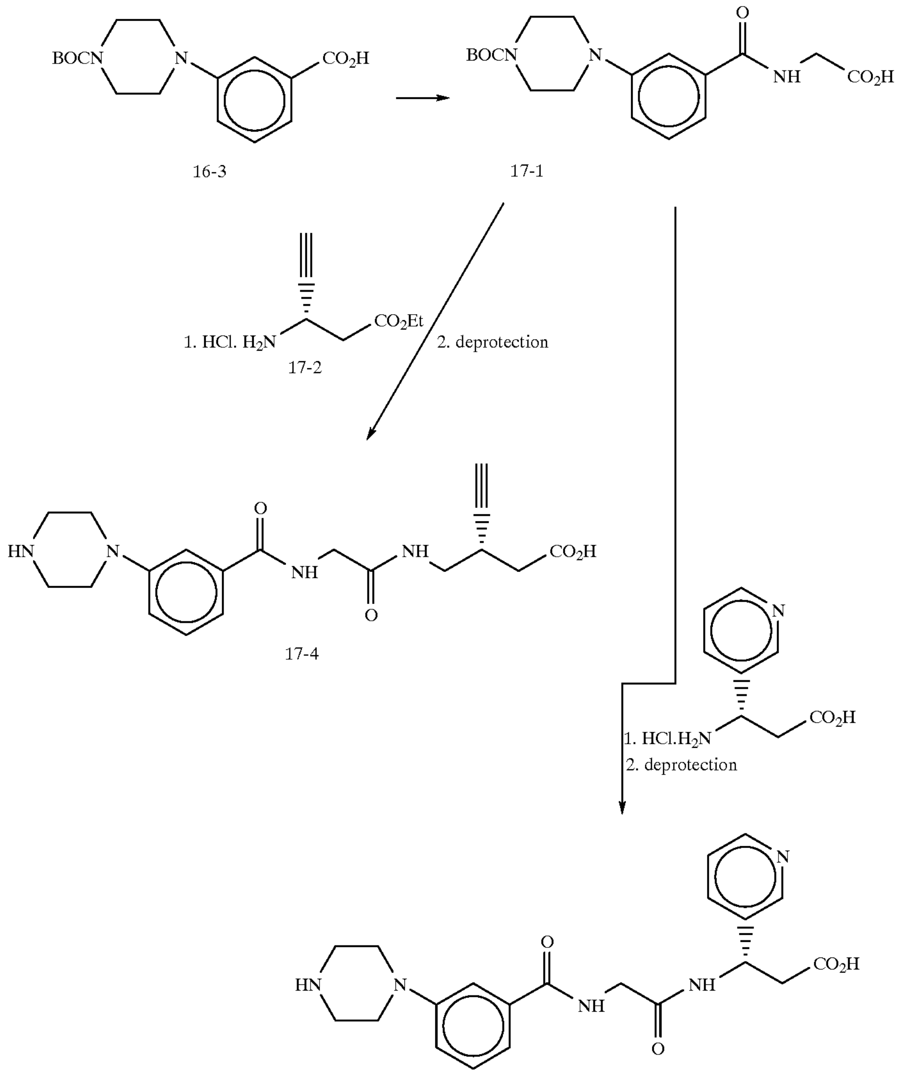

17-1

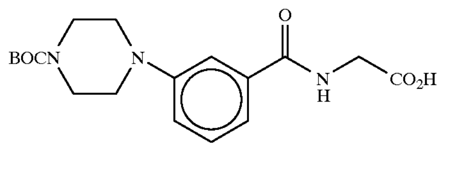

17-4

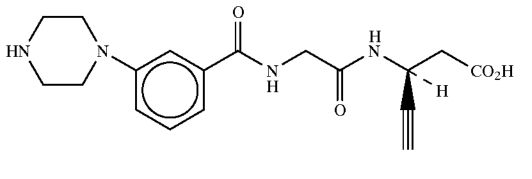

3-(4-t-Butoxycarbonyl-1-piperazinyl)benzoyl glycine (17-1)

The acid 16-3 was coupled with glycine ethyl ester followed by hydrolysis of the resulting ester using previously described chemistry to yield 17-1.

$^1H$ NMR (300 MHz, $CD_3OD$) δ 1.48 (9H, s), 3.22 (4H, m), 3.59 (4H, m), 4.08 (2H, s), 7.22 (1H, m), 7.40 (2H, m), 7.55 (1H, s).

N-[N'-[3-(1-Piperazinyl)benzoyl]glycyl]-3(S)-ethynyl-β-alanine trifluoroacetic acid salt (17-4)

The acid 17-1 was coupled with 3(S)-ethynyl-β-alanine ethyl ester hydrochloride (Zablocki et al., *J. Med. Chem.,* 1995, 38, 2378–2394) using standard peptide coupling conditions. The product was then fully deprotected using previously described methodology to give, after reverse phase chromatography, 17-4 as the trifluoroacetate salt.

FAB mass spectrum m/z=359 (M+1)

Anal. calculated for $C_{18}H_{22}N_4O_4 \cdot 1.10$ TFA$\cdot 0.30$ $H_2P$ C, 49.59; H, 4.88; N, 11.45

Found: C, 49.58; H, 4.80; N, 11.57

17-5

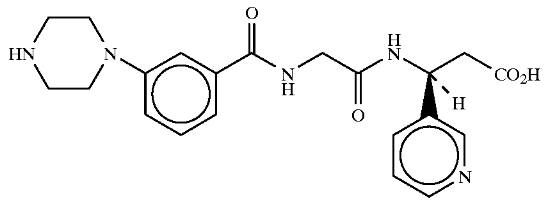

N-{N'-[3-(1-Piperazinyl)benzoyl]glycyl}-3(S)-(3-pyridyl)-β-alanine trifluoroacetic acid salt (17-5)

The acid 17-1 was coupled with 3(S)-(3-pyridyl)-β-alanine ethyl ester hydrochloride (Rico et al., *J. Org Chem.*, 1993, vol. 58, p. 7948) using standard peptide coupling conditions. The product was then fully deprotected using previously described methodology to give, after reverse phase chromatography, 17-5 as the trifluoroacetate salt.

FAB mass spectrum m/z=412 (M+1)

Anal. calculated for $C_{21}H_{25}N_5O_4 \cdot 2.55$ TFA$\cdot 0.75$ $H_2O$ C, 43.80; H, 4.09; N, 9.79

Found: C, 43.76; H, 3.98, N, 10.15

SCHEME 18

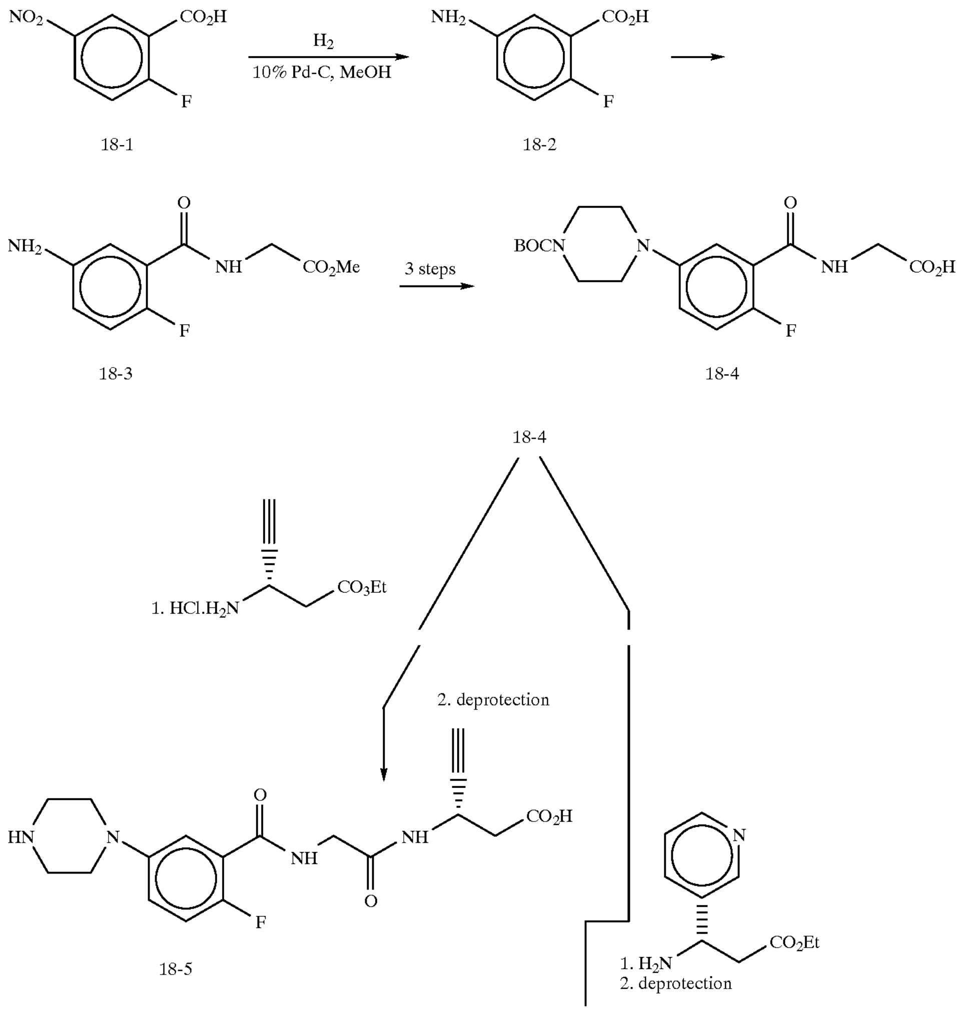

18-1

18-2

18-3

18-4

18-4

18-5

-continued

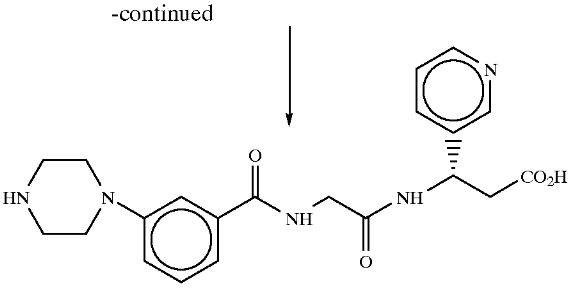

18-6

18-2

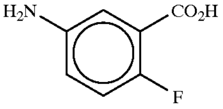

5-Amino-2-fluorobenzoic acid 18-2

2-Fluoro-5-nitrobenzoic acid 18-1 (Aldrich) was reduced using 10% Pd-C catalyst in MeOH under an atmosphere of $H_2$ to give, after filtration of the catalyst and removal of the solvent, 18-2 as a solid.

$R_f$=0.54 (silica, 10-1-1 EtOH·$NH_4OH$·$H_2O$)

18-3

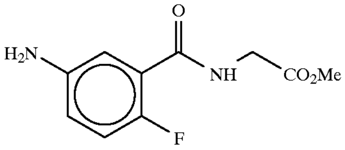

N-(5-Amino-2-Fluorobenzoyl)glycine methyl ester 18-3

The acid 18-2 was coupled with glycine methyl ester using standard peptide coupling conditions to give 18-3.

$R_f$=0.65 (silica; EtOAc/MeOH 9:1)

18-4

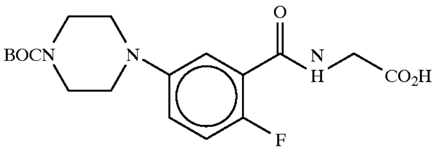

5-(4-t-Butoxycarbonyl-1-piperizinyl)-2-fluoro benzoyl glycine 18-4

Following the procedure described for the preparation of 16-3, the aniline 18-3 was converted into the piperazine-acid 18-4

$^1$H NMR (300 MHz, $CD_3OD$) δ 1.46 (9H, s), 3.11 (4H, m), 3.58 (4H, m), 4.12 (2H, s), 7.05–7.21 (2H, m), 7.40 (1H, m).

18-5

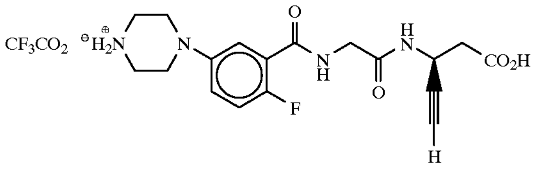

N-{N'-[2-Fluoro-5-(1-piperazinyl)benzoyl]glycyl}-3 (S)-ethynyl-β-alanine trifluoro acetic acid salt 18-5

Following the procedure described for the preparation of 17-4, compound 18-4 was converted into 18-5.

FAB mass spectrum m/z=377 (M+1)

Anal. calculated for $C_{18}H_{21}N_4O_4F$·1.30TFA·0.50 $H_2O$ C, 46.37; H, 4.40; N, 10.50

Found: C, 46.34; H, 4.37; N, 10.58

18-6

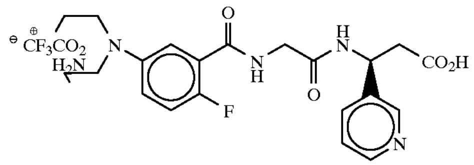

N-{N'-[2-fluoro-5-(1-piperazinyl)benzoyl]glycyl}-3 (S)-(3-pyridyl)-β-alanine trifluoroacetic acid salt 18-6

Following the procedure described for the preparation of 17-5, compound 18-4 was converted into 18-6.

FAB mass spectrum m/z=430 (M+1)

Analysis calculated for $C_{21}H_{24}N_5O_4F$·2.65 TFA·0.90$H_2O$ C, 42.24; H, 3.83; N, 9.37

Found: C, 42.25; H, 3.81; N, 9.71

SCHEME 19
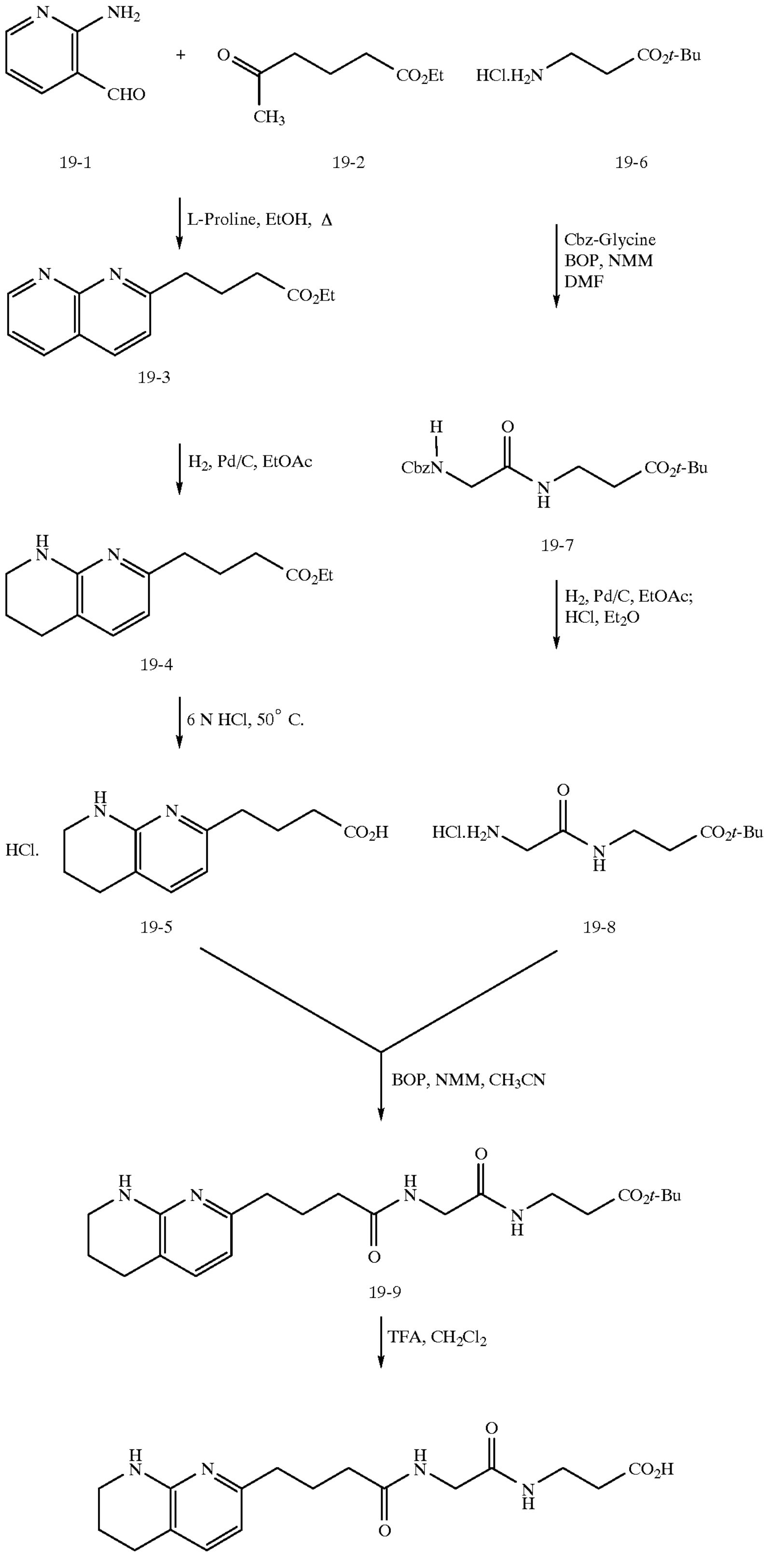
19-10

19-3

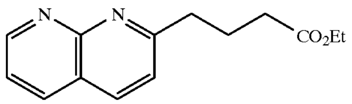

Ethyl 4-(1,8-naphthyridin-2-yl)butanoate (19-3)

Aminoaldehyde 19-1 (2.02 g, 16.6 mmol, prepared according to Het. 1993, 36, 2513), ketone 19-2 (5.3 mL, 33.1 mmol) and L-proline (0.48 g, 4.17 mmol) were combined in 75 mL EtOH. After heating at reflux overnight the reaction was concentrated. Flash chromatography (silica, EtOAc) provided 19-3 as an off-white crystalline solid.

TLC $R_f$ 0.23 (silica, EtOAc)

$^1$H NMR (300 MHz, $CDCl_3$): δ 9.09 (dd, J=4, 2Hz, 1H), 8.17 (dd, J=8, 2 Hz, 1H), 8.12 (d, J=8 Hz, 1H), 7.46 (dd, J=8, 4 Hz, 1H), 7.42 (d, J=8 Hz, 1H), 4.12 (q, J=7 Hz, 2H), 3.11 (t, J=8 Hz, 2H), 2.44 (t, J=7 Hz, 1, 1H), 2.26 (qn, J=8 Hz, 2H), 1.25 (t, J=7 Hz, 3H).

19-4

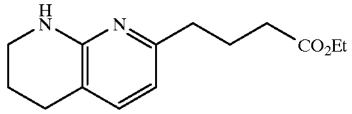

Ethyl 4-(1,2,3,4-tetrahydro-1,8-naphthyridin-7-yl) butanoate (19-4)

A solution of 19-3 (2.3 g, 9.4 mmol) in 50 mL EtOAc was treated with 10% Pd/C (230 mg) and a hydrogen balloon. After 4 d the reaction filtered through celite, concentrated, and purified by flash chromatography (silica, 70% EtOAc/hexane), providing 19-4 as a yellow oil.

TLC $R_f$ 0.40 (silica, EtOAc)

$^1$H NMR (300 MHz, $CDCl_3$): δ 7.05 (d, J=7 Hz, 1H), 6.35 (d, J=7 Hz, 1H), 4.73 (br s, 1H), 4.12 (q, J=7 Hz, 2H), 2.69 (t, J=6 Hz, 2H), 2.57 (t, J=8 Hz, 2H), 2.33 (t, J=7 Hz, 2H), 1.98 (m, 2H), 1.90 (m, 2H), 1.25 (t, J=7 Hz, 3H).

19-5

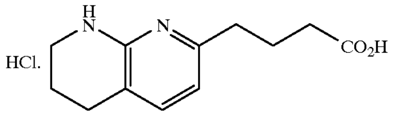

4-(1,2,3,4-Tetrahydro-1,8-naphthyridin-7-yl) butanoic acid hydrochloride (19-5)

Ester 19-4 (1.8 g, 7.25 mmol) in 36 mL 6 N HCl was heated at 50° C. for 4 h, then concentrated, providing 19-5 as a yellow solid.

$^1$H NMR (300 MHz, $CD_3OD$): δ 7.59 (d, J=7 Hz, 1H), 6.63 (d, J=7 Hz, 1H), 3.50 (t, J=5 Hz, 2H), 2.82 (t, J=6 Hz, 2H), 2.74 (t, J=8 Hz, 2H), 2.38 (t, J=7 Hz, 2H), 2.02–1.90 (m, 4H).

19-7

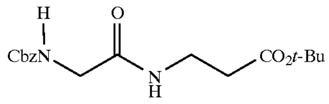

N-Cbz-Glycyl-β-alanine t-butyl ester (19-7)

N-CBz-Glycine (1.0 g, 4.78 mmol), amine 19-6 (0.91 g, 5.02 mmol), NMM (2.1 mL, 19.1 mmol) and BOP (3.17 g, 7.17 mmol) were combined in 15 mL DMF. After stirring overnight the mixture was concentrated, diluted with EtOAc, washed with water, sat. $NaHCO_3$, water, 5% $KHSO_4$ and brine, dried ($MgSO_4$), filtered and concentrated. Flash chromatography (silica, 60% EtOAc/hexane) provided 19-7 as a colorless oil.

TLC $R_f$ 0.24 (silica, 60% EtOAc/hexane)

$^1$H NMR (400 MHz, $d_6$-DMSO): δ 7.89 (br t, J=5 Hz, 1H), 7.44 (br t, J=6 Hz, 1H), 7.40–7.30 (m, 5H), 5.02 (s, 2H), 3.56 (d, J=6 Hz, 2H), 3.25 (q, J=6 Hz, 2H), 2.35 (t, J=7 Hz, 2H), 1.40 (s, 9H).

19-8

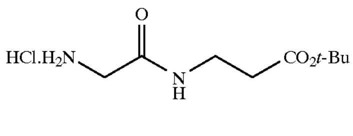

Glycyl-β-alanine t-butyl ester hydrochloride (19-8)

A solution of 19-7 (1.51 g, 4.49 mmol) in 40 mL EtOAc was treated with 10% Pd/C (0.30 g), and a $H_2$ balloon. After stirring overnight under a hydrogen atmosphere, an additional 200 mg of 10% Pd/C was added and hydrogenation was continued for 4 h before filtering through Celite and concentrating, providing the free amine as a colorless oil. The amine was dissolved in $Et_2O$ and an excess of 1 M HCl in $Et_2O$ was added. Concentration provided 19-8 as a waxy solid.

$^1$H NMR (free amine, 400 MHz, $d_6$-DMSO): δ 8.31 (br s, 1H), 5.30 (br s, 2H), 3.29 (q, J=6 Hz, 2H), 3.25 (s, 2H), 2.38 (t, J=7 Hz, 2H), 1.41 (s, 9H).

19-9

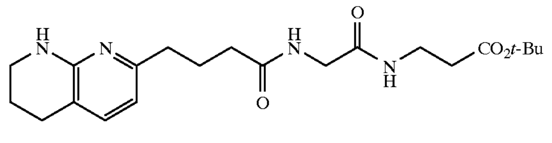

4-(1,2,3,4-Tetrahydro-1,8-naphthyridin-7-yl) butanoyl-glycyl-β-alanine t-butyl ester (19-9)

A mixture of 19-5 (62 mg, 0.24 mmol), 19-8 (69 mg, 0.29 mmol), NMM (130 μL, 1.2 mmol) and BOP (160 mg, 0.36 mmol) in 2 mL $CH_3CN$ was stirred overnight. After diluting with EtOAc the mixture was washed with sat. $NaHCO_3$, water (5×) and brine, dried ($MgSO_4$), filtered and concentrated, providing 19-9.

TLC $R_f$ 0.79 (silica, 25% $NH_3$-sat. EtOH/EtOAc)

$^1$H NMR (300 MHz, $CDCl_3$): δ 8.50 (br t, 1H), 7.08 (d, J=7 Hz, 1H), 6.64 (br t, 1H), 6.33 (d, J=7 Hz, 1H), 5.69 (br s, 1H), 3.99 (d, J=7 Hz, 2H), 3.53 (q, J=6 Hz, 2H), 3.43 (m,

2H), 2.69 (t, J=6 Hz, 2H), 2.60 (t, J=7 Hz, 2H), 2.46 (t, J=6 Hz, 2H), 2.25 (t, J=7 Hz, 2H), 2.05–1.90 (m, 4H), 1.45 (s, 9H).

19-10

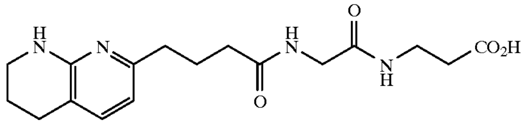

4-(1,2,3,4-Tetrahydro-1,8-naphthyridin-7-yl) butanoyl-glycyl-β-alanine ( 9-10)

Ester 19-9 (69 mg, 0.17 mmol) was dissolved in 1 mL $CH_2Cl_2$ at 0° C., 1 mL TFA was added, and the reaction was warmed to ambient temperature for 6 hr. After concentrating and azeotroping with toluene, flash chromatography (silica, 7:20:1:1 EtOAc/EtOH/$H_2O$/$NH_4OH$) provided 19-10 as a white solid.

TLC $R_f$ 0.38 (silica, 7:20:1:1 EtOAc/EtOH/$H_2O$/$NH_4OH$)

$^1H$ NMR (400 MHz, $D_2O$): δ 7.53 (d, J=7Hz, 1H), 6.59 (d, J=7Hz, 1H), 3.85 (s, 2H), 3.46 (t, J=6 Hz, 2H), 3.42 (t, J=7 Hz, 2H), 2.78 (t, J=6 Hz, 2H), 2.72 (t, J=8 Hz, 2H), 2.40 (apparent q, J=7 Hz, 4H), 2.00 (qn, J=6 Hz, 2H), 1.92 (qn, J=6 Hz, 2H).

SCHEME 20

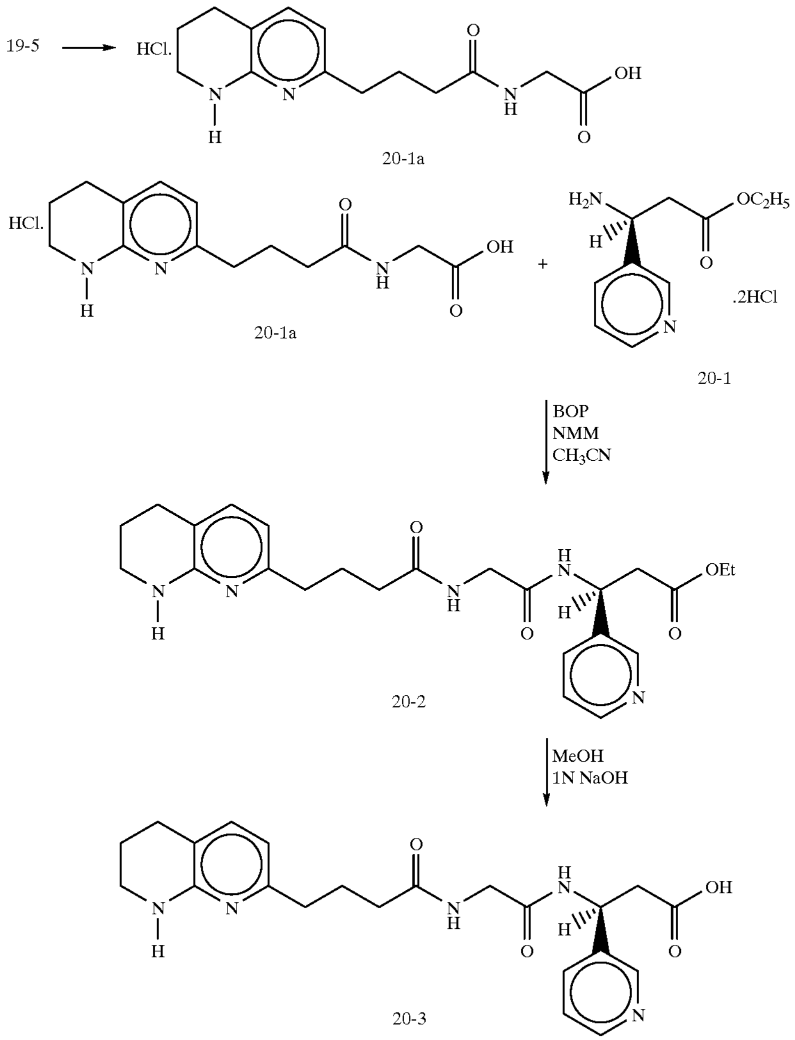

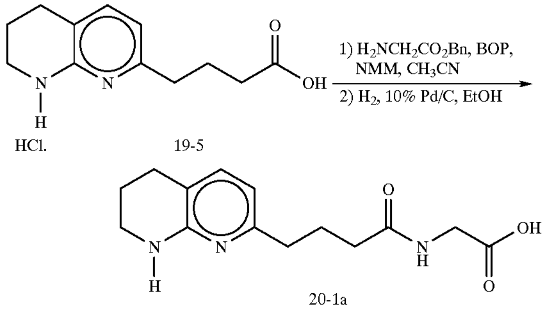

HCl. 19-5

20-1a

4-(1,2,3,4-Tetrahydro-1,8-naphthyridin-7-yl) butanoyl glycine (20-1a)

A mixture of 19-5 (1.02 g, 4.0 mmol), glycine benzyl ester (0.8 g, 4.0 mmol), NMM (1.76 ml, 16 mmol) and BOP (2.03 g, 4.6 mmol) in $CH_3CN$ (100 ml) was stirred overnight. The reaction was concentrated and the residue was partitioned between EtOAc and $H_2O$. The organic layer was washed with sat. $NaHCO_3$ solution, brine, dried ($MgSO_4$), filtered and concentrated to a yellow gum which was purified by flash chromatography (silica, 1:1, acetone/$CH_2Cl_2$) to provide the ester as a colorless gum.

A solution of the ester (1.3 g, 3.5 mmol) in EtOH (100 ml) was hydrogenated at 1 atm for 18 hr. The reaction was diluted with EtOAc (200 ml) to dissolve the product, filtered and concentrated to a solid which was sonicated with ether (100 ml) to provide 20-1a as a colorless solid.

TLC $R_f$ 0.35 (silica, EtOH/$NH_3$)

$^1$H NMR (300 MHz, $CD_3OD$): δ 7.50 (d, J=7 Hz, 2H), 6.59 (d, J=7 Hz, 2H), 3.80 (s, 2H), 3.47 (t, J=6 Hz, 2H), 2.79 (t, J=6 Hz, 2H), 2.72 (t, J=7 Hz, 2H), 2.26 (t, J=7 Hz, 2H), 2.02 (m, 2H), 1.94 (m, 2H).

4-(1,2,3,4-Tetrahydro-1,8-naphthyridin-7-yl) butanoyl-glycyl-3(S)-pyridin-3-yl-β-alanine ethyl ester (20-2)

The $CH_3CN$ solution (300 mL) of 20-1a (164 mg, 0.59 mmol), 20-1 (Rico et al., *J. Org. Chem.*, 1993, 58, 7948) (158 mg, 0.58 mmol), NMM (260 μl, 2.36 mmol) and BOP (300 mg, 0.68 mmol) was stirred under ambient conditions for 48 h. The reaction was concentrated to a yellow gum which was purified by flash chromatography (silica, 9:1 $CH_2Cl_2$/EtOH·$NH_3$) to provide 20-2 as a colorless gum.

$R_f$ 0.21 (silica, 9:1 $CH_2Cl_2$/EtOH·$NH_3$)

$^1$H NMR (300 MHz, $CD_3OD$): δ 8.53 (bs, 1H), 8.42 (d, J=5 Hz, 1H), 7.82 (d, J=8 Hz, 1H), 7.39 (dd, J=8 Hz, 5 Hz, 1H), 7.10 (d, J=8 Hz, 1H), 6.36 (d, J=7 Hz, 1H), 5.40 (t, J=7 Hz, 1H), 4.07 (q, d=7 Hz, 2H), 3.85 (s, 2H), 3.36 (t, J=6 Hz, 2H), 2.91 (m, 2H), 2.68 (t, J=6 Hz, 2H), 2.51 (t, J=7 Hz, 2H), 2.23 (t, J=7 Hz, 2H), 1.89 (m, 4H), 1.16 (t, J=7 Hz, 3H).

4-(1,2,3,4-Tetrahydro-1,8-naphthyridin-7-yl) butanoyl-glycyl-3(S)-pyridin-3-yl-β-alanine (20-3)

A methanol solution (10 mL) of 20-2 (190 mg, 0.42 mmol) and 1N NaOH (2.1 mL, 2.1 mmol) was stirred under ambient conditions for 18 h. The reaction was concentrated to dryness and the residue neutralized with 1N HCl and the resultant solution concentrated to a gum which was chromatographed (silica, 38/1/1 EtOH/$NH_4OH$/$H_2O$) to provide a solid which was purified by HPLC using a VyOAC $C_{18}$ semi prep column with gradient elution [95:5(99.9:0.1 $H_2O$/TFA)/(99.9:0.1 $CH_3CN$/TFA)→50:50 (99.9:0.1 $H_2O$/TFA)/(99.9:0.1 $CH_3CN$/TFA)80 min] to provide 20-3 as a hygroscopic solid ditrifluoroacetate salt.

$R_f$ 0.36 (silica 38:1:1 EtOH/$NH_4OH$/$H_2O$)

$^1$H NMR (300 MHz, $CD_3OD$): δ 8.79 (bs, 1H), 8.65 (d, J=5 Hz, 1H), 8.7 (d, J=8 Hz, 1H), 7.84 (m, 1H), 7.57 (d, J=7 Hz, 1H), 6.61 (d, J=7 Hz, 1H), 5.44 (t, J=7 Hz, 4H), 3.88 (m, 2H), 3.48 (t, J=5 Hz, 2H), 2.98 (d, J=7 Hz, 2H), 2.81 (t, J=6 Hz, 2H), 2.70 (m, 2H), 2.31 (m, 2H), 1.96 (m, 4H).

SCHEME 21

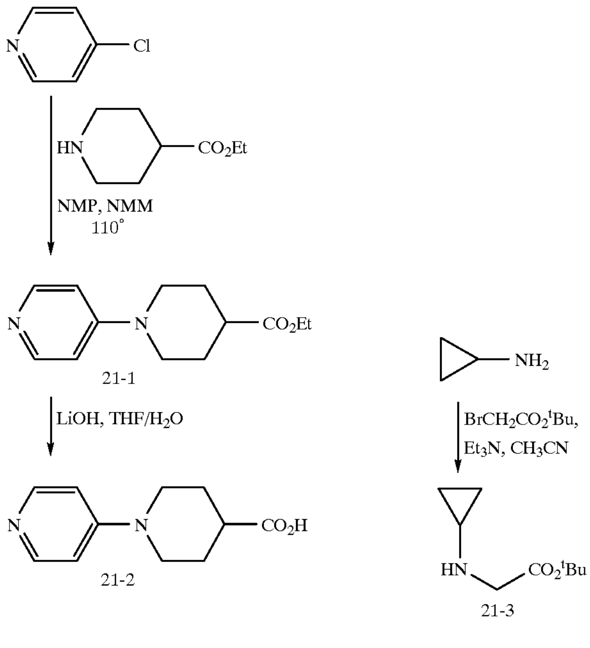

21-1

21-2

21-3

-continued

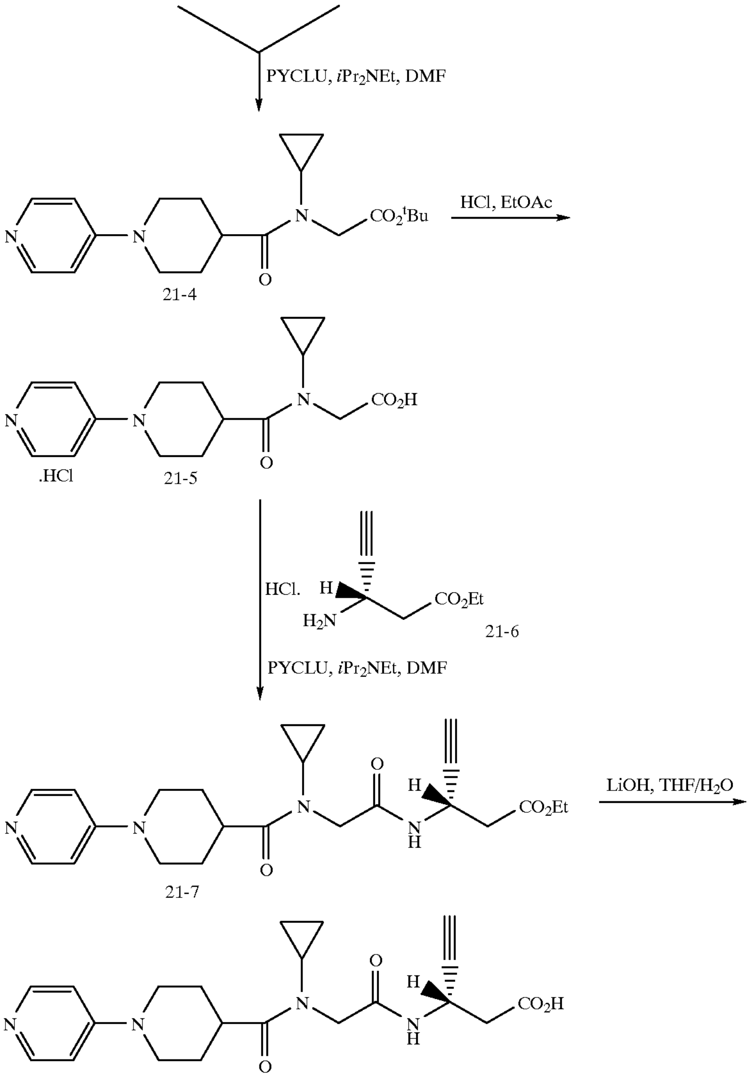

21-4

21-5

21-6

21-7

21-8

21-1

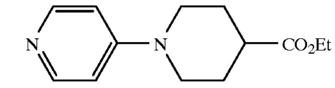

Ethyl N-pyridin-4-ylisonipecotate (21-1)

Ethyl isonipecotate (6.0 g, 38.66 mmol), 4-chloropyridine hydrochloride (5.9 g, 38.66 mmol) and N-methylmorpholine (9.3 mL, 85.0 mmol) were dissolved in N-methylpyrrolidinone (50 mL) and the resulting solution heated at 100° for 48 h. The solution was concentrated in vacuo and the residue dissolved in ethyl acetate (200 mL), washed with water and brine (2×100 mL), then dried ($Na_2SO_4$) and evaporated. The resulting residue was purified by flash chromatography (5%$MeOH/CH_2Cl_2$) to afford 21-1 as a crystalline solid.

$^1H$ NMR (300 MHz, $CDCl_3$) δ 8.21 (d, J=6.8 Hz, 2H), 6.78 (d, J=6.8 Hz, 2H), 4.18 (q, J=7.0 Hz, 2H), 3.85 (m, 2H), 3.10 (m, 2H), 2.61 (m, 1H) 2.05 (m, 2H), 1.85 (m, 2H), 1.23 (t, J=7.0 Hz, 3H).

21-2

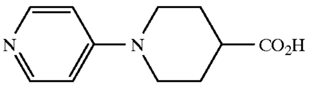

N-Pyridin-4-ylisonipecotic acid (21-2)

A solution of ester 21-1 (10 g, 42.7 mmol) in THF (50 mL) was treated with 1N LiOH (47 mL, 47.0 mmol) and $H_2O$ (50 mL). The resulting solution was concentrated and the aqueous residue cooled to 0° C., then adjusted to pH≈6 with 1N HCl and the resulting solid 21-2, collected by filtration.

$^1H$ NMR (300 MHz, $D_2O$) δ 7.95 (d, 6.8 Hz, 2H), 6.73 (d, 6.8 Hz, 2H), 3.76 (d, J=12.8 Hz, 2H), 2.81 (m, 2H), 2.20 (m, 1H), 1.85 (d, J=12.8 Hz, 2H), 1.55 (m, 2H).

$^1H$ NMR (300 MHz, $CD_3OD$) δ 8.18 (d, J=6.8 Hz, 2H), 7.18 (d, J=6.8 Hz, 2H), 4.24 (d, J=12.8 Hz, 2H), 3.95 (s, 2H), 3.21 (m, 2H), 1.95 (m, 2H), 1.85 (m, 2H), 1.62 (m, 2H), 0.87 (m, 2H), 0.75 (m, 2H).

21-3

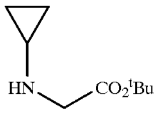

tert-Butyl-N-cyclopropylglycine (21-3)

A mixture of cyclopropylamine (10.0 g, 175.1 mmol) and triethylamine (4.9 ml, 35.5 mmol) in 100 ml $CH_2Cl_2$ was cooled to 0° and treated with tert-butyl bromoacetate (5.25 ml, 35.0 mmol). The resulting mixture was stirred at 0° C. for 2 h, refluxed for 1.5 h, then cooled and washed with sat. $NaHCO_3$, and brine (50 ml each) then dried ($Na_2SO_4$) and evaporated to afford 21-3 a colorless oil.

$^1H$ NMR (300 MHz, $CDCl_3$) δ 3.35 (s, 2H), 2.19 (m, 1H), 2.08 (br s, 1H), 1.48 (s, 9H), 0.47 (m, 2H), 0.38 (m, 2H).

21-4

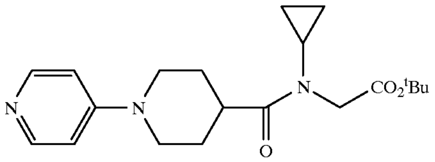

tert-Butyl N-pyridin-4-ylisonipecotyl-N-cyclopropylglycine (21-4)

A solution of acid 21-2 (500 mg, 2.36 mmol), ester 21-4 (404 mg, 2.36 mmol), chloro-N,N,N',N'-bis (pentamethylene)-formamidinium hexafluorophosphate (PYCLU) (851 mg, 2.36 mmol), and diisopropylethyl amine (305 mg, 2.36 mmol) in anhydrous DMF (50 mL) was stirred at room temperature for 18 h then concentrated in vacuo to afford a yellow residue. Chromatography on silica gel (1:1 MeOH/EtOAc) afforded 21-4 as a crystalline solid.

$^1H$ NMR (300 MHz, $CD_3OD$) δ 8.12 (d, J=6.8 Hz, 2H), 6.75 (d, J=6.8 Hz, 2H), 3.94 (d, J=12.8 Hz, 2H), 3.85 (s, 2H), 2.81 (m, 2H), 1.95 (m, 2H), 1.85 (m, 2H), 1.55 (m, 2H), 1.42 (s, 9H), 0.47 (m, 2H), 0.38 (m, 2H).

21-5

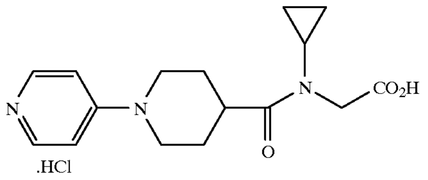

N-Pyridin-4-ylisonipecotyl-N-cyclopropylglycyl (21-5)

Ester 21-5 (250 mg, 0.70 mmol) was suspended in EtOAc (25 mL), cooled to 0° and treated with HCl gas for 15 min. The resulting solution was stirred at 0° for 3.5 h then evaporated to give 21-5 as a yellow glass.

21-7

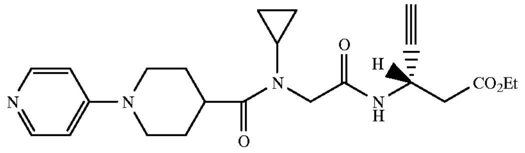

Ethyl N-pyridin-4-ylisonipecotyl-N-cyclopropylglycyl-3(S)-ethynyl-β-alanine (21-7)

A solution of acid 21-5 (232 mg, 0.68 mmol), ester 21-6 (121 mg, 0.68 mmol) (21-6 prepared as described in U.S. Pat. No. 5,272,162), PYCLU (245 mg, 0.68 mmol), and diisopropylethyl amine (176 mg, 0.68 mmol) in anhydrous DMF (50 ml) was stirred at room temperature for 18 h then concentrated in vacuo to afford a yellow residue. Preparative reverse phase chromatographic purification afforded ester 21-7 as its TFA salt.

$^1H$ NMR (300 MHz, $CD_3OD$) δ 8.48 (d, J=6.8 Hz, 1H), 8.08 (d, J=6.8 Hz, 2H), 7.18 (d, J=6.8 Hz, 2H), 5.01 (m, H), 4.24 (d, J=12.8 Hz, 2H), 4.12 (q, J=7 Hz, 2H), 3.99 (s, 2H), 3.72 (m, 1H), 3.31 (m, 2H), 2.95 (m, 1H), 2.73 (m, 2H), 1.95 (m, 2H), 1.85 (m, 2H), 1.21 (t, J=7.0 Hz, 2H), 0.87 (m, 2H), 0.75 (m, 2H).

21-8

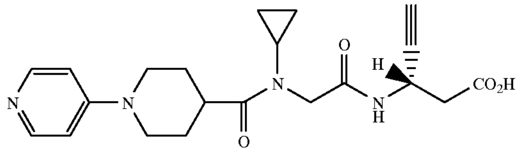

N-Pyridin-4-ylisonipecotyl-N-cyclopropylglycyl-3 (S)-ethynyl-β-alanine (21-8)

A solution of ester 21-7 (180 mg, 0.422 mmol), in THF (10 mL) was treated with 1N LiOH (0.84 mL, 0.84 mmol) and stirred at room temperature for 16 h. The mixture was concentrated and the residue purified by preparative reverse phase chromatography to afford 19-8 as its TFA salt.

$^1H$ NMR (300 MHz, $CD_3OD$) δ 8.40 (d, J=6.8 Hz, 1H), 8.21 (d, J=6.8 Hz, 2H), 7.21 (d, J=6.8 Hz, 2H), 4.81 (m, 1H), 4.22 (d, J=12.8 Hz, 2H), 3.99 (m, 2H), 3.72 (m, 1H), 3.31 (m, 2H), 2.95 (m, 1H), 2.76 (m, 1H), 2.71 (m, 2H), 1.95 (m, 2H), 1.85 (m, 2H), 0.87 (m, 2H), 0.75 (m, 2H).

SCHEME 22
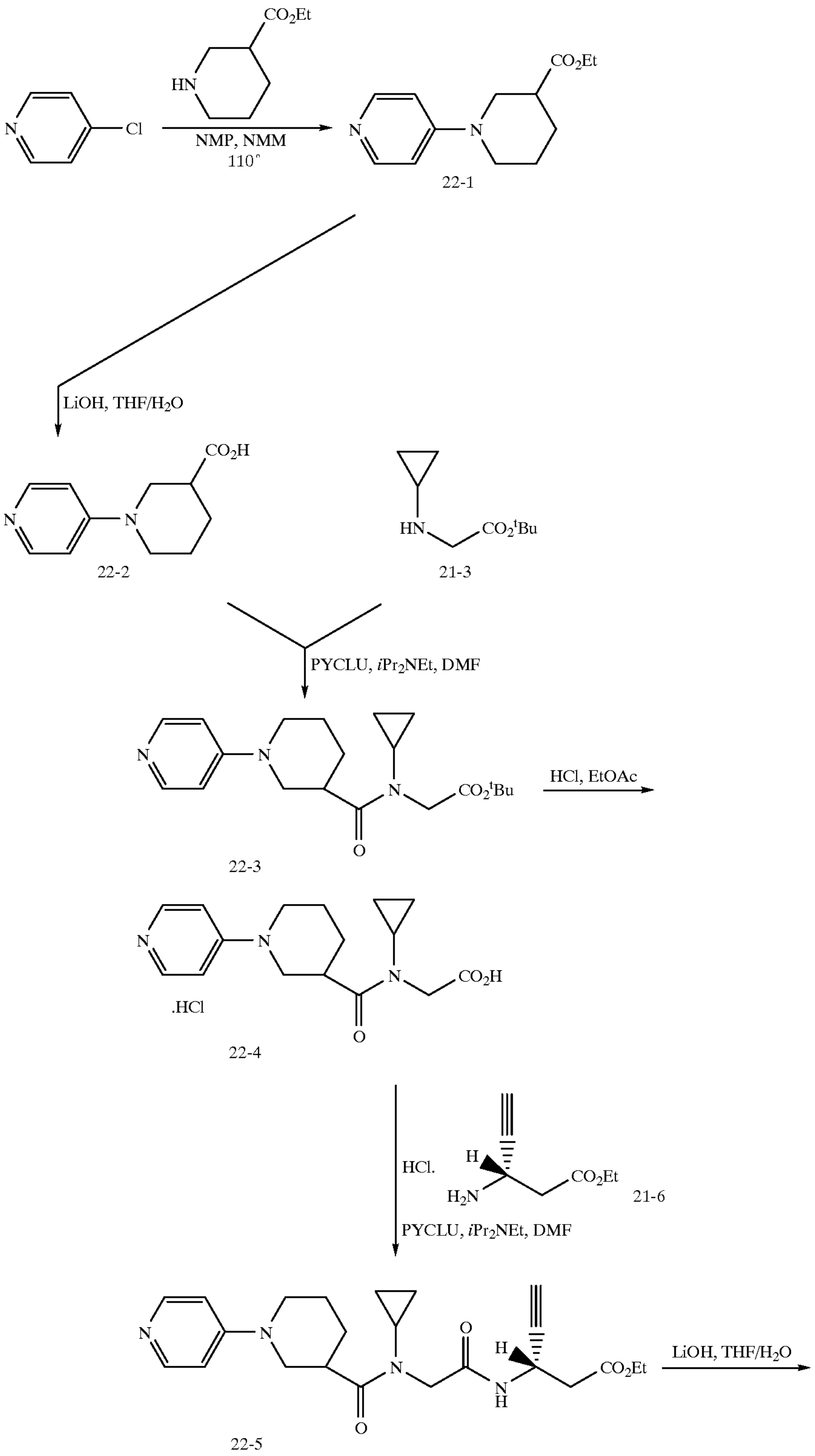

-continued

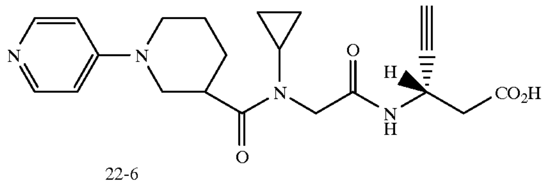

22-6

22-1

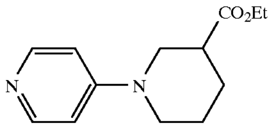

Ethyl N-pyridin-4-ylnipecotate (22-1)

Ethyl (±) nipecotate (7.0 g, 44.53 mmol) was reacted with 4-chlorpyridine hydrochloride (6.67 g, 44.53 mmol) as described for 21-1 to give the title compound as a yellow solid.

$^1$H NMR (300 MHz, $CDCl_3$) δ 8.22 (d, J=6.8 Hz, 2H), 6.68 (d, J=6.8 Hz, 2H), 4.18 (q, J=7.0 Hz, 2H), 3.85 (m, 1H), 3.72 (m, 1H), 3.21 (m, 1H), 3.10 (m, 1H), 2.60 (m, 1H), 2.08 (m, 1H), 1.81 (m, 2H), 1.60 (m, 1H), 1.13 (t, J=7.0 Hz, 3H).

22-2

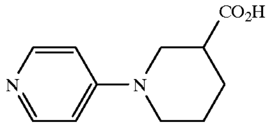

N-Pyridin-4-ylnipecotic acid (22-2)

Prepared from 22-1 (764 mg, 3.25 mnol) in a manner similar to that described for 21-2.

$^1$H NMR (300 MHz, DMSO-$d_6$) δ 8.13 (d, J=6.8 Hz, 2H), 6.74 (d, J=6.8 Hz, 2H), 4.08 (d, 1H), 3.78 (m, 1H), 2.92 (m, 2H), 2.10 (m, 1H), 1.95 (m, 1H), 1.71 (m, 1H), 1.42 (m, 2H).

22-3

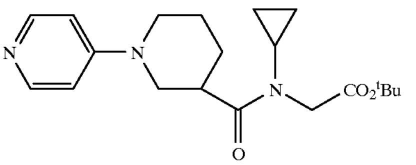

tert-Butyl N-pyridin-4-ylnipecotyl-N-cyclopropylglycine (22-3)

Prepared from 22-2 (320 mg, 1.51 mmol) and 21-3 (258 mg, 1.51 mmol) in a manner similar to that described for 21-4.

$^1$H NMR (300 MHz, $CDCl_3$) δ 8.12 (d, 6.8 Hz, 2H), 6.62 (d, J=6.8 Hz, 2H), 3.94 (s, 2H), 3.85 (m, 1H), 3.12 (m, 1H), 3.08 (m, 1H), 2.51 (m, 2H), 1.95 (m, 1H), 1.85 (m, 2H), 1.58 (m, 2H), 1.42 (s, 9H), 0.47 (m, 2H), 0.38 (m, 2H).

22-4

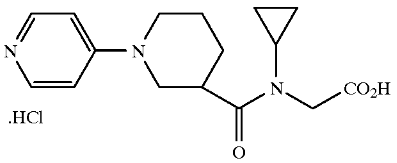

N-Pyridin-4-ylnipecotyl-N-cyclopropylglycine hydrochloride (22-4)

Ester 22-3 (250 mg, 0.70 mmol) was suspended in EtOAc (25 mL), cooled to 0° and treated with HCl gas for 15 min. The resulting solution was stirred for 3.5 h then evaporated to give 22-4 as a white solid.

$^1$H NMR (300 MHz, DMSO-$d_6$) δ 8.18 (d, J=6.8 Hz, 2H), 7.18 (d, J=6.8 Hz, 2H), 4.24 (d, J=12.8 Hz, 2H), 3.95 (m, 2H), 3.21 (m, 1H), 1.94 (m, 1H), 1.85 (m, 1H), 1.72 (m, 1H), 1.53 (m, 1H), 0.87 (m, 2H), 0.75 (m, 2H).

22-5

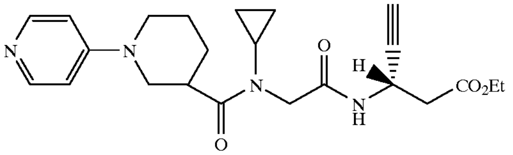

Ethyl N-pyridin-4-ylnipecotyl-N-cyclopropylglycyl-3(S)-ethynyl-β-alanine (22-5)

Prepared from 22-4 (195 mg, 0.60 mmol) in a manner similar to that described for 21-7.

$^1$H NMR (300 MHz, $CD_3OD$) δ 8.49 (d, J=6.8 Hz, 1H), 8.17 (d, J=6.8 Hz, 2H), 7.21 (d, J=6.8 Hz, 2H), 5.15 (m, 1H), 4.26 (m, 1H), 4.21 (d, 1H), 4.08 (q, 2H), 3.82 (m, 1H), 3.5–3.3 (m, 3H), 2.95 (m, 1H), 2.76 (m, 1H), 2.71 (m, 2H), 2.15 (m, 1H), 1.95 (m, 1H), 1.81 (m, 1H), 1.72 (m, 1H), 1.21 (t, 3H), 0.87 (m, 2H).

22-6

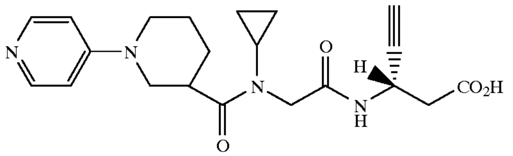

N-Pyridin-4-ylnipecotyl-N-cyclopropylglycyl-3(S)-ethynyl -β-alanine (22-6)

Prepared from 22-4 (20 mg, 0.04 mmol) in a manner similar to that described for 21-8.

FAB mass spectrum m/z=399 (M +1).
$^1$H NMR (300 MHz, $CD_3OD$) δ 8.16 (d, J=6 Hz, 2H), 6.91 (d, J=6.8 Hz, 2H), 5.05 (m, 1H), 4.26 (d, Hz, 1H), 4.21 (d, 1H), 3.82 (m, 1h), 3.5–3.3 (m, 3H), 2.95 (m, 1H), 2.76 (m, 1H), 2.71 (m, 2H), 2.15 (m, 1H), 1.95 (m, 1H), 1.81 (m, 1H), 1.72 (m, 1H), 1.21 (t, 1H), 0.87 (m, 2H).
SCHEME 23
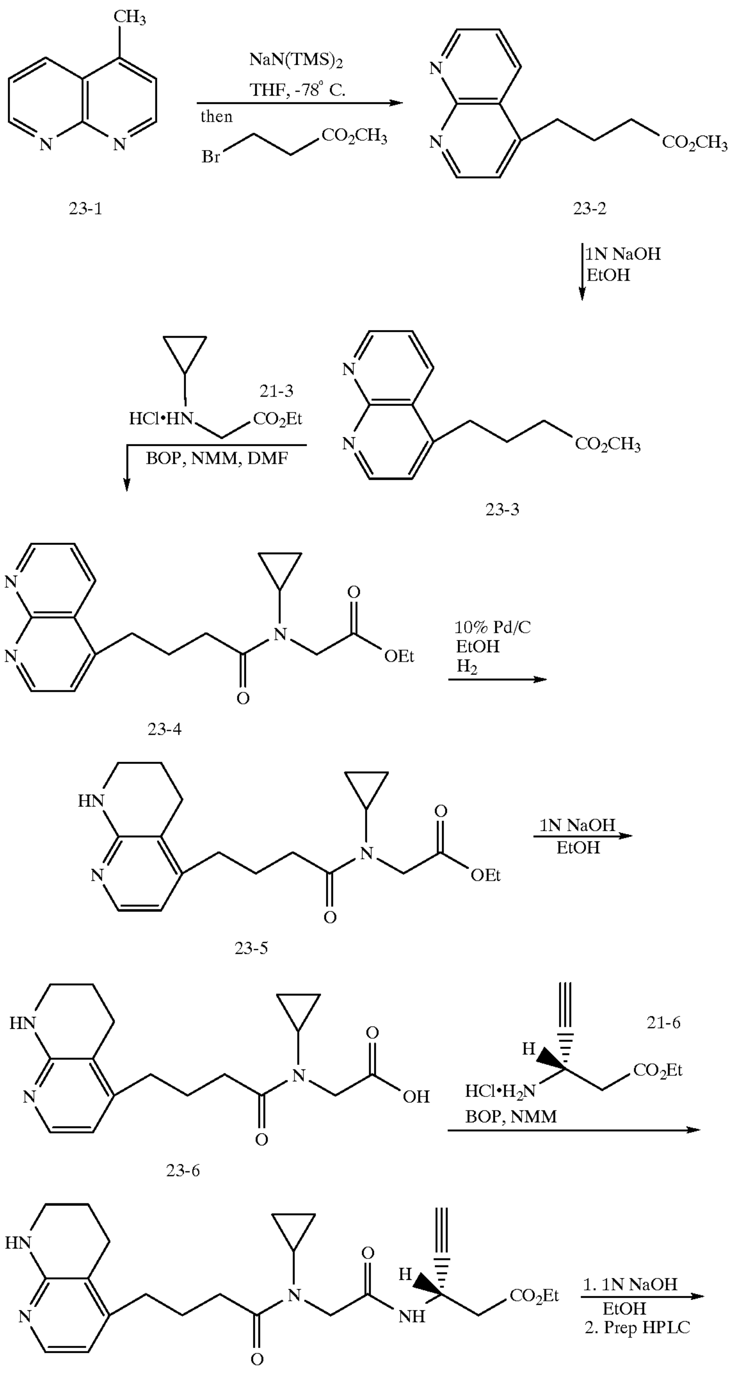

-continued

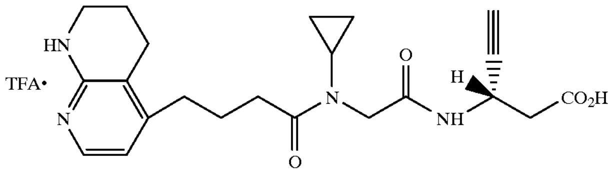

23-8

23-2

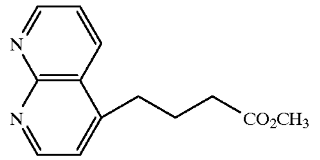

Methyl 4-(1,8-naphthyridin-4-yl)butyrate (23-2)

To a stirred solution of naphthyridine 23-1 (Hamada, Y. et al., *Chem. Pharm. Bull. Soc.,* 1971, 19(9), 1857–1862), (2.2 g, 15.2 mmol) and THF (200 ml) at −78° C. was added NaN(TMS)2 (1M/THF, 18 ml, 18 mmol) dropwise over a 20 min period. After 30 minutes at −78° C., methyl 3-bromopropionate was added in a stream. After 30 min, the reaction was quenched with 50 ml 10% $KHSO_4$. The mixture was extracted with $Et_2O$. The remaining aqueous portion was basified with sat. $NaHCO_3$ and then extracted with EtOAc. The EtOAc portion was washed with brine, dried ($MgSO_4$) and concentrated. Flash chromatography (silica, 2% EtOH/EtOAc) gave the ester 23-2 (1.61 g) as a yellow oil.

TLC $R_f$=0.27 (silica, 2% EtOH/EtOAc)

$^1$H NMR (400 MHz, $CDCl_3$) δ 9.14 (m, 1H), 9.35 (d, J=4 Hz, 1H), 8.50 (d, J=7 Hz, 1H), 7.52 (q, J=4 Hz, 1H), 7.33 (d, J=4 Hz, 1H), 3.71 (s, 3H), 3.14 (t, J=8 Hz, 2H), 2.46 (t, J=7 Hz, 2H), 2.09 (m, 2H).

23-3

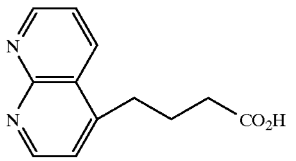

4-(1 8-Naphthyridin-4-yl)butanoic acid (1-3)

A solution of ester 23-2 (1.60 g, 6.9 mmol), 1N NaOH (7 ml, 7 mmol) and EtOH (20 ml) was stirred at ambient temperature for 1.0 h. The solution was extracted with $Et_2O$. The aqueous portion was neutralized with concentrated HCl (583 μl, 7.0 mmol). The precipitate was collected, washed with $Et_2O$, and dried in vacuo to furnish carboxylic acid 23-3 as a tan solid.

TLC $R_f$=0.59 (silica, 20:1:1 $CH_2Cl_2$/MeOH/AcOH)

$^1$H NMR (400 MHz, $CD_3OD$) δ 9.05 (q, J=2H, 1H), 8.95 (d, J=4H, 1H), 8.77 (dd, J=2 Hz, 8 Hz, 1H), 7.67 (q, J=4H, 1H), 7.53 (d, J=4 Hz, 1H), 3.22 (t, J=8 Hz, 2H), 2.46 (t, J=7 Hz, 2H), 2.03 (m, 2H).

23-4

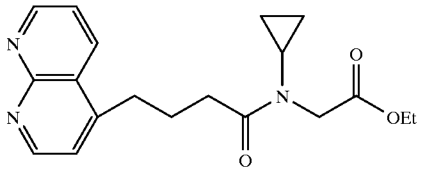

4-(1,8-Naphthyridin-4-yl)butanoyl-N-(cyclopropyl) glycine ethyl ester (23-4)

A solution of acid 23-3 (400 mg, 1.84 mmol), amine 21-3 (331 mg, 1.84 mmol), BOP reagent (979 mg, 2.21 mmol), NMM (1.03 ml, 7.36 mmol) and DMF (20 ml) was stirred at ambient temperature for 20 h. The solution was diluted with ethyl acetate and then washed with sat. $NaHCO_3$, brine, dried ($MgSO_4$) and concentrated. Flash chromatography (silica, 10:1 EtOAc/sat. $NH_3$-EtOH) furnished ester 23-4 (600 mg) as an orange solid.

TLC $R_f$=0.15 (silica, 10:1 EtOAc/sat. $NH_3$-EtOH)

$^1$H NMR (300 MHz, $CDCl_3$) δ 9.12 (m, 1H), 9.03 (d, J=4 Hz, 1H), 8.62 (dd, J=2 Hz, 8 Hz, 1H), 7.53 (q, J=4 Hz, 1H), 7.38 (d, J=4 Hz, 1H), 4.20 (q, J=7 Hz, 2H), 4.13 (s, 2H), 3.19 (t, J=8 Hz, 2H), 2.79 (m, 1H), 2.70 (m, 2H), 2.13 (m, 2H), 1.29 (t, J=8 Hz, 3H), 0.85 (m, 2H), 0.74 (m, 2H).

23-5

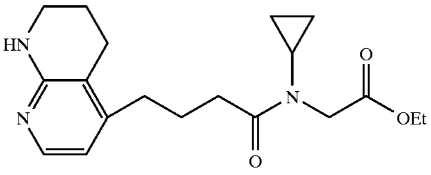

4-(1,2,3,4-Tetrahydro-1,8-naphthyridin-5-yl) butanoyl-N-(cyclo-propyl)glycine ethyl ester (23-5)

A mixture of ester 23-4 (600 mg, 1.75 mmol), 10% Pd/C (300 mg) and EtOH (30 ml) was stirred under hydrogen atmosphere (1 atm) at ambient temperature for 20 h. The catalyst was removed by filtration through celite and then the filtrate was concentrated. Flash chromatography (silica, 50%/EtOAc/sat. $NH_3$-EtOH) gave ester 23-5 as a colorless oil.

TLC $R_f$=0.25 (silica, 50:1 EtOAc/sat. $NH_3$-EtOH)

$^1$H NMR (400 MHz, $CD_3OD$) δ 7.58 (d, J=6 Hz, 1H), 6.48 (d, J=6 Hz, 1H), 4.15 (q, J=7 Hz, 2H), 4.08 (s, 2H), 3.36 (t, J=5 Hz, 2H), 2.86 (m, 1H), 2.75 (t, J=6 Hz, 2H), 2.68 (t, J=7 Hz, 2H), 2.60 (t, J=8 Hz, 2H), 1.90 (m, 4H), 1.25 (t, J=7 Hz, 3H), 0.87 (m, 2H), 0.78 (m, 2H).

23-6

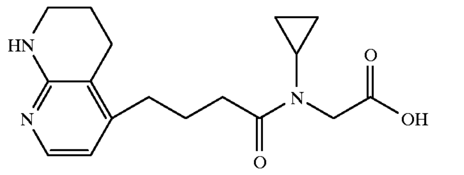

4-(1,2,3,4-Tetrahydro-1,8-napthyridin-5-yl)butanoyl-N-(cyclo-propyl)glycine (23-6)

A solution of ester 23-5 (200 mg, 0.5774 mmole), 1N NaOH (600 μl, 0.600 mmole) and $CH_3OH$ was stirred at ambient temperature for 1.5 h. The solution was concentrated. The residue was dissolved in 1N HCl (600 μl) and then the solution was concentrated. The residue was dissolved in $CHCl_3$, filtered and concentrated to give the carboxylic acid 23-6 (110 mg) as a white solid.

TLC $R_f$=0.14 (silica, 10:1:1 $CH_2Cl_2$/MeOH/AcOH)

$^1$H NMR (300 MHz, $CD_3OD$) δ 7.56 (d, J=6 Hz, 1H), 6.64 (d, J=6 Hz, 1H), 3.98 (s, 2H), 3.41 (t, J=6 Hz, 2H), 2.89 (m, 1H), 2.81 (t, J=6 Hz, 2H), 2.71 (m, 4H), 1.88 (m, 4H), 0.82 (m, 4H).

23-7

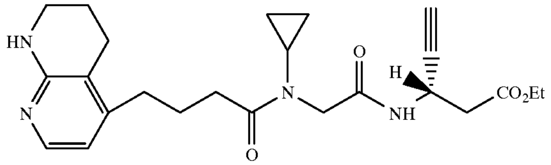

4-(1,2,3,4-Tetrahydro-1,8-naphthyridin-5-yl) butanoyl-N-(cyclo-propyl)glycyl-3(S)-ethynyl-β-alanine ethyl ester (23-7)

To a stirred solution of acid 23-6 (40 mg, 0.1256 mmol), amine 21-6 (33 mg, 0.1884 mmol), NMM (70 μl, 0.5024 mmol) and $CH_3CN$ (1 ml) was added BOP reagent (61 mg, 0.1382 mmol). After 20 h at ambient temperature, the solution was diluted with ethyl acetate and then washed with sat. $NaHCO_3$, brine, dried ($MgSO_4$) and concentrated. Flash chromatography (silica, 40:1:1 $CH_2Cl_2$/MeOH/AcOH) gave the ester 23-7 as a colorless oil.

TLC $R_f$=0.23 (silica, 40:1:1 $CH_2Cl_2$/MeOH/AcOH)

$^1$H NMR (300 MHz, $CD_3OD$) δ 7.58 (d, J=6 Hz, 1H), 6.66 (d, J=6 Hz, 1H), 5.01 (m, 1H), 4.13 (q, J=7 Hz, 2H), 4.02 (s, 2H), 3.42 (t, J=6 Hz, 2H), 2.72 (m, 10H), 1.95 (m, 4H), 1.24 (t, J=7 Hz, 3H), 0.85 (m, 2H), 0.78 (m, 2H).

23-8

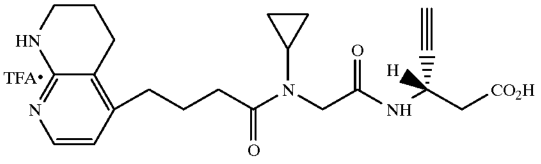

4-(1,2,3,4-Tetrahydro-1,8-naphthyridin-5-yl) butanoyl-N-(cyclo-propyl)glycyl-3(S)-ethynyl-β-alanine (23-8)

A solution of ester 23-7 (32 mg, 0.0725 mmol), 1N NaOH (100 μl) and $CH_3OH$ (500 ml) was stirred at ambient temperature for 1.0 h. The solution was concentrated. The residue was dissolved in 1N HCl (100 μl) and then concentrated. Preparative HPLC purification ($C_{18}$, $H_2O/CH_3CN$/TFA) provided acid 23-8 as a TFA salt.

TLC $R_f$=0.50 (silica, 10:1:1 EtOH/$NH_4OH/H_2O$)

$^1$H NMR (300 MHz, $CD_3OD$) δ 8.43 (d, J=9 Hz, 1H), 7.58 (d, J=7 Hz, 1H), 6.76 (d, J=7 Hz, 1H), 4.99 (m, 1H), 4.03 (d, J=3 Hz, 2H), 3.46 (t, J=5 Hz, 2H), 2.72 (m, 10H), 1.95 (m, 4H), 0.87 (m, 2H), 0.79 (m, 2H).

SCHEME 24

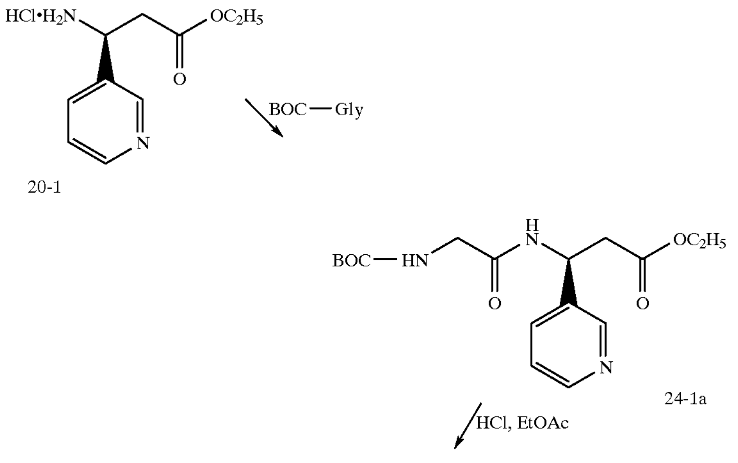

20-1

24-1a

-continued
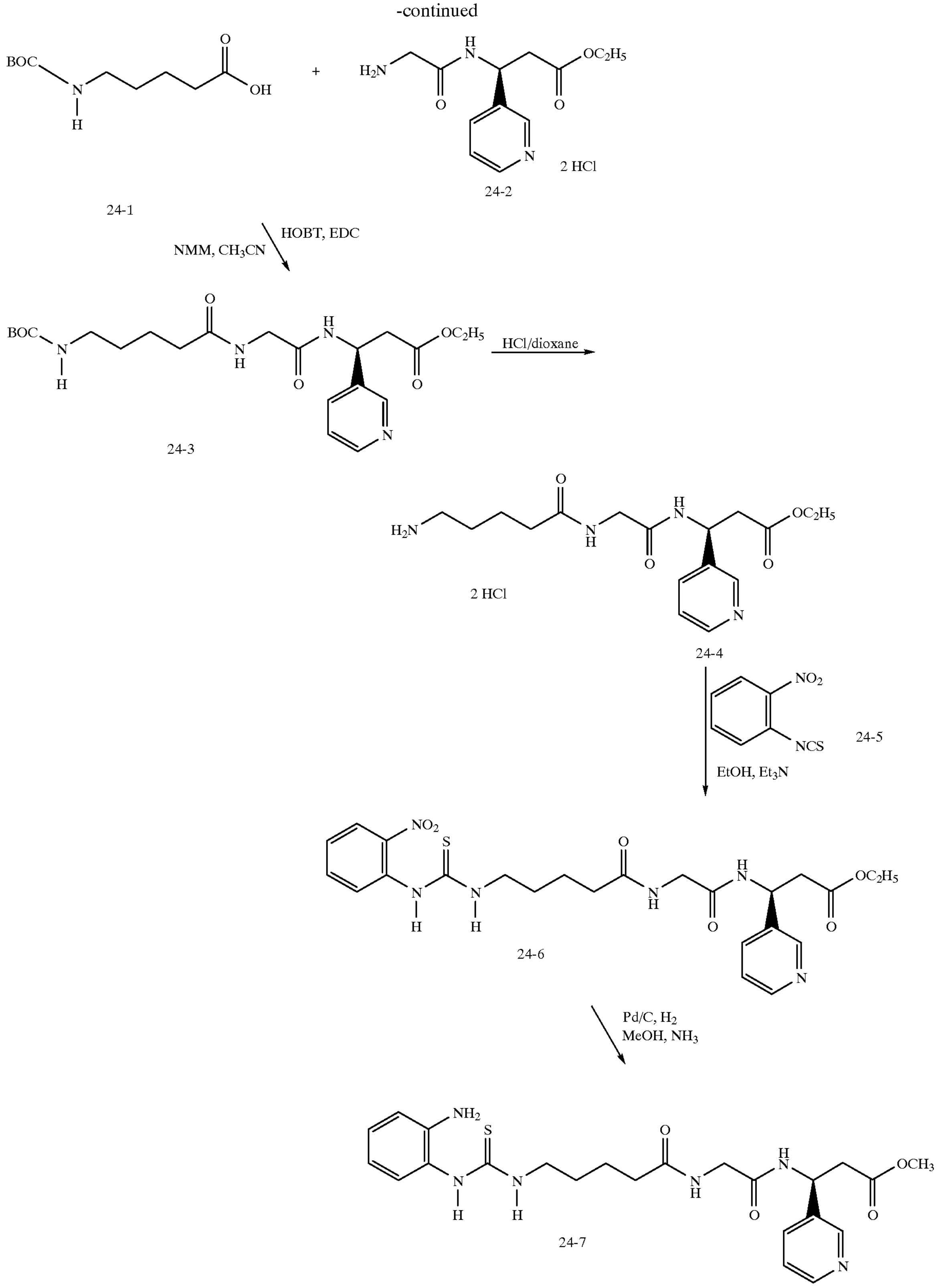
24-1
24-2
24-3
24-4
24-5
24-6
24-7

-continued

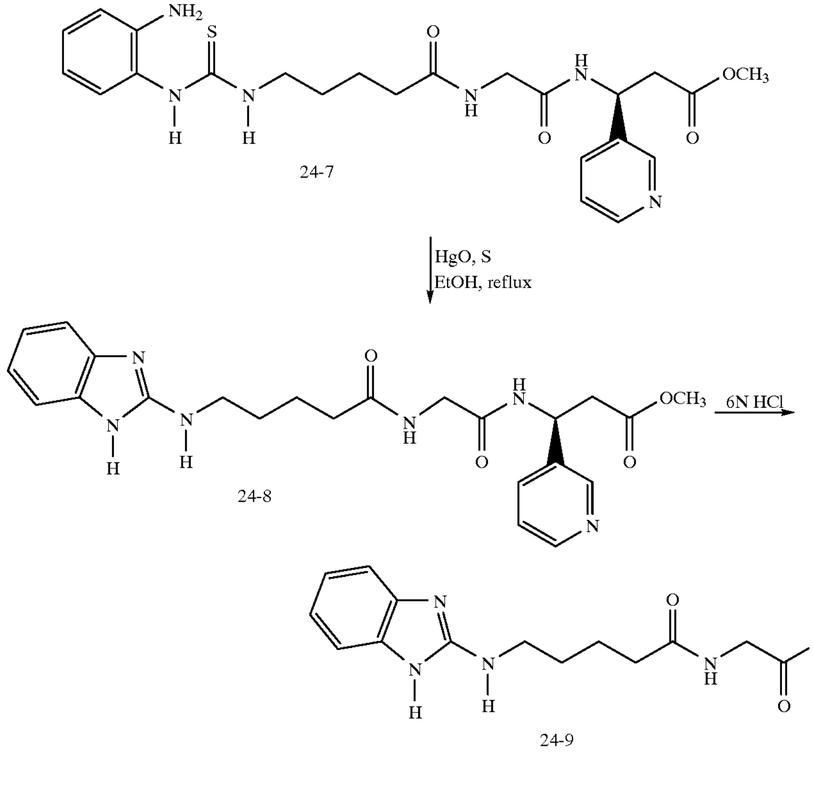

24-7

24-8

24-9

Preparation of 3-{2-[5-(1H-Benzoimidazol-2-yl-amino)-pentanoyl-amino]-acetylamino}-3(S)-pyridin-3-yl-propionic acid (24-9)

3-t-Butoxycarbonylaminoacetylamino-3(S)-pyridin-3-yl-propionic acid ethyl ester bis hydrochloride (24-1a)

A stirred solution of BOC-Gly (645 mg, 3.7 mmol), NMM (452 uL, 4.0 mmol), and EtOAc (35 mL) at 0° C. was treated with isobutyl chloroformate (534 uL, 4.0 mmol). After 20 min 20-1 (1.0 g, 3.7 mmol) and NMM (1.2 mL, 11 mmol) were added followed by removal of the cooling bath. After 20 hr, the reaction mixture was washed with $H_2O$, sat. $NaHCO_3$, and brine, dried ($MgSO_4$), and concentrated. Flash chromatography (silica, EtOAc to 5% MeOH/EtOAc) gave 24-1 as a colorless oil.

TLC: Rf=0.31 (20% MeOH/EtOAc), $^1$H NMR (300 MHz, $CDCl_3$) δ 8.58 (bs, 1H), 8.51(m, 1H), 7.62 (m, 1H), 7.49 (m, 1H), 5.48 (m, 1H), 4.13 (m, 1H), 4.08 (q, J=7 Hz, 2H), 3.83 (m, 2H), 2.90 (m, 2H), 1.43 (s, 9H), 1.13 (t, J=7 Hz, 3H).

3-Aminoacetylamino-3(S)-pyridin-3-yl-propionic acid ethyl ester bis-hydrochloride (24-2)

HCl gas was passed through a solution of 24-1a (0.84 g, 2.4 mmol) in EtOAc (24 mL) at 0° C. for 15 min and the reaction mixture stirred for an additional 15 min. The reaction mixture was concentrated and the residue triturated with ether to give 24-2 as a white solid.

TLC: Rf=0.29 (10:1:1 ethanol/$H_2O$/$NH_4OH$).

3-[2-(5-t-Butoxycarbonylaminopentanoylamino) acetylamino]-3(S)-pyridin-3-yl-propionic acid ethyl ester (24-3)

A $CH_3CN$ solution (20 mL) of 24-1 (71.7 mg, 0.33mmol), 24-2 (97 mg, 0.30 mmol), HOBT (50.5 mg, 0.33 mmol), EDC (63.3 mg, 0.33 mmol) and NMM (132 ml, 1.2 mmol) was stirred under ambient conditions for 18 hr. The reaction solution was concentrated to a yellow gum which was partitioned between EtOAc and sat. $NaCO_3$ solution. The EtOAc layer was washed with $H_2O$, brine, dried($MgSO_4$) and concentrated to provide 24-3 as a colorless gum.

TLC: Rf=0.41 (50% $CH_2Cl_2$/acetone), $^1$H NMR (300 MHz, $CDCL_3$) δ 8.56(bs, 1H), 8.51(m, 1H), 7.62(m, 1H), 7.49(m, 1H), 5.43(m, 1H), 4.08(q, J=7 Hz, 2H), 3.94(m, 2H), 3.12(m, 2H), 2.90(m, 2H), 2.28(m, 2H), 1.64(m, 4H), 1.43(s, 9H), 1.13(t, J=7 Hz, 3H).

3-[2-(5-Aminopentanoylarnino)-acetylamino]-3(S)-pyridin-3-yl-propionic acid ethyl ester dihydrochloride (24-4)

A 4M HCl/dioxane solution(10 mL) of 24-3 (101 mg, 0.24 mmol) was stirred under ambient conditions for 18 hr. The solution was concentrated to provide 24-4 as a pale yellow gum which was used in the next step without further purification.

$^1$H NMR (300 MHz, $CD_3OD$) δ 8.93(bs, 1H), 8.79(m, 1H), 8.69(m, 1H), 8.10(m, 1H), 5.48(m, 1H), 4.14(q, J=7 Hz, 2H), 3.88(m, 2H), 3.07(m, 2H), 2.89(m, 2H), 2.33(m, 2H), 1.68(m, 4H), 1.23(t, J=7 Hz, 3H).

3-(2-{5-[3-(2-Nitrophenyl)-thioureido]-pentanoylamino}-acetyl-amino)-3(S)-pyridin-3-yl-propionic acid ethyl ester (24-6)

An ethanol solution(20 mL) of 24-5 (40 mg, 0.224 mmol) and 24-4 (95 mg, 0.224 mmol) was refluxed for 2 hr and concentrated to a yellow gum which was purified by flash chromatography (80% EtOAc/EtOH—$NH_3$) to provide 24-6 as a yellow gum.

TLC: Rf=0.41 (80% EtOAc/EtOH—$NH_3$),

1H NMR (300 MHz, $CD_3OD$) δ 8.54(m, 1H), 8.42(m, 1H), 8.03(m, 2H), 7.83(m, 1H), 7.63(m, 1H), 7.41(m, 1H), 7.32 (m, 1H), 5.39(m, 1H), 4.09(q, J=7 Hz, 2H), 3.86(s, 2H), 3.61(m, 2H), 2.91(m, 2H), 2.33(m, 2H), 1.69(m, 4H), 1.16(t, J=7 Hz, 3H).

3-(2-{5-[3-(2-Aminophenyl)-thioureido]-pentanoylamino}-acetylamino)-3(S)-pyridin-3-yl-propionic acid methyl ester (24-7)

10% Pd/C (50 mg) and 24-6 (103 mg, 0.194 mmol) were added to methanol saturated with ammonia and the mixture hydrogenated at 1 atm. for 18 hr. The reaction was filtered and concentrated to provide 24-7 as a pale yellow gum which was used in the next step without further purification.

$^1$H NMR (300 MHz, $CD_3OD$) δ 8.53(m, 1H), 8.41(m, 1H), 7.84(m, 1H), 7.40(m, 1H), 7.07(m, 1H), 6.97(m, 1H), 6.82 (m, 1H), 6.67(m, 1H), 5.38(m, 1H), 3.85(m, 2H), 3.62(s, 3H). 3.54(m, 2H), 2.93(m, 2H), 2.30(m, 2H), 1.60(m, 4H).

3-{2-[5-(1H-Benzoimidazol -2-yl-amino)-pentanoylamino]-acetyl -amino}-3(S)-pyridin-3-yl-propionic acid methyl ester (24-8)

An ethanol mixture(20 ml) of 24-7 (89 mg, 0.18 mmol), mercuric oxide (78.8 mg, 0.36 mmol) and sulfur (1.8 mg, 0.056 mmol) was refluxed for 2 hr. After cooling, the mixture was filtered and the filtrate concentrated to a semi-solid which was purified by flash chromatography (20% $MeOH/CH_2Cl_2$) to provide 24-8 as a solid.

TLC: Rf=0.13 (20% $MeOH/CH_2Cl_2$), $^1$H NMR (300 MHz, $CD_3OD$) δ 8.52(m, 1H), 8.41 (m, 1H), 7.81 (m, 1H), 7.38(M, 1H), 7.23(m, 2H), 7.06(m, 2H), 5.38(m, IH), 3.85(s, 2H), 3.62(s, 3H), 3.37(m, 2H), 2.95(m, 2H), 2.33(m, 2H), 1.71(m, 4H).

3-{2-[5-(1H-Benzoimidazol-2-yl-amino)-pentanoylamino]-acetyl-amino]}-3(S)-pyridin-3-yl-propionic acid (24-9)

A 6N HCl solution (5 ml) of 24-8 (33 mg, 0.073 mmol) was stirred under ambient conditions for 18 hr. The reaction was concentrated to give a viscous gum which was purified by prep HPLC (Delta-Pak $C_{18}$, gradient elution over 40 min., 5–50% $CH_3CN/H_2O$-0.1% TFA) to give 24-9.

$^1$H NMR (300 MHz, $CD_3OD$) δ 8.78(m, 1H), 8.65(m, 1H), 8.40(m, 1H), 7.86(m, 1H), 7.34(m, 2H), 7.27(m, 2H), 5.40 (m, 1H), 3.87(m, 2H), 3.42(m, 2H), 2.98(m, 2H), 2.34(M, 2H), 1.74(m, 4H).

EXAMPLE 25

Tablet Preparation

Tablets containing 25.0, 50.0, and 100.0 mg., respectively, of the following active compounds are prepared as illustrated below:

4-(2-Amino-pyridin-6-yl)butanoyl-N-cyclopropylglycyl-3(R)-(2-phenethyl)-β-alanine;

4-(2-Bocamino-pyridin-6-yl)butanoyl-N-cyclopropylglycyl-3(R)-[(2-indol-3-yl)ethyl]-β-alanine; and 4-(2-Amino-pyridin-6-yl)butanoyl-N-cyclopropylglycyl-3(R)-[(2-indol-3-yl)ethyl]-β-alanine.

TABLE FOR DOSES CONTAINING FROM 25–100 MG OF THE ACTIVE COMPOUND

| | Amount-mg | | |
|---|---|---|---|
| Active Compound | 25.0 | 50.0 | 100.0 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 26

Intravenous formulations

An intravenous dosage form of the above-indicated active compound is prepared as follows:

| | | |
|---|---|---|
| Active Compound | 0.5–10.0 | mg |
| Sodium Citrate | 5–50 | mg |
| Citric Acid | 1–15 | mg |
| Sodium Chloride | 1–8 | mg |
| Water for Injection (USP) | q.s. to 1 | L |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md0, copyright 1994.

EXAMPLE 27

Intravenous formulation

A pharmaceutical composition was prepared at room temperature using 4-(2-Aminothiazol-4-yl)butanoyl-glycyl-2(S)-phenylsulfonamido-β-alanine t-butyl ester, a citrate buffer, and sodium chloride, to obtain a concentration of 4-(2-Aminothiazol-4-yl)butanoyl-glycyl-2(S)-phenylsulfonamido-β-alanine t-butyl ester of 0.25 mg/ml.

800 grams of water was introduced into a standard pharmaceutical mixing vessel. 0.25 grams of the ester was dissolved in the water. 2.7 grams sodium citrate and 0.16 grams citric acid were added to obtain a finished citrate concentration of 10 mM. 8 grams of sodium chloride was added. 200 grams of water was then added to achieve the desired final concentrations of ingredients. The resulting aqueous formulation had the following concentrations:

| Ingredient | Amount | |
|---|---|---|
| 4-(2-Aminothiazol-4-yl)butanoyl-glycyl-2(S)-phenylsulfonamido-β-alanine t-butyl ester | 0.25 | mg/ml |
| citrate buffer | 10 | mM |
| sodium chloride | 8 | mg/ml |

The finished concentrated formulation is stored in a standard USP Type I borosilicate glass container at 30–40 degrees C. Prior to compound administration, the concentrated formulation is diluted in a 4:1 ratio resulting in a finished concentration of 0.05 mg/ml and transfered to an infusion bag.

Therapeutic Treatment

Compounds of the invention may be administered to patients where inhibition of human or mammalian platelet aggregation or adhesion is desired.

Compounds of the invention are useful in inhibiting platelet aggregation and thus, they may find utility in surgery on peripheral arteries (arterial grafts, carotid endaterectomy) and in cardiovascular surgery where manipulation of arteries and organs, and/or the interation of platelets with artificial surfaces, leads to platelet aggregation and consumption. The aggregated platelets may form thrombi and thromboemboli. Compounds of the invention may be administered to these surgical patients to prevent the formation of thrombi and thromboemboli.

Compounds of the invention are also effective inhibitors of osteoclast cellular adhesion, and can be administered to inhibit bone resorption. The dosage regimen utilizing the compounds of the present invention for this purpose is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the compounds, when used to prevent osteoclast cellular adhesion, will range between about 0.01 mg per kg of body weight per day (mg/kg/day) to about 100 mg/kg/day and preferably 0.01–50 mg/kg/day and more preferably 0.01–20 mg/kg/day, e.g. 0.1 mg/kg/day, 1.0 mg/kg/day, 5.0 mg/kg/day, or 10 mg/kg/day. Advantageously, compounds of the present invention may be administered in divided doses of two, three, or four times daily. Intravenously, the most preferred doses will range from about 1 to about 10 mg/kg/minute during a constant rate infusion. Furthermore, preferred compounds for the present invention can be administered in intranasal form via topical use of suitable intranasal vehicles, or via transdernal routes, using those forms of transdermal skin patches well known to those of ordinary skill in that art. To be administered in the form of a transdernal delivery system, the dosage administration will, or course, be continuous rather that intermittent throughout the dosage regime.

EIB ASSAY

Duong et al., *J. Bone Miner. Res.,* 8:S 378, describe a system for expressing the human integrin $\alpha v\beta_3$. It has been suggested that the integrin is involved in the attachment of osteoclasts to bone matrix, since antibodies against the integrin, or RGD-containing molecules, such as echistatin (European Publication 382 451), can effectively block bone resorption.

Reaction Mixture:

1. 175 $\mu$l TBS buffer (50 mM Tris·HCl pH 7.2, 150 mM NaCl, 1% BSA, 1 mM $CaCl_2$, mM $MgCl_2$).
2. 25 $\mu$l cell extract (dilute with 100 mM octylglucoside buffer to give 2000 cpm/25 $\mu$l).
3. $^{125}$I-echistatin (25 $\mu$l/50,000 cpm) (see EP 382 451).
4. 25 $\mu$l buffer (total binding) or unlabeled echistatin (non-specific binding).

The reaction mixture was then incubated for 1 h at room temp. The unbound and the bound $\alpha v\beta_3$ were separated by filtration using a Skatron Cell Harvester. The filters (prewet in 1.5% polyethyleneimine for 10 mins) were then washed with the wash buffer (50 mM Tris HCl, 1 mM $CaCl_2/MgCl_2$, pH 7.2). The filter was then counted in a gamma counter.

The following compounds were tested and shown to bind to the human integrin $\alpha v\beta_3$.

| Compound | EIB |
|---|---|
| 2-3 | <2000 nM |
| 3-8 | <1000 nM |
| 5-9 | <1000 nM |
| 19-10 | <1000 nM |
| 20-3 | <1000 nM |
| 24-9 | <1000 nM |

What is claimed is:

1. A compound having the formula:

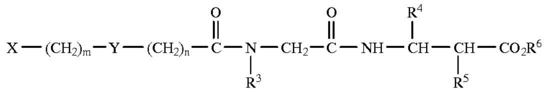

and pharmaceutically acceptable salts thereof, wherein X is

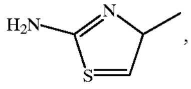,

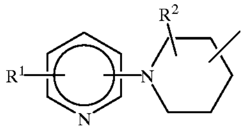, 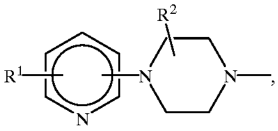,

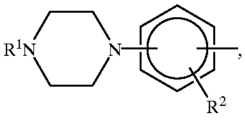, 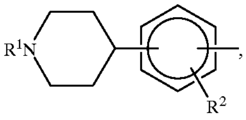,

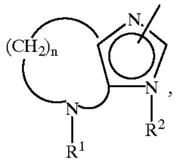, 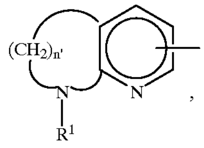,

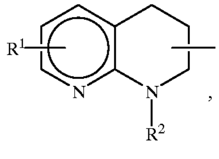, 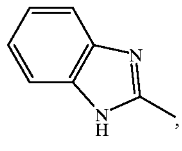,

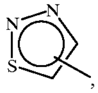, 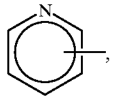, or 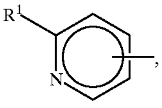, wherein n is 2–4, and n' is 2 or 3, and wherein $R^1$ and $R^2$ are independently selected from the group consisting of hydrogen, F, Cl, Br, I, $C_{1-10}$ alkyl, $C_{3-8}$ cycloalkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino $C_{1-8}$ alkyl, $C_{1-6}$ dialkylamino, $C_{1-6}$ dialkylamino $C_{1-8}$ alkyl, $C_{1-4}$ alkoxy, $C_{1-4}$ alkoxy $C_{1-6}$ alkyl, carboxy, carboxy $C_{1-6}$ alkyl, $C_{1-3}$ alkoxycarbonyl, $C_{1-3}$ alkoxycarbonyl $C_{1-6}$ alkyl, carboxy $C_{1-6}$ alkyloxy and hydroxy, hydroxy $C_{1-6}$ alkyl;

Y is

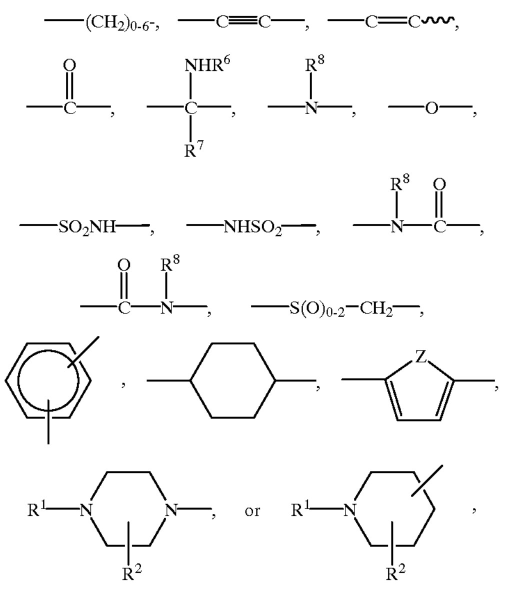

where Z is O, $NR^8$, or S;

$R^8$ is hydrogen, F, Cl, Br, I, $C_{1-10}$ alkyl, $C_{3-8}$ cycloalkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino $C_{1-8}$ alkyl, $C_{1-6}$ dialkylamino, $C_{1-6}$ dialkylamino $C_{1-8}$ alkyl, $C_{1-4}$ alkoxy, $C_{1-4}$ alkoxy $C_{1-6}$ alkyl, carboxy, carboxy $C_{1-6}$ alkyl, $C_{1-3}$ alkoxycarbonyl, $C_{1-3}$ alkoxycarbonyl $C_{1-6}$ alkyl, carboxy $C_{1-6}$ alkyloxy, hydroxy, or hydroxy $C_{1-6}$ alkyl;

$R^3$ and $R^4$ are independently hydrogen, a five or six membered mono or polycyclic aromatic ring system containing 0, 1, 2, 3, or 4 heteroatoms selected from nitrogen, oxygen and sulfur, either unsubstituted or substituted, with one or more groups selected from hydroxyl, halogen, cyano, trifluoromethyl, $C_{1-3}$ alkoxy, $C_{1-5}$ alkylcarbonyloxy, $C_{1-5}$ alkoxycarbonyl $C_{1-5}$ alkyl, amino$C_{1-5}$ alkyl, hydroxycarbonyl, hydroxycarbonyl$C_{1-5}$ alkyl, or hydroxycarbonyl$C_{1-5}$ alkoxy, $-(CH_2)_n$-aryl, wherein n=1–4 and aryl is defined as a five or six membered mono or polycyclic aromatic ring system containing 0, 1, 2, 3, or 4 heteroatoms selected from nitrogen, oxygen and sulfur, either unsubstituted or substituted, with one or more groups selected from hydroxyl, halogen, cyano, trifluoromethyl, $C_{1-3}$ alkoxy, $C_{1-5}$ alkylcarbonyloxy, $C_{1-5}$ alkoxycarbonyl, $C_{1-5}$ alkyl, amino$C_{1-5}$ alkyl, hydroxycarbonyl, hydroxycarbonyl$C_{1-5}$ alkyl, or hydroxycarbonyl$C_{1-5}$ alkoxy, halogen, hydroxyl, $C_{1-5}$alkylcarbonylamino, aryl$C_{1-5}$ alkoxy, $C_{1-5}$ alkoxycarbonyl, aminocarbonyl, $C_{1-5}$ alkylaminocarbonyl, $C_{1-5}$ alkylcarbonyloxy, C3-8 cycloalkyl, oxo, amino, $C_{1-3}$ alkylamino, amino$C_{1-3}$ alkyl, arylaminocarbonyl, aryl$C_{1-5}$alkylaminocarbonyl, aminocarbonyl, aminocarbonyl-$C_{1-4}$ alkyl, hydroxycarbonyl, hydroxycarbonyl $C_{1-5}$ alkyl, $C_{1-6}$alkyl, either unsubstituted or substituted, with one or more groups selected from halogen, hydroxyl, $C_{1-5}$ alkylcarbonylamino, aryl$C_{1-5}$ alkoxy, $C_{1-5}$ alkoxycarbonyl, aminocarbonyl, $C_{1-5}$ alkylaminocarbonyl, $C_{1-5}$ alkylcarbonyloxy, $C_{3-8}$ cycloalkyl, oxo, amino, $C_{1-3}$ alkylamino, amino$C_{1-3}$ alkyl, arylaminocarbonyl, aryl$C_{1-5}$alkylaminocarbonyl, aminocarbonyl, aminocarbonyl-$C_{1-4}$alkyl, hydroxycarbonyl, or hydroxycarbonyl $C_{1-5}$ alkyl, provided that the carbon atom to which $R^3$ and $R^4$ are attached bears only one heteroatom, $-(CH_2)_m$ $C\equiv CH$, $-(CH_2)_m$ $C\equiv C-C_{1-6}$ alkyl, —$(CH_2)_m$ C≡C—$C_{3-7}$cycloalkyl
—$(CH_2)_m$ C≡C-aryl,
—$(CH_2)_m$ C≡C—$C_{1-6}$ alkyl aryl
—$(CH_2)_m$ CH═$CH_2$,
—$(CH_2)_m$ CH═CH $C_{1-6}$ alkyl,
—$(CH_2)_m$ CH═CH—$C_{3-7}$cycloalkyl,
—$(CH_2)_m$ CH═CH aryl,
—$(CH_2)_m$ CH═CH $C_{1-6}$ alkyl aryl,
—$(CH_2)_m$ $SO_2C_{1-6}$ alkyl, or
—$(CH_2)_m$ $SO_2C_{1-6}$ alkylaryl;

$R^5$ is
hydrogen,
fluorine,
$C_{1-8}$ alkyl,
hydroxy $C_{1-6}$ alkyl,
carboxy,
carboxy $C_{1-6}$ alkyl,
$C_{1-6}$ alkyloxy.
$C_{3-8}$ cycloalkyl,
aryl $C_{1-6}$ alkyloxy,
aryl,
aryl $C_{1-6}$ alkyl,
$C_{1-6}$ alkylcarbonyloxy,
amino,
$C_{1-6}$ alkylamino,
amino $C_{1-6}$ alkyl,
$C_{1-6}$ alkylamino $C_{1-6}$ alkyl,
aryl amino,
aryl amino $C_{1-6}$ alkyl,
aryl $C_{1-6}$ alkylamino,
aryl $C_{1-6}$ alkylamino $C_{1-6}$ alkyl,
aryl carbonyloxy,
aryl $C_{1-6}$ alkylcarbonyloxy,
$C_{1-6}$ dialkylamino,
$C_{1-6}$ dialkylamino $C_{1-6}$ alkyl,
$C_{1-6}$ alkylaminocarbonyloxy,
$C_{1-8}$ alkylsulfonylamino,
$C_{1-8}$ alkylsulfonylamino $C_{1-6}$ alkyl,
aryl sulfonylamino $C_{1-6}$ alkyl,
aryl sulfonylamino,
aryl $C_{1-6}$ alkylsulfonylamino,
aryl $C_{1-6}$ alkylsulfonylamino $C_{1-6}$ alkyl,
$C_{1-8}$ alkyloxycarbonylamino,
$C_{1-8}$ alkyloxycarbonylamino $C_{1-8}$ alkyl,
aryl $C_{1-8}$ alkyloxycarbonylamino,
aryl oxycarbonylamino,
aryl oxycarbonylamino $C_{1-8}$ alkyl,
aryl $C_{1-8}$ alkyloxycarbonylamino $C_{1-8}$ alkyl,
$C_{1-8}$ alkylcarbonylamino,
$C_{1-8}$ alkylcarbonylamino $C_{1-6}$ alkyl,
aryl carbonylamino $C_{1-6}$ alkyl,
aryl carbonylamino,
aryl $C_{1-6}$ alkylcarbonylamino,
aryl $C_{1-6}$ alkylcarbonylamino $C_{1-6}$ alkyl,
$C_{1-8}$ alkylaminocarbonylamino,
aminocarbonylamino,
aminocarbonylamino $C_{1-6}$ alkyl,
$C_{1-8}$ alkylaminocarbonylamino $C_{1-6}$ alkyl,
aryl aminocarbonylamino $C_{1-6}$ alkyl,
aryl aminocarbonylamino,
aryl $C_{1-8}$ alkylaminocarbonylamino,
aryl $C_{1-8}$ alkylaminocarbonylamino $C_{1-6}$ alkyl,
aminosulfonylamino $C_{1-6}$ alkyl,
aminosulfonylamino,
$C_{1-8}$ alkylaminosulfonylamino,
$C_{1-8}$ alkylaminosulfonylamino $C_{1-6}$ alkyl,
aryl aminosulfonylamino $C_{1-6}$ alkyl,
aryl aminosulfonylamino,
aryl $C_{1-8}$ alkylaminosulfonylamino,
aryl $C_{1-8}$ alkylaminosulfonylamino $C_{1-6}$ alkyl,
$C_{1-6}$ alkylsulfonyl,
$C_{1-6}$ alkylsulfonyl $C_{1-6}$alkyl,
aryl sulfonyl,
aryl sulfonyl $C_{1-6}$alkyl,
aryl alkylsulfonyl,
aryl $C_{1-6}$ alkylsulfonyl,
aryl $C_{1-6}$ alkylsulfonyl $C_{1-6}$alkyl,
$C_{1-6}$ alkylcarbonyl,
$C_{1-6}$ alkylcarbonyl $C_{1-6}$ alkyl,
aryl carbonyl $C_{1-6}$ alkyl,
aryl carbonyl,
aryl $C_{1-6}$ alkylcarbonyl,
aryl $C_{1-6}$ alkylcarbonyl $C_{1-6}$alkyl,
$C_{1-6}$ alkylthiocarbonylamino,
$C_{1-6}$ alkylthiocarbonylamino $C_{1-6}$ alkyl,
aryl thiocarbonylamino $C_{1-6}$ alkyl,
aryl thiocarbonylamino,
aryl $C_{1-6}$ alkylthiocarbonylamino,
aryl $C_{1-6}$ alkylthiocarbonylamino $C_{1-6}$ alkyl,
aminocarbonyl $C_{1-6}$ alkyl,
aminocarbonyl,
$C_{1-8}$ alkylaminocarbonyl,
$C_{1-8}$ alkylaminocarbonyl $C_{1-6}$ alkyl,
aryl aminocarbonyl $C_{1-6}$ alkyl,
aryl aminocarbonyl,
aryl $C_{1-8}$ alkylaminocarbonyl,
aryl $C_{1-8}$ alkylaminocarbonyl $C_{1-6}$ alkyl, wherein alkyl groups and aryl groups may be unsubstituted or substituted with one or more substituents selected from $R^1$ and $R^2$; and $R^6$ and $R^7$ are independently
hydrogen,
$C_{1-8}$ alkyl,
aryl $C_{1-8}$ alkyl,
hydroxy,
$C_{1-8}$ alkyloxy,
aryl,
aryl $C_{1-6}$ alkyloxy,
$C_{1-8}$ alkylcarbonyloxy $C_{1-4}$ alkyloxy,
aryl $C_{1-8}$ alkylcarbonyloxy $C_{1-4}$ alkyloxy,
$C_{1-8}$ alkylaminocarbonylmethyleneoxy, or
$C_{1-8}$ dialkylaminocarbonylmethyleneoxy, where m and n are integers 0–6.

2. A compound of claim 1 selected from the group consisting of 4-(2-Aminothiazol-4-yl)butanoyl-glycyl-2(S)-phenylsulfonamido-β-alanine t-butyl ester,
4-(2-Aminothiazol-4-yl)butanoyl-glycyl-2(S)-phenylsulfonamido-β-alanine,
4-(2-Aminothiazol4-yl)butanoyl -glycyl-3(R)-(2-phenethyl)-β-alanine methyl ester,
4-(2-Aminothiazol-4-yl)butanoyl-glycyl-3(R)-(2-phenethyl)-p-alanine trifluoroacetate salt,
5-(2-Pyridylamino)pentanoylglycyl -2(S)-phenylsulfonamido-β-alanine ethyl ester,
5-(2-Pyridylamino)pentanoylglycyl -2(S)-phenylsulfonamido-β-alanine trifluoroacetate salt,
4-(2-Bocamino-pyridin-6-yl)butanoyl-sarcosine-3(R)-[(2-indol-3-yl)ethyl]-β-alanine ethyl ester, 4-(2-Aminopyridin-6-yl)butanoyl-sarcosine-3(R)-[(2-indol-3-yl)ethyl]-β-alanine,
4-(2-Boc-aminopyridin-6-yl)butanoyl -glycyl-2(S)-phenylsulfonamido-β-alanine t-butyl ester,
4-(2-Aminopyridin-6-yl)butanoyl-glycyl-2(S)-phenylsulfonarnido-β-alanine,
4-(Pyridin-4-yl)butanoyl-sarcosine-3(R)-[2-(indol-3-yl)ethyl]-β-alanine ethyl ester,
4-(Pyridin-4-yl)butanoyl-sarcosine-3(R)-[2-(indol-3-yl)ethyl]-β-alanine,
4-(2-Bocamino-pyridin-6-yl)butanoyl-N-cyclopropylglycyl-3(R)-(2-phenethyl)-β-alanine ethyl ester,
4-(2-Amino-pyridin-6-yl)butanoyl-N-cyclopropylglycyl-3(R)-(2-phenethyl)-β-alanine ethyl ester hydrochloride,
4-(2-Amino-pyridin-6-yl)butanoyl-N-cyclopropylglycyl-3(R)-(2-phenethyl)-β-alanine,
4-(2-Bocamino-pyridin-6-yl)butanoyl-N-cyclopropylglycyl-3(R)-[(2-indol-3-yl)ethyl]-β-alanine,
4-(2-Amino-pyridin-6-yl)butanoyl-N-cyclopropylglycyl-3(R)-[(2-indol-3-yl)ethyl]-β-alanine,
4-(2-Bocamino-pyridin-6-yl)butanoyl-N-cyclopropylglycyl-3(R)-methyl-β-alanine ethyl ester,
4-(2-Amino-pyridin-6-yl)butanoyl-N-cyclopropylglycyl-3(R)-methyl-β-alanine ethyl ester,
4-(2-Amino-pyridin-6-yl)butanoyl-N-cyclopropylglycyl-3(R)-methyl-β-alanine,
4-(Pyridin-4-yl)butanoyl -N-(2-phenylethyl)glycyl-3(R)-(2-phenethyl)-β-alanine ethyl ester,
4-(Pyridin-4-yl)butanoyl-N-(2-phenyl)glycyl-3(R)-(2-phenethyl)-β-alanine,
4-(2-BOC-Aminopyridin-4-yl)butanoyl-N-(2-phenethyl)glycyl-3(R)-methyl-β-alanine benzyl ester,
4-(2-BOC-Aminopyridin-4-yl)butanoyl-N-(2-phenethyl)glycyl-3(R)-methyl-β-alanine,
4-(2-Aminopyridin-4-yl)butanoyl-N-(2-phenethyl)glycyl-3(R )-methyl-β-alanine,
4-(Pyridyloxy)butyrate-N-(2-phenethyl)glycyl-3 (R)-2-phenethyl-β-alanine ethyl ester,
4-(Pyridyloxy)butyrate-N-(2-phenethyl)glycyl-3(R)-2-phenethyl-β-alanine,
3-[(N-Methyl)-N-(4-pyridyl)]aminopropionyl-sarcosine-3(R)-(2-phenethyl)-β-alanine ethyl ester,
3-[(N-Methyl)-N-(4-pyridyl)]aminopropionyl-sarcosine-3(R)-(2-phenethyl)-β-alanine,
N-{N'-3-(4-t-Butoxycarbonyl-1-piperizinyl)benzoyl)glycyl}-3(R)-methyl-β-alanine benzyl ester,
N-[N'-[3-(1-Piperazinyl)benzoyl]glycyl]-3(R)-methyl-β-alanine trifluoroacetic acid salt,
N-[N'-[3-(4-t-Butoxycarbonyl-1-piperazinyl)benzoyl]glycyl]-3(R)-(2-phenethyl)-β-alanine methyl ester,
N-[N'-[3-(1-Piperazinyl)benzoyl]glycyl]-3(R)-(2-phenethyl)-β-alanine trifluoroacetic acid salt,
N-[N'-[3-(4-t-Butoxycarbonyl-1-piperazinyl)benzoyl]-N'-(2-phenethyl)glycyl]-3(R)-(2-phenethyl)-1-alanine methyl ester,
N-[N'-[3-(1-Piperazinyl)benzoyl]-N'-(2-phenethyl)glycyl]-3(R)-(2-phenethyl)-β-alanine trifluoroacetic acid salt,
4-(1,2,3,4-Tetrahydro-1,8-naphthyridin-7-yl)butanoyl-glycyl-β-alanine t-butyl ester,
4-(1,2,3,4-Tetrahydro-1,8-naphthyridin-7-yl)butanoyl-glycyl-β-alanine,
4-(1,2,3,4-Tetrahydro-1,8-naphthyridin-7-yl)butanoyl-glycyl-3(S)-pyridin-3-yl-β-alanine ethyl ester,
4-(1,2,3,4-Tetrahydro-1,8-naphthyridin-7-yl)butanoyl-glycyl-3(S)-pyridin-3-yl-β-alanine,
Ethyl N-pyridin-4-ylisonipecotyl-N-cyclopropylglycyl-3(S)-ethynyl-β-alanine,
N-Pyridin-ylisonipecotyl-N-cyclopropylglycyl-3(S)-ethynyl-β-alanine,
Ethyl N-pyridin-4-ylnipecotyl-N-cyclopropylglycyl-3(S)-ethynyl-β-alanine,
N-Pyridin-4-yinipecotyl-N-cyclopropylglycyl-3(S)-ethynyl-β-alanine,
4-(1,2,3,4-Tetrahydro-1,8-naphthyridin-5-yl)butanoyl-N-(cyclo-propyl)glycyl-3(S)-ethynyl-β-alanine ethyl ester,
4-(1,2,3,4-Tetrahydro-1,8-naphthyridin-5-yl)butanoyl-N-(cyclo-propyl)glycyl-3(S)-ethynyl-β-alanine,
3-{2-[5-(1H-Benzoimidazol-2-yl-amino)-pentanoylamino]-acetylamino}-3(S)-pyridin-3-yl-propionic acid, and
and pharmaceutically acceptable salts thereof.

3. A composition for inhibiting the binding of fibrinogen to blood platelets in a mammal, comprising an antifibrinogenic binding effective amount of a compound of claim 1 and a pharmaceutically acceptable carrier.

4. A method for inhibiting the binding of fibrinogen to blood platelets in a mammal, comprising administering to the mammal a composition of claim 3.

5. A composition for inhibiting osteoclast cellular adhesion to mammalin bone surfaces comprising a compound of claim 1 and a pharmaceutically acceptable carrier.

6. A composition for inhibiting the solubilization of mammalian bone minerals by osteoclast cells in a mammal comprising a compound of claim 2 and a pharmaceutically acceptable carrier.

7. A method for inhibiting osteoclast cellular adhesion to mammalin bone surfaces comprising treating the mammal with a pharmacologically effective amount of a composition of claim 5.

8. A method for inhibiting the solubilization of mammalian bone minerals by osteoclast cells in a mammal comprising treating the mammal with a pharmacologically effective amount of a composition of claim 6.

* * * * *